US011623964B2

(12) United States Patent
Lansing et al.

(10) Patent No.: US 11,623,964 B2
(45) Date of Patent: Apr. 11, 2023

(54) COMPOSITIONS AND METHODS RELATED TO ENGINEERED FC CONSTRUCTS

(71) Applicant: Momenta Pharmaceuticals, Inc., Cambridge, MA (US)

(72) Inventors: Jonathan C. Lansing, Reading, MA (US); Carlos J. Bosques, Arlington, MA (US); Daniel Ortiz, Stoneham, MA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 716 days.

(21) Appl. No.: 16/303,831

(22) PCT Filed: May 23, 2017

(86) PCT No.: PCT/US2017/034087
§ 371 (c)(1),
(2) Date: Nov. 21, 2018

(87) PCT Pub. No.: WO2017/205436
PCT Pub. Date: Nov. 30, 2017

(65) Prior Publication Data
US 2021/0221917 A1 Jul. 22, 2021

Related U.S. Application Data

(60) Provisional application No. 62/340,322, filed on May 23, 2016, provisional application No. 62/443,451, filed on Jan. 6, 2017.

(51) Int. Cl.
*C07K 16/46* (2006.01)
*A61P 37/06* (2006.01)
*C07K 16/00* (2006.01)
*A61K 39/395* (2006.01)

(52) U.S. Cl.
CPC ............ *C07K 16/46* (2013.01); *A61K 39/395* (2013.01); *A61P 37/06* (2018.01); *C07K 16/00* (2013.01); *C07K 16/468* (2013.01); *C07K 2317/524* (2013.01); *C07K 2317/526* (2013.01); *C07K 2317/53* (2013.01); *C07K 2317/60* (2013.01); *C07K 2317/94* (2013.01); *C07K 2319/30* (2013.01)

(58) Field of Classification Search
CPC ...... C07K 16/46; C07K 16/00; C07K 16/468; C07K 2317/524; C07K 2317/526; C07K 2317/53; C07K 2317/60; C07K 2317/94; C07K 2319/30; A61K 39/395; A61K 2039/505; A61P 37/06; A61P 29/00; A61P 37/00; A61P 37/02; A61P 43/00
See application file for complete search history.

(56) References Cited

U.S. PATENT DOCUMENTS

| | | | |
|---|---|---|---|
| 4,719,107 A | 1/1988 | Carosella et al. | |
| 5,426,641 A | 6/1995 | Afrashteh et al. | |
| 5,731,168 A | 3/1998 | Carter et al. | |
| 6,737,056 B1 | 5/2004 | Presta | |
| 7,183,076 B2 | 2/2007 | Arathoon et al. | |
| 7,803,769 B2 | 9/2010 | Sullivan et al. | |
| 7,951,917 B1 | 5/2011 | Arathoon et al. | |
| 8,216,805 B2 | 7/2012 | Carter et al. | |
| 8,592,562 B2 | 11/2013 | Kannan et al. | |
| 8,680,237 B2 | 3/2014 | Strome et al. | |
| 9,238,080 B2 | 1/2016 | Nielsen et al. | |
| 10,239,944 B2 * | 3/2019 | Bosques | A61P 5/00 |
| 11,124,573 B2 * | 9/2021 | Bosques | A61P 3/00 |
| 11,155,640 B2 * | 10/2021 | Bosques | A61P 43/00 |
| 11,220,531 B2 * | 1/2022 | Bosques | A61P 17/00 |
| 2003/0078385 A1 | 4/2003 | Arathoon | |
| 2009/0074839 A1 | 3/2009 | Milankovits | |
| 2009/0304696 A1 | 12/2009 | Lawson et al. | |
| 2010/0093979 A1 | 4/2010 | Lazar | |
| 2010/0143353 A1 | 6/2010 | Mosser et al. | |
| 2010/0216663 A1 | 8/2010 | Kolkman et al. | |
| 2010/0239633 A1 | 9/2010 | Strome et al. | |
| 2010/0286374 A1 | 11/2010 | Kannan | |
| 2011/0262477 A1 | 10/2011 | Cheng et al. | |
| 2011/0311535 A1 | 12/2011 | Dranoff et al. | |
| 2012/0149876 A1 | 6/2012 | Von Kreudenstein et al. | |
| 2012/0219551 A1 | 8/2012 | Johnson et al. | |
| 2012/0244578 A1 | 9/2012 | Kannan et al. | |
| 2013/0156765 A1 | 6/2013 | Block et al. | |
| 2013/0177555 A1 | 7/2013 | Wilkinson et al. | |
| 2014/0024111 A1 | 1/2014 | Kannan et al. | |
| 2014/0051834 A1 | 2/2014 | Hoffman et al. | |
| 2014/0066599 A2 | 3/2014 | Blein et al. | |
| 2014/0105913 A1 | 4/2014 | Strome et al. | |
| 2014/0187753 A1 | 7/2014 | Blein et al. | |

(Continued)

FOREIGN PATENT DOCUMENTS

BR PI0620639-5 11/2011
CN 101835802 9/2010

(Continued)

OTHER PUBLICATIONS

Ven Den Bremer et al., Mabs 7(4): 672-680 (Year: 2015).*
Lund et al., The Journal of Immunology 157:4963-4969 (Year: 1996).*
Mestas et al., J Immunology 172(5): 2731-2738 (Year: 2004).*
Mimoto et al., Protein Engineering, Design & Selection 26(10): 589-598 (Year: 2013).*
Cai et al., Biotechnology and Bioengineering 108(2): 404-412 (Year: 2011).*
European Search Report in Application No. 18736414.6, dated Nov. 16, 2020, 16 pages.
Grevys et al., "Open Access Fc Engineering of Human IgG1 for Altered Binding to the Neonatal Fc Receptor Affects Fc Effector Functions," The Journal of Immunology, 194(11):5497-5508.

(Continued)

*Primary Examiner* — Phuong Huynh
(74) *Attorney, Agent, or Firm* — Fish & Richardson P.C.

(57) ABSTRACT

The present disclosure relates to compositions and methods of engineered IgG Fc constructs, wherein the Fc constructs include one or more Fc domains.

7 Claims, 17 Drawing Sheets
Specification includes a Sequence Listing.

(56) References Cited

U.S. PATENT DOCUMENTS

| | | |
|---|---|---|
| 2014/0294817 A1 | 10/2014 | Mosser et al. |
| 2014/0335075 A1 | 11/2014 | Strome et al. |
| 2015/0056185 A1 | 2/2015 | Strome et al. |
| 2015/0184142 A1 | 7/2015 | Hong et al. |
| 2015/0218236 A1 | 8/2015 | Pleass |
| 2016/0229913 A1 | 8/2016 | Bosques et al. |
| 2019/0225688 A1 | 7/2019 | Bosques et al. |
| 2019/0284305 A1* | 9/2019 | Bosques ............... A61P 29/00 |
| 2019/0345206 A1* | 11/2019 | Bosques ............... A61P 31/00 |
| 2022/0033499 A1 | 2/2022 | Bosques et al. |
| 2022/0049019 A1 | 2/2022 | Bosques et al. |

FOREIGN PATENT DOCUMENTS

| | | |
|---|---|---|
| CN | 102549016 | 7/2012 |
| JP | 2007-289200 | 11/2007 |
| JP | 2010-529043 | 8/2010 |
| JP | 2011-508604 | 3/2011 |
| JP | 2011-517456 | 6/2011 |
| JP | 2014-510084 | 4/2014 |
| JP | 2015-527366 | 9/2015 |
| JP | 2015-536317 | 12/2015 |
| KR | 2010-0028599 | 3/2010 |
| RU | 2583298 | 5/2016 |
| WO | WO 1997/047732 | 12/1997 |
| WO | WO 01/45746 | 6/2001 |
| WO | WO 2005/077981 | 8/2005 |
| WO | WO 2006/106905 | 10/2006 |
| WO | WO 2008/012543 | 1/2008 |
| WO | WO 2008/131242 | 10/2008 |
| WO | WO 2008/143954 | 11/2008 |
| WO | WO 2008/151088 | 12/2008 |
| WO | WO 2009/089004 | 7/2009 |
| WO | WO 2010/085682 | 7/2010 |
| WO | WO 2010/135521 | 11/2010 |
| WO | WO 2010/135534 | 11/2010 |
| WO | WO 2011/034605 | 3/2011 |
| WO | WO-2011/073692 | 6/2011 |
| WO | WO-2012/006635 | 1/2012 |
| WO | WO 2012/123949 | 9/2012 |
| WO | WO 2014/031646 | 2/2014 |
| WO | WO 2014/060712 | 4/2014 |
| WO | WO 2015/054958 | 4/2015 |
| WO | WO 2015/095684 | 6/2015 |
| WO | WO 2015/107025 | 7/2015 |
| WO | WO 2015/107026 | 7/2015 |
| WO | WO 2015/132364 | 9/2015 |
| WO | WO 2015/132365 | 9/2015 |
| WO | WO 2015/168643 | 11/2015 |
| WO | WO-2015168643 A2 * | 11/2015 ............... A61P 1/04 |
| WO | WO 2015/184207 | 12/2015 |
| WO | WO 2017/151971 | 9/2017 |
| WO | WO 2017/205434 | 11/2017 |
| WO | WO 2017/205436 | 11/2017 |

OTHER PUBLICATIONS

Carter "Bispecific human IgG by design," J of Immunol Methods., Feb. 1, 2001, 248(1-2):7-15.
Crick et al., "A tracer study of the metabolism of p-iodophenyl urethane; the selective localization of radioactive material," Br J Pharmacol Chemother., Mar. 1952, 7(1):142-151.
European Search Report in Application No. 17803463.3, dated Jul. 15, 2020, 11 pages.
European Office Action in Application No. 15785583.4, dated Oct. 12, 2020, 4 pages.
Mestas et al., "Of Mice and Not Men: Differences between Mouse and Human Immunology," J Immunology., 2004, 172(5):2731-2738.
Sowdhamini et al., "Stereochemical modeling of disulfide bridges. Criteria for introduction into proteins by site-directed mutagenesis," Protein Eng., Nov. 1989, 3(2):95-103.

Anthony, "Identification of a receptor required for the anti-inflammatory activity of IVIG," Proc. Natl. Acad. Sci. U.S.A., Dec. 16, 2008, 105(50):19571-19578.
Atwell et al., "Stable heterodimers from remodeling the domain interface of a homodimer using a phage display library," Biol., Jul. 4, 1997, 270(1):26-35.
Boruchov AM et al., "Activating and inhibitory IgG Fc receptors on human DCs mediate opposing functions," J Clin Invest., Oct. 2005 115(10):2914-2923.
Chu et al., "Inhibition of B cell receptor-mediated activation of primary human B cells by coengagement of CD19 and FcgammaRIIb with Fc-engineered antibodies," Mol Immunol., Sep. 2008, 45(15):3926-3933.
Dall'Acqua et al., "Modulation of the Effector Functions of a Human IgG 1 through Engineering of Its Hinge Region," J. Immunol, 2006, 177:1129-1138.
Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel., Apr. 2010, 2(4)3:195-202.
European Search Report in Application No. 15785583.4, dated Nov. 7, 2017, 12 pages.
European Search Report in Application No. 17760849.4, dated Sep. 24, 2019, 12 pages.
European Search Report in Application No. 17803465.8, dated Feb. 17, 2020, 12 pages.
Gunadekaran et al., "Enhancing antibody Fc heterodimer formation through electrostatic steering effects: applications to bispecific molecules and monovalent IgG.," J Biol Chem, Jun. 18, 2010, 285(25):19637-19646.
International Preliminary Report on Patentability in International Patent Application No. PCT/US2017/020519, dated Sep. 4, 2018 (2 pages).
International Preliminary Report on Patentability in International Patent Application No. PCT/US2015/028926, dated Nov. 17, 2016, 12 pages.
International Preliminary Report on Patentability in International Patent Application No. PCT/US2017/034087, dated Nov. 27, 2018, 11 pages.
International Preliminary Report on Patentability in International Patent Application No. PCT/US2017/034084, dated Nov. 27, 2018, 10 pages.
International Search Report and Written Opinion in International Application No. PCT/US17/20519, dated Aug. 24, 2017, 17 pages.
International Search Report and Written Opinion in International Application No. PCT/US17/34084, dated Sep. 14, 2017, 19 pages.
International Search Report and Written Opinion in International Application No. PCT/US17/34087, dated Oct. 18, 2017, 20 pages.
International Search Report and Written Opinion in International Application No. PCT/US2015/028926, dated Oct. 28, 2015, 22 pages.
International Search Report and Written Opinion in International Application No. PCT/US2018/012488, dated May 25, 2018, 26 pages.
International Preliminary Report on Patentability in International Application No. PCT/US2018/012488, dated Jul. 9, 2019, 10 pages.
Kacskovics et al., "Fc receptors in livestock species," Veterinary Immunology and Immunopathology, 2004, 102:351-362.
Lund et al., "Multiple Interactions of Ig with Its Core Oligosacchadde Can Modulate Recognition by Complement and Human Fcγ Receptor I and Influence the Synthesis of Its Oligosaccharide Chains," The Journal of Immunology, 1996, 157:4963-4969.
Martens et al., "A novel one-armed anti-c-Met antibody inhibits glioblastoma growth in vivo," Clin Cancer Res., 2006, 12(20):6144-6152.
Mekhaiel et al., "Polymeric human Fc-fusion proteins with modified effector functions," Scientific Reports, Aug. 2011, 1: 124 (11 pages).
Merchant et al., "An efficient route to human bispecific IgG," Nat Biotechnol, Jul. 1998, 16(7):677-681.
Mimoto et al., "Novel asymmetrically engineered antibody Fc variant with superior FcγR binding affinity and specificity compared with afucosylated Fc variant," mAbs, Feb. 2013, 5: 229-236.

(56) References Cited

OTHER PUBLICATIONS

Office Action in Israeli Application No. 247442, dated Jun. 3, 2018, 7 pages.
Ortiz et al., "Elucidating the interplay between IgG-Fc valency and FcgR acticiation for the design of immune complex inhibitors," Science Translational Medicine, Nov. 16, 2016, 8(365):1-13.
Ridgway et al., "'Knobs-into-holes' engineering of antibody CH3 domains for heavy chain heterodimerization," *Protein Eng.*, Jul. 1996, 9(7):617-612.
Salfeld, "Isotype selection in antibody engineering," Nature Biotech, 2007, 25(12): 1369-1372.
Shields et al., "High Resolution Mapping of the Binding Site on Human IgG1 for FcγRI, FcγRII, FcγRIII, and FcRn and Design of IgG1 Variants with Improved Binding to the FcγR," J. Biol. Chem., 2001, 276(9):6591-6604.
Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res, 2007, 67: 8882-8890.
Wilson et al., "The structure of an antigenic determinant in a protein," Cell, Jul. 1984, 37(3):767-778.
Zeidler et al., "Simultaneous activation of T cells and accessory cells by a new class of intact bispecific antibody results in efficient tumor cell killing," J Immunol., Aug. 1999, 163(3):1246-1252.
Chamow et al., "A humanized, bispecific immunoadhesin-antibody that retargets CD3+ effectors to kill HIV-1-infected cells," J. Immunol., 1994, 153:4268-4280 (Abstract Only).
Rajpal et al., "Introduction: Antibody Structure and Function," Therapeutic Fc-Fusion Proteins, 2014, Chapter 1, 43 pages.
Dick Jr et al., "C-terminal lysine variants in fully human monoclonal antibodies: investigation of test methods and possible causes," Biotechnology and Bioengineering 2008, 100(6):1132-1143.
European Search Report in Application No. 17760849.4, dated Jan. 11, 2021, 4 pages.
European Office Action in Application No. 17803465.8, dated Jan. 20, 2021, 8 pages.
Kinder et al., "Engineered protease-resistant antibodies with selectable cell-killing functions," J of Biol Chem., Oct. 25, 2013, 288(43):30843-30854.
Armour et al., "Differential binding to human FcγRIIa and FcγRIIb receptors by human IgG wildtype and mutant antibodies," Molecular immunology, 2003, 40(9):585-593.
Jain et al., "Fully recombinant IgG2a Fc multimers (stradomers) effectively treat collagen-induced arthritis and prevent idiopathic thrombocytopenic purpura in mice," Arthritis Res Ther., Aug. 20, 2012, 14(4):R192.
Radaev et al., "Recognition of IgG by Fcγ receptor: the role of Fc glycosylation and the binding of peptide inhibitors," Journal of Biological Chemistry, 2001, 276(19):16478-16483.

* cited by examiner

Construct 1

Construct 2

Construct 6

COMPOSITIONS AND METHODS RELATED TO ENGINEERED FC CONSTRUCTS

CROSS-REFERENCE TO RELATED APPLICATIONS

This application is a national phase application under 35 U.S.C. § 371 of PCT Application No. PCT/US2017/034087, filed May 23, 2017, which claims the benefit of prior U.S. Provisional Application Ser. No. 62/340,322, filed May 23, 2016, and or prior U.S. Provisional Application Ser. No. 62/443,451, filed Jan. 6, 2017. The disclosures of the above applications are hereby incorporated by reference in their entirety.

BACKGROUND

Therapeutic proteins, e.g., therapeutic antibodies and Fc-fusion proteins, have rapidly become a clinically important drug class for patients with immunological and inflammatory diseases.

SUMMARY OF THE INVENTION

The present disclosure features biologically active Fc domain-containing therapeutic constructs. Such constructs may have desirable serum half-life and/or binding affinity and/or avidity for Fc receptors. These constructs are useful, e.g., to reduce inflammation in a subject, to promote clearance of autoantibodies in a subject, to suppress antigen presentation in a subject, to block an immune response, e.g., block an immune complex-based activation of the immune response in a subject, and to treat immunological and inflammatory diseases (e.g., autoimmune diseases) in a subject. The Fc constructs described herein can be used to treat patients having immunological and inflammatory diseases without significant stimulation of immune cells.

In general, the disclosure features Fc constructs having 2-10 Fc domains, e.g., Fc constructs having 2, 3, 4, 5, 6, 7, 8, 9, or 10 Fc domains, wherein at least one of the Fc domains includes at least one amino acid modification that alters one or more of (i) binding affinity to one or more Fc receptors, (ii) effector functions, (iii) the level of Fc domain sulfation, (iv) half-life, (v) protease resistance, (vi) Fc domain stability, and/or (vii) susceptibility to degradation. In some embodiments, the Fc construct includes 2-10 Fc domains, 2-5 Fc domains, 2-4 Fc domains, 2-3 Fc domains, 3-5 Fc domains, 2-8 Fc domains, or 2-6 Fc domains. In some embodiments, the Fc construct includes 5-10 Fc domains. The construct may include 2-6 (e.g., 2, 3, 4, 5, or 6) associated polypeptides, each polypeptide including at least one Fc domain monomer, wherein each Fc domain monomer of the construct is the same or differs by no more than 20 amino acids (e.g., no more than 15, 10 amino acids), e.g., no more than 20, 15, 10, 8, 7, 6, 5, 4, 3 or 2 amino acids, from another monomer of the construct. The Fc constructs described herein do not include an antigen-binding domain of an immunoglobulin. In some embodiments, the Fc construct (or an Fc domain within an Fc construct) is formed entirely or in part by association of Fc domain monomers that are present in different polypeptides. In certain embodiments, the Fc construct does not include an additional domain (e.g., an IgM tailpiece or an IgA tailpiece) that promotes association of two polypeptides. In other embodiments, covalent linkages are present in the Fc construct only between two Fc domain monomers that join to form an Fc domain. In other embodiments, the Fc construct does not include covalent linkages between Fc domains. In still other embodiments, the Fc construct provides for sufficient structural flexibility such that all or substantially all of the Fc domains in the Fc construct are capable of simultaneously interacting with an Fc receptor on a cell surface. In some embodiments, the Fc construct includes at least two Fc domains joined through a linker (e.g., a flexible amino acid spacer). In one embodiment, the domain monomers are different in primary sequence from wild-type or from each other in that they have dimerization selectivity modules.

An Fc construct of the disclosure can be in a pharmaceutical composition that includes a substantially homogenous population (e.g., at least 85%, 90%, 95%, 98%, or 99% homogeneous) of the Fc construct having 2-10 Fc domains (e.g., 2-8 Fc domains, 2-6 Fc domains, 2-4 Fc domains, 2-3 Fc domains, 3-5 Fc domains, or 5-10 Fc domains) e.g., a construct having 2, 3, 4, 5, 6, 7, 8, 9, or 10 Fc domains, such as those described herein. Consequently, pharmaceutical compositions can be produced that do not have substantial aggregation or unwanted multimerization of Fc constructs.

In one aspect, the Fc construct includes three polypeptides that form two Fc domains. The first polypeptide has the formula A-L-B, wherein A includes a first Fc domain monomer; L is a linker; and B includes a second Fc domain monomer. The second polypeptide includes a third Fc domain monomer, and the third polypeptide includes a fourth Fc domain monomer. In this aspect, the first Fc domain monomer and the third Fc domain monomer combine to form a first Fc domain. Similarly, the second Fc domain monomer and the fourth Fc domain monomer combine to form a second Fc domain. Exemplary Fc constructs of this aspect of the disclosure are illustrated in FIGS. 4 and 6.

In certain embodiments, the first Fc domain monomer and the third Fc domain monomer include complementary dimerization selectivity modules that promote dimerization between these Fc domain monomers. In other embodiments, the second Fc domain monomer and the fourth Fc domain monomer include complementary dimerization selectivity modules that promote dimerization between these Fc domain monomers.

In certain embodiments, one or more of A, B, the second polypeptide, and the third polypeptide consists of an Fc domain monomer. In one embodiment, each of A, B, the second polypeptide, and the third polypeptide consist of an Fc domain monomer.

In certain embodiments, the Fc construct can further include a heterologous moiety, e.g., a peptide, e.g., a peptide that binds a serum protein, e.g., an albumin-binding peptide. The moiety may be joined to the N-terminus or the carboxy-terminus of B or the third polypeptide, e.g., by way of a linker.

In certain embodiments, the Fc construct further includes an IgG $C_L$ antibody constant domain and an IgG $C_H1$ antibody constant domain. The IgG $C_H1$ antibody constant domain can be attached to the N-terminus of A or the second polypeptide, e.g., by way of a linker.

In other embodiments, the second and third polypeptides of the Fc construct have the same amino acid sequence.

In another aspect, the disclosure features an Fc construct that includes four polypeptides that form three Fc domains. The first polypeptide has the formula A-L-B, wherein A includes a first Fc domain monomer; L is a linker; and B includes a second Fc domain monomer. The second polypeptide has the formula wherein A' includes a third Fc domain monomer; L' is a linker; and B' includes a fourth Fc domain monomer. The third polypeptide includes a fifth Fc domain monomer, and the fourth polypeptide includes a sixth Fc domain monomer. In this aspect, A and A' combine to form a first Fc domain, B and fifth Fc domain monomer combine to form a second Fc domain, and B' and sixth Fc domain monomer combine to form a third Fc domain. An exemplary Fc construct of this aspect of the disclosure is illustrated in FIG. 5.

In certain embodiments, A and A' each include a dimerization selectivity module that promotes dimerization between these Fc domain monomers. In other embodiments, B and the fifth Fc domain monomer each include a dimerization selectivity module that promotes dimerization between these Fc domain monomers. In yet other embodiments, B' and the sixth Fc domain monomer each include a dimerization selectivity module that promotes dimerization between these Fc domain monomers.

In certain embodiments, one or more of A, B, A', B', the third polypeptide, and the fourth polypeptide consists of an Fc domain monomer. In one embodiment, each of A, B, A', B', the third polypeptide, and the fourth polypeptide consists of an Fc domain monomer.

In certain embodiments, the Fc construct further includes an IgG $C_L$ antibody constant domain and an IgG $C_H1$ antibody constant domain, wherein the IgG $C_L$ antibody constant domain is attached to the N-terminus of the IgG $C_H1$ antibody constant domain by way of a linker and the IgG $C_H1$ antibody constant domain is attached to the N-terminus of A, e.g., by way of a linker. In one embodiment, the Fc construct further includes a second IgG $C_L$ antibody constant domain and a second IgG $C_H1$ antibody constant domain, wherein the second IgG $C_L$ antibody constant domain is attached to the N-terminus of the second IgG $C_H1$ antibody constant domain, e.g., by way of a linker and the second IgG $C_H1$ antibody constant domain is attached to the N-terminus of A', e.g., by way of a linker.

In certain embodiments, the Fc construct further includes a heterologous moiety, e.g., a peptide, e.g., an albumin-binding peptide joined to the N-terminus or C-terminus of B or B', e.g., by way of a linker.

In other embodiments, the first and second polypeptides of the Fc construct have the same amino acid sequence and the third and fourth polypeptides of the Fc construct have the same amino acid sequence.

In another aspect, the disclosure features an Fc construct that includes two polypeptides. The first polypeptide has the formula A-L-B, wherein A includes a first Fc domain monomer; L is a linker; and B includes a serum protein-binding moiety, e.g., an albumin binding peptide. The second polypeptide includes a second Fc domain monomer. In this aspect, the first Fc domain monomer and the second Fc domain monomer combine to form an Fc domain.

In certain embodiments, the first Fc domain monomer and the second Fc domain monomer include complementary dimerization selectivity modules that promote dimerization between the first Fc domain monomer and the second Fc domain monomer.

In certain embodiments, A and the second polypeptide each consists of an Fc domain monomer.

In yet another aspect, the disclosure features an Fc construct that includes two polypeptides. The first polypeptide has the formula A-L1-B-L2-C, wherein A includes an IgG $C_L$ antibody constant domain; L1 and L2 are each a linker; B includes an IgG $C_H1$ antibody constant domain; and C includes a first Fc domain monomer. The second polypeptide has the formula A'-L1'-13'-L2'-C', wherein A' includes an IgG $C_L$ antibody constant domain; L1' and L2' are each a linker; B' includes an IgG $C_H1$ antibody constant domain; and C' includes a second Fc domain monomer. In this aspect, the first Fc domain monomer and the second Fc domain monomer combine to form an Fc domain. An exemplary Fc construct of this aspect of the disclosure is illustrated in FIG. 7A.

In certain embodiments, the first Fc domain monomer and the second Fc domain monomer include dimerization selectivity modules that promote dimerization between the first Fc domain monomer and the second Fc domain monomer.

In certain embodiments, C and C' each consist of an Fc domain monomer.

In certain embodiments, the Fc construct further includes a serum protein binding moiety, e.g., an albumin-binding peptide joined to the N-terminus or C-terminus of C or C' by way of a linker.

In yet another aspect, the disclosure features an Fc construct that includes four or more polypeptides. The first polypeptide has the formula A-L1-B-L2-C, wherein A includes an IgG $C_L$ antibody constant domain; L1 and L2 are each a linker; B includes an IgG $C_H1$ antibody constant domain; and C includes a first Fc domain monomer. The second polypeptide has the formula A'-L1'-13'-L2'-C', wherein A' includes an IgG $C_L$ antibody constant domain; L1' and L2' are each a linker; B' includes an IgG $C_H1$ antibody constant domain; and C' includes a second Fc domain monomer. In this aspect, the first Fc domain monomer combines with a third Fc domain monomer to form a first Fc domain and the second Fc domain monomer combines with a fourth Fc domain monomer to form a second Fc domain. Additionally, the IgG $C_H1$ antibody constant domain of the first polypeptide combines with the IgG $C_L$ antibody constant domain of the second polypeptide and the IgG $C_H1$ antibody constant domain of the second polypeptide combines with the IgG $C_L$ antibody constant domain of the first polypeptide to form an Fc construct that includes two or more Fc domains. An exemplary Fc construct of this aspect of the disclosure is illustrated in FIG. 7B.

In another aspect, the disclosure features an Fc construct that includes two polypeptides. The first polypeptide includes a first Fc domain monomer and the second polypeptide includes a second Fc domain monomer. In this aspect, the first and second Fc domain monomers combine to form an Fc domain. An exemplary Fc construct of this aspect of the disclosure is illustrated in FIG. 1. Further in this aspect, the first Fc domain monomer and the second Fc domain monomer each include a dimerization selectivity module that promotes dimerization between the first Fc domain monomer and the second Fc domain monomer. Exemplary Fc constructs of this embodiment are illustrated in FIGS. 2 and 3.

In certain embodiments, the first and second polypeptides each consist of an Fc domain monomer.

In certain embodiments, the Fc construct further includes a serum protein binding moiety, e.g., an albumin-binding peptide joined to the N-terminus or C-terminus of the first or second polypeptide, e.g., by way of a linker.

In another aspect, the disclosure features an Fc construct that includes two polypeptides. The first polypeptide has the formula A-L-B, wherein A includes a first Fc domain monomer; L is a linker; and B includes a second Fc domain monomer. The second polypeptide has the formula wherein A' includes a third Fc domain monomer; L' is a linker; and B' includes a fourth Fc domain monomer. In this aspect, the first and second Fc domain monomers each include an engineered cavity into their respective $C_H3$ antibody constant domains and the second and fourth Fc domain monomers each include an engineered protuberance into their respective C_H3 antibody constant domains, wherein the engineered cavity and the engineered protuberance are positioned to form a protuberance-into-cavity pair. Also in this aspect, the first Fc domain monomer and the third Fc domain monomer combine to form a first Fc domain and the second Fc domain monomer and the fourth Fc domain monomer combine to form a second Fc domain.

In certain embodiments, one or more of A, B, A', and B' consists of an Fc domain monomer. In one embodiment, each of A, B, A', and B' consists of an Fc domain monomer.

In certain embodiments, the Fc construct further includes a serum protein binding moiety, e.g., an albumin-binding peptide joined to the N-terminus or C-terminus of B or B', e.g., by way of a linker.

In certain embodiments, the Fc construct further includes an IgG $C_L$ antibody constant domain and an IgG $C_H1$ antibody constant domain, wherein the IgG $C_L$ antibody constant domain is attached to the N-terminus of the IgG $C_H1$ antibody constant domain, e.g., by way of a linker and the IgG $C_H1$ antibody constant domain is attached to the N-terminus of A by way of a linker. In one embodiment, the Fc construct further includes a second IgG $C_L$ antibody constant domain and a second IgG $C_H1$ antibody constant domain, wherein the second IgG $C_L$ antibody constant domain is attached to the N-terminus of the second IgG $C_H1$ antibody constant domain by way of a linker and the second IgG $C_H1$ antibody constant domain is attached to the N-terminus of A' by way of a linker.

In another aspect, the disclosure features an Fc construct consisting of a) a first polypeptide having the formula A-L-B; wherein A includes or consists of a first Fc domain monomer; L is a linker; and B includes or consists of a second Fc domain monomer; b) a second polypeptide having the formula A'-L'-B'; wherein A' includes or consists of a third Fc domain monomer; L' is a linker; and B' includes or consists of a fourth Fc domain monomer; c) a third polypeptide that includes or consists of a fifth Fc domain monomer; and d) a fourth polypeptide that includes or consists of a sixth Fc domain monomer. A of the first polypeptide and A' of the second polypeptide combine to form a first Fc domain; B of the first polypeptide and the fifth Fc domain monomer combine to form a second Fc domain; and B' of the second polypeptide and the sixth Fc domain monomer combine to form a third Fc domain. Each of the first and third Fc domain monomers includes complementary dimerization selectivity modules that promote dimerization between the first Fc domain monomer and the third Fc domain monomer, each of the second and fifth Fc domain monomers includes complementary dimerization selectivity modules that promote dimerization between the second Fc domain monomer and the fifth Fc domain monomer, and each of the fourth and sixth Fc domain monomers includes complementary dimerization selectivity modules that promote dimerization between the fourth Fc domain monomer and the sixth Fc domain monomer; wherein the Fc construct contains no more than three Fc domains.

In some embodiments of this aspect, either the first Fc domain monomer or the third Fc domain monomer includes a negatively-charged amino acid substitution, and the other Fc domain monomer includes a positively-charged amino acid substitution, either the second and fourth Fc domain monomers or the fifth and sixth Fc domain monomers include an engineered protuberance, and the other Fc domain monomers include an engineered cavity. In some embodiments, linker L1, L2, L1', and/or L2' is 3-200 amino acids in length. In some embodiments, linker L and/or L' comprises, consists of, or consists essentially of the sequence of any one of SEQ ID NOs: 1-27 and 51-55. In some embodiments, linker L and/or L' comprises, consists of, or consists essentially of the sequence of any one of SEQ ID NOs: 1-27 and 51-55 with up to 10 (e.g., up to 9, 8, 7, 6, 5, 4, 3, 2, or 1) single amino acid modifications (e.g., substitutions, e.g., conservative substitutions).

In another aspect, the disclosure features an Fc construct consisting of a) a first polypeptide having the formula A-L1-B-L2-C; wherein A includes or consists of a first Fc domain monomer; L1 is a linker; B includes or consists of a second Fc domain monomer; L2 is a linker; and C includes or consists of a third Fc domain monomer; and b) a second polypeptide having the formula A'-L1'-B'-L2'-C'; wherein A' includes or consists of a fourth Fc domain monomer; L1' is a linker; B' includes or consists of a fifth Fc domain monomer; L2' is a linker; and C' includes or consists of a sixth Fc domain monomer; c) a third polypeptide that includes or consists of a seventh Fc domain monomer; d) a fourth polypeptide that includes or consists of a eighth Fc domain monomer; e) a fifth polypeptide that includes or consists of a ninth Fc domain monomer; and f) a sixth polypeptide that includes or consists of a tenth Fc domain monomer. A of the first polypeptide and the seventh Fc domain monomer combine to form a first Fc domain; B of the first polypeptide and B' of the second polypeptide combine to form a second Fc domain; C of the first polypeptide and the eighth Fc domain monomer combine to form a third Fc domain, A' of the second polypeptide and the ninth Fc domain monomer combine to form a fourth Fc domain, and C' of the second polypeptide and the tenth Fc domain monomer combine to form a fifth Fc domain. Each of the first and seventh Fc domain monomers includes complementary dimerization selectivity modules that promote dimerization between the first Fc domain monomer and the seventh Fc domain monomer, each of the second and fifth Fc domain monomers includes complementary dimerization selectivity modules that promote dimerization between the second Fc domain monomer and the fifth Fc domain monomer, each of the third and eighth Fc domain monomers includes complementary dimerization selectivity modules that promote dimerization between the third Fc domain monomer and the eighth Fc domain monomer; each of the fourth and ninth Fc domain monomers includes complementary dimerization selectivity modules that promote dimerization between the fourth Fc domain monomer and the ninth Fc domain monomer; and each of the sixth and tenth Fc domain monomers includes complementary dimerization selectivity modules that promote dimerization between the sixth domain monomer and the tenth Fc domain monomer; wherein the Fc construct contains no more than five Fc domains.

In some embodiments of this aspect, each of the first, third, fourth, and sixth Fc domain monomers includes an engineered protuberance, the second Fc domain monomer includes a negatively-charged amino acid substitution, the fifth Fc domain monomer includes a positively-charged amino acid substitution, and each of the seventh, eighth, ninth, and tenth Fc domain monomers includes an engineered cavity. In some embodiments, linker L1, L2, L1', and/or L2' is 3-200 amino acids in length. In some embodiments, linker L1, L2, L1', and/or L2' comprises, consists of, or consists essentially of the sequence of any one of SEQ ID NOs: 1, 2, and 3.

In another aspect, the disclosure features an Fc construct consisting of a) a first polypeptide having the formula A-L1-B-L2-C; wherein A includes or consists of a first Fc domain monomer; L1 is a linker; B includes or consists of a second Fc domain monomer; L2 is a linker; and C includes or consists of a third Fc domain monomer; and b) a second polypeptide having the formula A'-L1'-B'-L2'-C'; wherein A' includes or consists of a fourth Fc domain monomer; L1' is a linker; B' includes or consists of a fifth Fc domain monomer; L2' is a linker; and C' includes or consists of a sixth Fc domain monomer; c) a third polypeptide that includes or consists of a seventh Fc domain monomer; d) a fourth polypeptide that includes or consists of a eighth Fc domain monomer; e) a fifth polypeptide that includes or consists of a ninth Fc domain monomer; f) a sixth polypeptide that includes or consists of a tenth Fc domain monomer. A of the first polypeptide and A' of the second polypeptide combine to form a first Fc domain; B of the first polypeptide and the seventh Fc domain monomer combine to form a second Fc domain; C of the first polypeptide and the eighth Fc domain monomer combine to form a third Fc domain, B' of the second polypeptide and the ninth Fc domain monomer combine to form a fourth Fc domain, and C' of the second polypeptide and the tenth Fc domain monomer combine to form a fifth Fc domain. Each of the first and fourth Fc domain monomers includes complementary dimerization selectivity modules that promote dimerization between the first Fc domain monomer and the fourth Fc domain monomer, each of the second and seventh Fc domain monomers includes complementary dimerization selectivity modules that promote dimerization between the second Fc domain monomer and the seventh Fc domain monomer, each of the third and eighth Fc domain monomers includes complementary dimerization selectivity modules that promote dimerization between the third Fc domain monomer and the eighth Fc domain monomer; each of the fifth and ninth Fc domain monomers includes complementary dimerization selectivity modules that promote dimerization between the fifth Fc domain monomer and the ninth Fc domain monomer; and each of the sixth and tenth Fc domain monomers includes complementary dimerization selectivity modules that promote dimerization between the sixth domain monomer and the tenth Fc domain monomer; wherein the Fc construct contains no more than five Fc domains.

In some embodiments of this aspect, the first Fc domain monomer includes a negatively-charged amino acid substitution, the fourth Fc domain monomer includes a positively-charged amino acid substitution, each of the second, third, fifth, and sixth Fc domain monomers includes an engineered protuberance, and each of the seventh, eighth, ninth, and tenth Fc domain monomers includes an engineered cavity. In some embodiments, linker L1, L2, L1', and/or L2' is 3-200 amino acids in length. In some embodiments, linker L1, L2, L1', and/or L2' comprises, consists of, or consists essentially of the sequence of any one of SEQ ID NOs: 1, 2, and 3.

In another aspect, the disclosure features an Fc construct that includes one or more Fc domains, wherein the Fc construct is assembled from a single polypeptide sequence. The polypeptide has the formula A-L-B, wherein A includes a first Fc domain monomer; L is a linker (optionally a cleavable linker with, e.g., one, two or more cleavage sites); and B includes a second Fc domain monomer. The linker can be an amino acid spacer of sufficient length (e.g., at least 15 amino acids, preferably at least about 20 amino acid residues in length, e.g., 15-200 amino acids in length) and flexibility that the first Fc domain monomer and the second Fc domain monomer of the polypeptide combine to form an Fc domain. In certain embodiments, the first Fc domain monomer and the second Fc domain monomer include complementary dimerization selectivity modules that promote dimerization between the first Fc domain monomer and the second Fc domain monomer. Such a construct can be formed from expression of a single polypeptide sequence in a host cell. In one embodiment, the polypeptide has the formula A-L1-B-L2-C, wherein A includes a first Fc domain monomer; L1 is a linker (optionally a cleavable linker with, e.g., one, two, or more cleavage sites); B includes a second Fc domain monomer; L2 is a linker; and C is a third Fc domain monomer. The linker can be an amino acid spacer of sufficient length (e.g., at least 15 amino acids, preferably at least about 20 amino acid residues in length, e.g., 15-200 amino acids in length) and flexibility that the first Fc domain monomer and the second Fc domain monomer of the polypeptide combine to form an Fc domain. In certain embodiments, the first Fc domain monomer and the second Fc domain monomer include complementary dimerization selectivity modules that promote dimerization between the first Fc domain monomer and the second Fc domain monomer. An example of an Fc construct of this embodiment, including three Fc domains, is depicted in FIG. 10.

In any of the Fc constructs described herein, at least one of the Fc domains includes an amino acid modification that alters one or more of (i) binding affinity to one or more Fc receptors, (ii) effector functions, (iii) the level of Fc domain sulfation, (iv) half-life, (v) protease resistance, (vi) Fc domain stability, and/or (vii) susceptibility to degradation. In any of the Fc constructs described herein, the amino acid modification that alters binding affinity to one or more Fc receptors is any one of the amino acid modifications in Table 2. In any of the Fc constructs described herein, the amino acid modification that alters binding affinity to one or more Fc receptors is S267E/L328F. In some embodiments, the Fc receptor is FcγRIIb. In some cases, the modification described herein increases affinity to the FcγRIIb receptor. In some cases, the S267E/L328F modification increases binding affinity to FcγRIIb. In any of the Fc constructs described herein, the amino acid modification that alters effector functions is any one of the amino acid modifications in Table 6. In any of the Fc constructs described herein, the amino acid modification that alters the level of Fc domain sulfation is 241F, 243F, 246K, 260T, or 301R. In any of the Fc constructs described herein, the amino acid modification that alters half-life is any one of the amino acid modifications in Table 4. In any of the Fc constructs described herein, the amino acid modifications that alter protease resistance are selected from the following sets: 233P, 234V, 235A, and 236del; 237A, 239D, and 332E; 237D, 239D, and 332E; 237P, 239D, and 332E; 237Q, 239D, and 332E; 237S, 239D, and 332E; 239D, 268F, 324T, and 332E; 239D, 326A, and 333A; 239D and 332E; 243L, 292P, and 300L; 267E, 268F, 324T, and 332E; 267E and 332E; 268F, 324T, and 332E; 326A, 332E, and 333A; or 326A and 333A. In any of the Fc constructs described herein, the amino acid modification that alters Fc domain stability is any one of the amino acid modifications in Table 8. In any of the Fc constructs described herein, the amino acid modification that alters Fc domain susceptibility to degradation is C233X, D234X, K235X, S236X, T236X, H237X, C239X, S241X, and G249X, wherein X is any amino acid.

In another aspect, the disclosure features an Fc construct that includes (a) a first polypeptide having the formulation A-L-B; wherein A includes or consists of a first Fc domain monomer; L is a linker; and B includes or consists of a second Fc domain monomer; (b) a second polypeptide having the formula A'-L'-B'; wherein A' includes or consists of a third Fc domain monomer; L' is a linker; and B' includes or consists of a fourth Fc domain monomer; (c) a third polypeptide that includes or consists of a fifth Fc domain monomer; and (d) a fourth polypeptide that includes or consists of a sixth Fc domain monomer. In some cases, a of first polypeptide and A' of second polypeptide combine to form a first Fc domain, B of first polypeptide and fifth Fc domain monomer combine to form a second Fc domain, and B' of second polypeptide and sixth Fc domain monomer combine to form a third Fc domain. In some cases, the first and second polypeptides comprise, consist of, or consist essentially of the sequence of SEQ ID NO: 50, and the third and fourth polypeptide comprise, consist of, or consist essentially of the sequence of SEQ ID NO: 48. In some embodiments of the disclosure, each of the first and second polypeptides comprises, consists of, or consists essentially of the sequence of SEQ ID NO: 50 with up to 10 (e.g., up to 9, 8, 7, 6, 5, 4, 3, 2, or 1) single amino acid modifications (e.g., substitutions, e.g., conservative substitutions), and the third and fourth polypeptide comprise, consist of, or consist essentially of the sequence of SEQ ID NO: 48 with up to 10 (e.g., up to 9, 8, 7, 6, 5, 4, 3, 2, or 1) single amino acid modifications (e.g., substitutions, e.g., conservative substitutions).

The Fc domain monomers of an Fc domain of the construct can have the same primary amino acid sequence. For example, the Fc domain monomers of an Fc domain may both be a wild-type sequence, or both Fc domain monomers of an Fc domain may have the same dimerization selectivity module, e.g., both Fc domain monomers of an Fc domain may have identical reverse charge mutations in at least two positions within the ring of charged residues at the interface between $C_H3$ domains.

In any of the Fc constructs described herein, the Fc domain monomers of an Fc domain of a construct can have different sequences, e.g., sequences that differ by no more than 20 amino acids (e.g., no more than 15, 10 amino acids), e.g., no more than 20, 15, 10, 8, 7, 6, 5, 4, 3 or 2 amino acids, between two Fc monomers (i.e., between the Fc domain monomer and another monomer of the Fc construct). For example, Fc monomer sequences of a construct described herein may be different because complementary dimerization selectivity modules of any of the Fc constructs can include an engineered cavity in the $C_H3$ antibody constant domain of one of the domain monomers and an engineered protuberance in the $C_H3$ antibody constant domain of the other of the Fc domain monomers, wherein the engineered cavity and the engineered protuberance are positioned to form a protuberance-into-cavity pair of Fc domain monomers. Exemplary engineered cavities and protuberances are shown in Table 9. In other embodiments, the complementary dimerization selectivity modules include an engineered (substituted) negatively-charged amino acid in the $C_H3$ antibody constant domain of one of the domain monomers and an engineered (substituted) positively-charged amino acid in the $C_H3$ antibody constant domain of the other of the Fc domain monomers, wherein the negatively-charged amino acid and the positively-charged amino acid are positioned to promote formation of an Fc domain between complementary domain monomers. Exemplary complementary amino acid changes are shown in Table 10.

In some embodiments, in addition to the dimerization selectivity modules (e.g., the engineered cavities and protuberances, or the engineered positively and negatively-charged amino acids (see, e.g., exemplary amino acid changes in Tables 1 and 2)), an Fc construct described herein may also include additional amino acid substitutions from a wild type sequence in the Fc monomer sequences to, e.g., help to stabilize the Fc construct or to prevent protein aggregation.

In some embodiments, an Fc construct described herein includes 2-10 Fc domains (e.g., 2-8 Fc domains, 2-6 Fc domains, 2-4 Fc domains, 2-3 Fc domains, 3-5 Fc domains, or 5-10 Fc domains; e.g., 2, 3, 4, 5, 6, 7, 8, 9, 10 domains), wherein at least two of the Fc domains of the construct have different dimerization selectivity modules. In some embodiments, an Fc construct described herein includes 5-10 Fc domains (e.g., 5, 6, 7, 8, 9, 10 domains), wherein at least two of the Fc domains of the construct have different dimerization selectivity modules. For example, constructs 5, 8, 9 and 10 have at least one Fc domain including engineered cavity and protuberance and at least one Fc domain including complementary reverse charge mutations.

In other embodiments, one or more linker in an Fc construct described herein is a bond.

In other embodiments, one or more linker in an Fc construct described herein is a spacer, e.g., an amino acid spacer of 2-200 amino acids (e.g., 2-100, 3-200, 3-150, 3-100, 3-60, 3-50, 3-40, 3-30, 3-20, 3-10, 3-8, 3-5, 4-30, 5-30, 6-30, 8-30, 10-20, 10-30, 12-30, 14-30, 20-30, 15-25, 15-30, 18-22, and 20-30 amino acids).

In certain embodiments, the amino acid spacer is a glycine and/or serine rich spacer, e.g., the spacer comprises, consists of, or consists essentially of two or more motifs of the sequence GS, GGS, GGGGS (SEQ ID NO: 1), GGSG (SEQ ID NO: 2), or SGGG (SEQ ID NO: 3). In some cases, the amino acid spacer includes only glycine, only serine, or only serine and glycine. In some cases, the amino acid spacer includes 2-30 amino acids (e.g., 20 amino acids) and includes only glycine. In some cases, the spacer includes 3-20 amino acids (e.g., 20 amino acids) and includes only glycine and serine.

In certain embodiments, when an Fc construct includes an albumin-binding peptide, the albumin-binding peptide comprises, consists of, or consists essentially of the sequence of DICLPRWGCLW (SEQ ID NO: 28). In certain embodiments, when an Fc construct includes an albumin-binding peptide, the albumin-binding peptide comprises, consists of, or consists essentially of the sequence of DICLPRWGCLW (SEQ ID NO: 28) with up to 10 (e.g., up to 9, 8, 7, 6, 5, 4, 3, 2, or 1) single amino acid modifications (e.g., substitutions, e.g., conservative substitutions).

In other embodiments, one or more of the Fc domain monomers in the Fc constructs described herein includes an IgG hinge domain, an IgG $C_H2$ antibody constant domain, and an IgG $C_H3$ antibody constant domain.

In certain embodiments, each of the Fc domain monomers in the foregoing Fc constructs includes an IgG hinge domain, an IgG $C_H2$ antibody constant domain, and an IgG $C_H3$ antibody constant domain.

In certain embodiments, the IgG is of a subtype selected from the group consisting of IgG1, IgG2a, IgG2b, IgG3, and IgG4.

In certain embodiments, each of the Fc domain monomers have no more than 10 (e.g., no more than 1, 2, 3, 4, 5, 6, 7, 8, 9, or 10) amino acid modifications. In some embodiments, one or more of the Fc domain monomers is a human IgG Fc (e.g., IgG1, IgG2a, IgG2b, IgG3, or IgG4). In some embodiments, one or more of the Fc domain monomers is a human IgG Fc domain monomer having up to ten (e.g., up to 1, 2, 3, 4, 5, 6, 7, 8, 9, or 10) amino acid modifications.

In yet another aspect, the disclosure features a pharmaceutical composition that includes a substantially homogenous (e.g., at least 85%, 90%, 95%, 97%, 98%, 99% homogeneous) population of any Fc construct described herein. In one embodiment, a sterile syringe or vial qualified for pharmaceutical use contains a pharmaceutical composition wherein the only or primary active ingredient is a substantially homogenous (e.g., at least 85%, 90%, 95%, 98%, or 99% homogeneous) population of any one of the Fc constructs described herein. The pharmaceutical composition may include one or more inactive ingredients, e.g., selected from salts, detergents, surfactants, bulking agents, polymers, preservatives, and other pharmaceutical excipients. In another embodiment, the substantially homogenous pharmaceutical composition contains less than 10%, less than 5%, less than 4%, less than 3%, less than 2%, less than 1%, or less than 0.5% aggregates or unwanted multimers of the Fc construct.

In another aspect, the disclosure features a method of preparing any one of the foregoing Fc constructs. The method includes providing a host cell including a polynucleotide or polynucleotides encoding the polypeptides needed to assemble the Fc construct, expressing polypeptides in the host cell under conditions that allow for the formation of the Fc construct, and recovering (e.g., purifying) the Fc construct.

In some embodiments, the Fc construct is formed at least in part by association of Fc domain monomers that are present in different polypeptides. In certain embodiments, the Fc construct is formed by association of Fc domain monomers that are present in different polypeptides. In these embodiments, the Fc construct does not include an additional domain that promotes association of two polypeptides (e.g., an IgM tailpiece or an IgA tailpiece). In other embodiments, covalent linkages (e.g., disulfide bridges) are present only between two Fc domain monomers that join to form an Fc domain. In other embodiments, the Fc construct does not include covalent linkages (e.g., disulfide bridges) between Fc domains. In still other embodiments, the Fc construct provides for sufficient structural flexibility such that all or substantially all of the Fc domains in the Fc construct are capable of simultaneously interacting with an Fc receptor on a cell surface. In certain examples of any of these embodiments, the Fc construct includes at least two Fc domains joined through a linker (e.g., a flexible amino acid spacer).

In one embodiment, the Fc domain monomers of an Fc domain are found in different polypeptide chains that associate to form the Fc domain. For example, the constructs depicted in FIG. 4 and FIG. 6 have two Fc domains including three associated polypeptides. One of the three polypeptides includes two Fc domain monomers and the other two of the polypeptides each includes one Fc domain monomer. The construct depicted in FIG. 5 has three Fc domains including four associated polypeptides; two of the four polypeptides have two Fc domain monomers and the other two of the four polypeptides each has one Fc domain monomer. The Fc construct depicted in FIG. 7B can have n Fc domains (where n is 2-10) including 2n polypeptides, each polypeptide including an Fc domain monomer, an IgG $C_L$ antibody constant domain, and an IgG $C_H1$ antibody constant domain. The constructs depicted in FIGS. 8 and 9 each has five Fc domains including six associated polypeptides. Two of the six polypeptides have three Fc domain monomers and the other four of the six polypeptides each has one Fc domain monomer. The construct depicted in FIG. 10. has three Fc domains including two associated polypeptides. Each of the two polypeptides contains three Fc domain monomers joined in a tandem series.

In another aspect, the disclosure features compositions and methods for promoting selective dimerization of Fc domain monomers. The disclosure includes an Fc domain wherein the two Fc domain monomers of the Fc domain include identical mutations in at least two positions within the ring of charged residues at the interface between $C_H3$ antibody constant domains. The disclosure also includes a method of making such an Fc domain, including introducing complementary dimerization selectivity modules having identical mutations in two Fc domain monomer sequences in at least two positions within the ring of charged residues at the interface between $C_H3$ antibody constant domains. The interface between $C_H3$ antibody constant domains consists of a hydrophobic patch surrounded by a ring of charged residues. When one $C_H3$ antibody constant domain comes together with another, these charged residues pair with residues of the opposite charge. By reversing the charge of both members of two or more complementary pairs of residues, mutated Fc domain monomers remain complementary to Fc domain monomers of the same mutated sequence, but have a lower complementarity to Fc domain monomers without those mutations. In this embodiment, the identical dimerization selectivity modules promotes homodimerization. Exemplary Fc domains include Fc monomers containing the double mutants K409D/D339K, K392D/D399K, E357K/K370E, D356K/K439D, K409E/D339K, K392E/D399K, E357K/K370D, or D356K/K439E. In another embodiment, an Fc domain includes Fc monomers including quadruple mutants combining any pair of the double mutants, e.g., K409D/D399K/E357K/K370E. In another embodiment, in addition to the identical dimerization selectivity modules, the Fc domain monomers of the Fc domain include complementary dimerization selectivity modules having non-identical mutations that promote specific association (e.g., engineered cavity and protuberance). As a result, the two Fc domain monomers include two dimerization selectivity modules and remain complementary to each other, but have a decreased complementarity to other Fc domain monomers. This embodiment promotes heterodimerization between a cavity-containing Fc domain and a protuberance-containing Fc domain monomer. In one example, the identical mutations in charged pair residues of both Fc domain monomers are combined with a protuberance on one Fc domain monomer and a cavity on the other Fc domain monomer.

In another aspect, the disclosure features a method of reducing inflammation in a subject in need thereof. In another aspect, the disclosure features a method of promoting clearance of autoantibodies in a subject in need thereof. In another aspect, the disclosure features a method of suppressing antigen presentation in a subject in need thereof. In another aspect, the disclosure features a method of reducing the immune response in a subject in need thereof, e.g., reducing immune complex-based activation of the immune response in a subject in need thereof. These methods include administering to the subject an Fc construct or pharmaceutical composition described herein.

In another aspect, the disclosure features a method of treating an inflammatory or autoimmune or immune disease in a subject by administering to the subject an Fc construct or pharmaceutical composition described herein (e.g., any one of constructs 1-10 and 5*). Exemplary diseases include: rheumatoid arthritis (RA); systemic lupus erythematosus (SLE); ANCA-associated vasculitis; antiphospholipid antibody syndrome; autoimmune hemolytic anemia; chronic inflammatory demyelinating neuropathy; clearance of anti-allo in transplant, anti-self in GVHD, anti-replacement, IgG therapeutics, IgG paraproteins; dermatomyositis; Goodpasture's Syndrome; organ system-targeted type II hypersensitivity syndromes mediated through antibody-dependent cell-mediated cytotoxicity, e.g., Guillain Barre syndrome, CIDP, dermatomyositis, Felty's syndrome, antibody-mediated rejection, autoimmune thyroid disease, ulcerative colitis, autoimmune liver disease; idiopathic thrombocytopenia purpura; Myasthenia Gravis, neuromyelitis optica; pemphigus and other autoimmune blistering disorders; Sjogren's Syndrome; autoimmune cytopenias and other disorders mediated through antibody-dependent phagocytosis; other FcR-dependent inflammatory syndromes, e.g., synovitis, dermatomyositis, systemic vasculitis, glomerulitis and vasculitis.

In another aspect, the disclosure features an Fc construct or pharmaceutical composition described herein (e.g., any one of constructs 1-10 and 5*) for use in reducing inflammation in a subject in need thereof. In another aspect, the disclosure features an Fc construct or pharmaceutical composition described herein (e.g., any one of constructs 1-10 and 5*) for use in promoting clearance of autoantibodies in a subject in need thereof. In another aspect, the disclosure features an Fc construct or pharmaceutical composition described herein (e.g., any one of constructs 1-10 and 5*) for use in suppressing antigen presentation in a subject in need thereof. In another aspect, the disclosure features an Fc construct or pharmaceutical composition described herein (e.g., any one of constructs 1-10 and 5*) for use in reducing the immune response in a subject in need thereof, e.g., reducing immune complex-based activation of the immune response in a subject in need thereof.

In another aspect, the disclosure features an Fc construct or pharmaceutical composition described herein (e.g., any one of constructs 1-10 and 5*) for use in treating an inflammatory or autoimmune or immune disease in a subject. Exemplary diseases include: rheumatoid arthritis (RA); systemic lupus erythematosus (SLE); ANCA-associated vasculitis; antiphospholipid antibody syndrome; autoimmune hemolytic anemia; chronic inflammatory demyelinating neuropathy; clearance of anti-allo in transplant, anti-self in GVHD, anti-replacement, IgG therapeutics, IgG paraproteins; dermatomyositis; Goodpasture's Syndrome; organ system-targeted type II hypersensitivity syndromes mediated through antibody-dependent cell-mediated cytotoxicity, e.g., Guillain Barre syndrome, CIDP, dermatomyositis, Felty's syndrome, antibody-mediated rejection, autoimmune thyroid disease, ulcerative colitis, autoimmune liver disease; idiopathic thrombocytopenia purpura; Myasthenia Gravis, neuromyelitis optica; pemphigus and other autoimmune blistering disorders; Sjogren's Syndrome; autoimmune cytopenias and other disorders mediated through antibody-dependent phagocytosis; other FcR-dependent inflammatory syndromes, e.g., synovitis, dermatomyositis, systemic vasculitis, glomerulitis and vasculitis.

In any of the Fc constructs described herein, it is understood that the order of the Fc domain monomers is interchangeable. For example, in a polypeptide having the formula A-L-B, the carboxy terminus of A can be joined to the amino terminus of L, which in turn is joined at its carboxy terminus to the amino terminus of B. Alternatively, the carboxy terminus of B can be joined to the amino terminus of L, which in turn is joined at its carboxy terminus to the amino terminus of C. Both of these configurations are encompassed by the formula A-L-B.

In a related aspect, the disclosure features a host cell that expresses any one of the foregoing Fc constructs. The host cell includes polynucleotides encoding the polypeptides needed to assemble the Fc construct, wherein the polynucleotides are expressed in the host cell.

Definitions

As used herein, the term "Fc domain monomer" refers to a polypeptide chain that includes at least a hinge domain and second and third antibody constant domains ($C_H2$ and $C_H3$) or functional fragments thereof (e.g., fragments that that capable of (i) dimerizing with another Fc domain monomer to form an Fc domain, and (ii) binding to an Fc receptor. The Fc domain monomer can be any immunoglobulin antibody isotype, including IgG, IgE, IgM, IgA, or IgD. Additionally, the Fc domain monomer can be an IgG subtype (e.g., IgG1, IgG2a, IgG2b, IgG3, or IgG4). An Fc domain monomer does not include any portion of an immunoglobulin that is capable of acting as an antigen-recognition region, e.g., a variable domain or a complementarity determining region (CDR). Fc domain monomers can contain as many as ten changes from a wild-type Fc domain monomer sequence (e.g., 1-10, 1-8, 1-6, 1-4 amino acid substitutions, additions, or deletions) that alter the interaction between an Fc domain and an Fc receptor. Examples of suitable changes are known in the art.

As used herein, the term "Fc domain" refers to a dimer of two Fc domain monomers that is capable of binding an Fc receptor. In the wild-type Fc domain, the two Fc domain monomers dimerize by the interaction between the two $C_H3$ antibody constant domains, as well as one or more disulfide bonds that form between the hinge domains of the two dimerizing Fc domain monomers.

In the present disclosure, the term "Fc construct" refers to associated polypeptide chains forming between 2-10 Fc domains (e.g., 2, 3, 4, 5, 6, 7, 8, 9, or 10 Fc domains; 2-8 Fc domains, 2-6 Fc domains, 2-4 Fc domains, 2-3 Fc domains, 5-10 Fc domains, 5-8 Fc domains, or 5-6 Fc domains) as described herein. Fc constructs described herein can include Fc domain monomers that have the same or different sequences. For example, an Fc construct can have two Fc domains, one of which includes IgG1 or IgG1-derived Fc domain monomers, and a second which includes IgG2 or IgG2-derived Fc domain monomers. In another example, an Fc construct can have two Fc domains, one of which comprises a "protuberance-into-cavity pair" and a second which does not comprise a "protuberance-into-cavity pair." In the present disclosure, an Fc domain does not include a variable region of an antibody, e.g., $V_H$, $V_L$, CDR, or HVR. An Fc domain forms the minimum structure that binds to an Fc receptor, e.g., FcγRI, FcγRIIa, FcγRIIb, FcγRIIIa, FcγRIIIb, FcγRIV.

As used herein, the term "antibody constant domain" refers to a polypeptide that corresponds to a constant region domain of an antibody (e.g., a $C_L$ antibody constant domain, a $C_H1$ antibody constant domain, a $C_H2$ antibody constant domain, or a $C_H3$ antibody constant domain).

As used herein, the term "promote" means to encourage and to favor, e.g., to favor the formation of an Fc domain from two Fc domain monomers which have higher binding affinity for each other than for other, distinct Fc domain monomers. As is described herein, two Fc domain monomers that combine to form an Fc domain can have compatible amino acid modifications (e.g., engineered protuberances and engineered cavities) at the interface of their respective $C_H3$ antibody constant domains. The compatible amino acid modifications promote or favor the selective interaction of such Fc domain monomers with each other relative to with other Fc domain monomers which lack such amino acid modifications or with incompatible amino acid modifications. This occurs because, due to the amino acid modifications at the interface of the two interacting $C_H3$ antibody constant domains, the Fc domain monomers to have a higher affinity toward each other than to other Fc domain monomers lacking amino acid modifications.

As used herein, the term "a dimerization selectivity module" refers to a sequence of the Fc domain monomer that facilitates the favored pairing between two Fc domain monomers. "Complementary" dimerization selectivity modules are dimerization selectivity modules that promote or favor the selective interaction of two Fc domain monomers with each other. Complementary dimerization selectivity modules can have the same or different sequences. Exemplary complementary dimerization selectivity modules are described herein.

As used herein, the term "engineered cavity" refers to the substitution of at least one of the original amino acid residues in the $C_H3$ antibody constant domain with a different amino acid residue having a smaller side chain volume than the original amino acid residue, thus creating a three dimensional cavity in the $C_H3$ antibody constant domain. The term "original amino acid residue" refers to a naturally occurring amino acid residue encoded by the genetic code of a wild-type $C_H3$ antibody constant domain.

As used herein, the term "engineered protuberance" refers to the substitution of at least one of the original amino acid residues in the $C_H3$ antibody constant domain with a different amino acid residue having a larger side chain volume than the original amino acid residue, thus creating a three dimensional protuberance in the $C_H3$ antibody constant domain. The term "original amino acid residues" refers to naturally occurring amino acid residues encoded by the genetic code of a wild-type $C_H3$ antibody constant domain.

As used herein, the term "protuberance-into-cavity pair" describes an Fc domain including two Fc domain monomers, wherein the first Fc domain monomer includes an engineered cavity in its $C_H3$ antibody constant domain, while the second Fc domain monomer includes an engineered protuberance in its $C_H3$ antibody constant domain. In a protuberance-into-cavity pair, the engineered protuberance in the $C_H3$ antibody constant domain of the first Fc domain monomer is positioned such that it interacts with the engineered cavity of the $C_H3$ antibody constant domain of the second Fc domain monomer without significantly perturbing the normal association of the dimer at the inter-$C_H3$ antibody constant domain interface.

As used herein, the term "joined" is used to describe the combination or attachment of two or more elements, components, or protein domains, e.g., polypeptides, by means including chemical conjugation, recombinant means, and chemical bonds, e.g., disulfide bonds and amide bonds. For example, two single polypeptides can be joined to form one contiguous protein structure through chemical conjugation, a chemical bond, a peptide linker, or any other means of covalent linkage. In some embodiments, a first Fc domain monomer is joined to a second Fc domain monomer by way of a peptide linker, wherein the N-terminus of the peptide linker is joined to the C-terminus of the first Fc domain monomer through a chemical bond, e.g., a peptide bond, and the C-terminus of the peptide linker is joined to the N-terminus of the second Fc domain monomer through a chemical bond, e.g., a peptide bond. In other embodiments, the N-terminus of an albumin-binding peptide is joined to the C-terminus of the $C_H3$ antibody constant domain of an Fc domain monomer by way of a linker in the same fashion as mentioned above.

As used herein, the term "associated" is used to describe the interaction, e.g., hydrogen bonding, hydrophobic interaction, or ionic interaction, between polypeptides (or sequences within one single polypeptide) such that the polypeptides (or sequences within one single polypeptide) are positioned to form an Fc construct that has at least one Fc domain. For example, two polypeptides, each including one Fc domain monomer, can associate to form an Fc construct (e.g., as depicted in FIGS. 1-3). In some embodiments, three polypeptides, e.g., one polypeptide including two Fc domain monomers and two polypeptides each including one Fc domain monomer, associate to form an Fc construct that has two Fc domains (e.g., as is shown in FIGS. 4 and 6). In some embodiments, four polypeptides, e.g., two polypeptides each including two Fc domain monomers and two polypeptides each including one Fc domain monomer, associate to form an Fc construct that has three Fc domains (e.g., as depicted in FIG. 5). In other embodiments, 2n polypeptides, e.g., each polypeptide including an Fc domain monomer, an IgG $C_L$ antibody constant domain, and an IgG $C_H1$ antibody constant domain associate to form an Fc construct that has n Fc domains (as is depicted in FIG. 7B). The two polypeptides can associate through their respective Fc domain monomers, or through other components of the polypeptide. For example, in FIG. 7B, polypeptide 708 associates with polypeptide 706 through its Fc domain monomer and associates with polypeptide 710 through association of its $C_L$ domain associating with the $C_H1$ domain of polypeptide 710. The association between polypeptides does not include covalent interactions. For example, in FIG. 10, Fc monomer sequences 1014 and 1012 within a single polypeptide associate to form an Fc domain, as do Fc monomer sequences 1004 and 1006.

As used herein, the term "linker" refers to a linkage between two elements, e.g., protein domains. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence (e.g., a 3-200 amino acid, 3-150 amino acid, 3-100 amino acid, 3-60 amino acid, 3-50 amino acid, 3-40 amino acid, 3-30 amino acid, 3-20 amino acid, 3-10 amino acid, 3-8 amino acid, 3-5 amino acid, 4-30 amino acid, 5-30 amino acid, 6-30 amino acid, 8-30 amino acid, 10-20 amino acid, 10-30 amino acid, 12-30 amino acid, 14-30 amino acid, 20-30 amino acid, 15-25 amino acid, 15-30 amino acid, 18-22 amino acid, and 20-30 amino acid sequence) occurring between two polypeptides or polypeptide domains (e.g., Fc domain monomers) to provide space and/or flexibility between the two polypeptides or polypeptide domains. An amino acid spacer is part of the primary sequence of a polypeptide (e.g., joined to the spaced polypeptides or polypeptide domains via the polypeptide backbone). The formation of disulfide bonds, e.g., between two hinge regions or two Fc domain monomers that form an Fc domain, is not considered a linker.

As used herein, the term "cleavable linker" refers to a linker containing one or more elements that can be selectively cleaved, e.g., after a construct is formed, e.g., a cleavable linker includes a polypeptide sequence that can be selectively cleaved by a protease.

As used herein, the term "albumin-binding peptide" refers to an amino acid sequence of 12 to 16 amino acids that has affinity for and functions to bind serum albumin. An albumin-binding peptide can be of different origins, e.g., human, mouse, or rat. In some embodiments of the present disclosure, an albumin-binding peptide is fused to the C-terminus of an Fc domain monomer to increase the serum half-life of the Fc construct. An albumin-binding peptide can be fused, either directly or through a linker, to the N- or C-terminus of an Fc domain monomer.

As used herein, the term "multimer" refers to a molecule including at least two associated Fc constructs described herein.

As used herein, the term "polynucleotide" refers to an oligonucleotide, or nucleotide, and fragments or portions thereof, and to DNA or RNA of genomic or synthetic origin, which may be single- or double-stranded, and represent the sense or anti-sense strand. A single polynucleotide is translated into a single polypeptide.

As used herein, the term "polypeptide" describes a single polymer in which the monomers are amino acid residues which are joined together through amide bonds. A polypeptide is intended to encompass any amino acid sequence, either naturally occurring, recombinant, or synthetically produced.

As used herein, the term "amino acid positions" refers to the position numbers of amino acids in a protein or protein domain. The amino acid positions for antibody or Fc constructs are numbered using the Kabat numbering system (Kabat et al., *Sequences of Proteins of Immunological Interest*, National Institutes of Health, Bethesda, Md., ed 5, 1991).

As used herein, the term "amino acid modification" or refers to an alteration of an Fc domain polypeptide sequence that, compared with a reference sequence (e.g., a wild-type, unmutated, or unmodified Fc sequence) may have an effect on the pharmacokinetics (PK) and/or pharmacodynamics (PD) properties, serum half-life, effector functions (e.g., cell lysis (e.g., antibody-dependent cell-mediated toxicity (ADCC) and/or complement dependent cytotoxicity activity (CDC)), phagocytosis (e.g., antibody dependent cellular phagocytosis (ADCP) and/or complement-dependent cellular cytotoxicity (CDCC)), immune activation, and T-cell activation), affinity for Fc receptors (e.g., Fc-gamma receptors (FcγR) (e.g., FcγRI (CD64), FcγRIIA (CD32), FcγRIIB (CD32), FcγRIIIA (CD16a), and/or FcγRIIIB (CD16b)), Fc-alpha receptors (FcαR), Fc-epsilon receptors (FcεR), and/or to the neonatal Fc receptor (FcRn)), affinity for proteins involved in the compliment cascade (e.g., C1q), post-translational modifications (e.g., glycosylation, sialylation), aggregation properties (e.g., the ability to form dimers (e.g., homo- and/or heterodimers) and/or multimers), and the biophysical properties (e.g., alters the interaction between CH1 and CL, alters stability, and/or alters sensitivity to temperature and/or pH) of an Fc construct, and may promote improved efficacy of treatment of immunological and inflammatory diseases. An amino acid modification includes amino acid substitutions, deletions, and/or insertions. In some embodiments, an amino acid modification is the modification of a single amino acid. In other embodiment, the amino acid modification is the modification of multiple (e.g., more than one) amino acids. The amino acid modification may comprise a combination of amino acid substitutions, deletions, and/or insertions. Included in the description of amino acid modifications, are genetic (i.e., DNA and RNA) alterations such as point mutations (e.g., the exchange of a single nucleotide for another), insertions and deletions (e.g., the addition and/or removal of one or more nucleotides) of the nucleotide sequence that codes for an Fc polypeptide.

In certain embodiments, at least one (e.g., at least one, two, three, four, five, six, seven, eight, nine, or ten) Fc domain within an Fc construct includes an amino acid modification. In some instances, the at least one Fc domain includes one or more (e.g., two, three, four, five, six, seven, eight, nine, ten, or twenty or more) amino acid modifications. In some instances, the at least one Fc domain includes no more than sixteen amino acid modifications (e.g., no more than one, two, three, four, five, six, seven, eight, nine, ten, eleven, twelve, thirteen, fourteen, fifteen, or sixteen amino acid modifications). In some cases, the Fc domain monomer includes no more than ten amino acid modifications. In some cases, the Fc domain monomer includes no more than 12 amino acid modifications. In some cases, the Fc domain monomer includes no more than 14 amino acid modifications.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell). As described herein, a host cell is used to express one or more polypeptides encoding desired domains which can then combine to form a desired Fc construct.

As used herein, the term "pharmaceutical composition" refers to a medicinal or pharmaceutical formulation that contains an active ingredient as well as one or more excipients and diluents to enable the active ingredient suitable for the method of administration. The pharmaceutical composition of the present disclosure includes pharmaceutically acceptable components that are compatible with the Fc construct. The pharmaceutical composition is typically in aqueous form for intravenous or subcutaneous administration.

As used herein, a "substantially homogenous population" of polypeptides or of an Fc construct is one in which at least 85% of the polypeptides or Fc constructs in a composition (e.g., a pharmaceutical composition) have the same number of Fc domains and the same Fc domain structure. In various embodiments, at least 90%, 92%, 95%, 97%, 98%, 99%, or 99.5% of the polypeptides or Fc constructs in the composition are the same. Accordingly, a pharmaceutical composition comprising a substantially homogenous population of an Fc construct is one in which at least 85% of the Fc constructs in the composition have the same number of Fc domains and the same structure. A substantially homogenous population of an Fc construct does not include more than 10% (e.g., not more than 8%, 5%, 2%, or 1%) multimers or aggregates of the Fc construct.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present disclosure, the pharmaceutically acceptable carrier must provide adequate pharmaceutical stability to the Fc construct. The nature of the carrier differs with the mode of administration. For example, for oral administration, a solid carrier is preferred; for intravenous administration, an aqueous solution carrier (e.g., WFI, and/or a buffered solution) is generally used.

As used herein, "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount

DETAILED DESCRIPTION OF THE INVENTION

Figure 1:
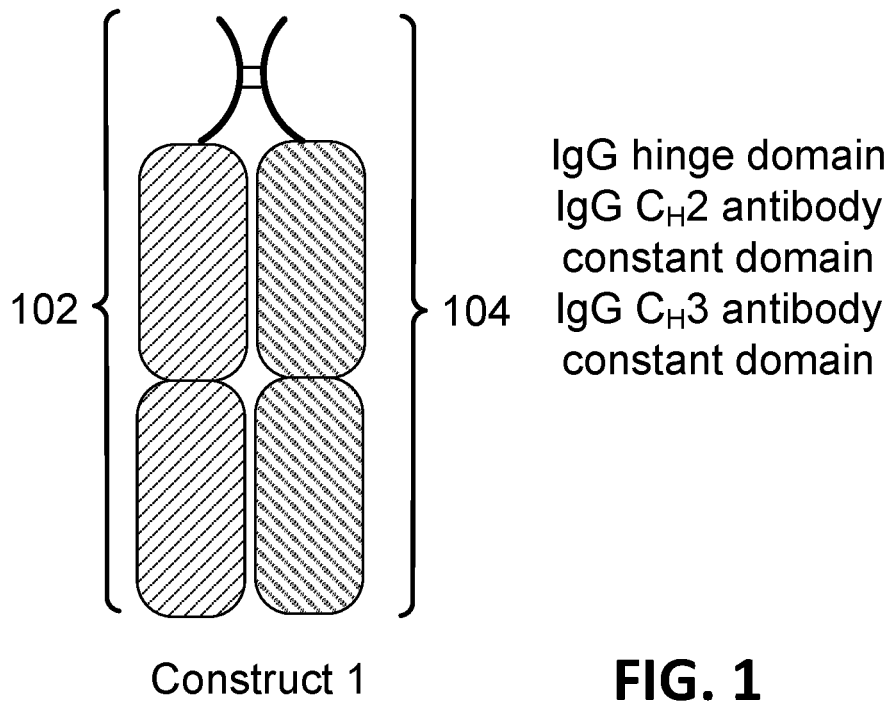
FIG. 1 is an illustration of an Fc construct (construct 1) containing a dimer of two wild-type (wt) Fc domain monomers (102 and 104).

Therapeutic proteins that include Fc domains of IgG can be used to treat inflammation and immunological and inflammatory diseases. The present disclosure features compositions and methods for preparing various Fc constructs containing two or more (e.g., 2-10) Fc domains.

I. Fc Domain Monomers

An Fc domain monomer includes a hinge domain, a $C_H2$ antibody constant domain, and a $C_H3$ antibody constant domain. The Fc domain monomer can be of immunoglobulin antibody isotype IgG, IgE, IgM, IgA, or IgD. The Fc domain monomer may also be of any immunoglobulin antibody isotype (e.g., IgG1, IgG2a, IgG2b, IgG3, or IgG4). A dimer of Fc domain monomers is an Fc domain (further defined herein) that can bind to an Fc receptor, e.g., FcγRIIIa, which is a receptor located on the surface of leukocytes. In the present disclosure, the $C_H3$ antibody constant domain of an Fc domain monomer may contain amino acid substitutions at the interface of the $C_H3$-$C_H3$ antibody constant domains to promote their association with each other. In some embodiments, an Fc domain monomer includes two other constant domains, e.g., $C_L$ and $C_H1$ antibody constant domains, attached to the N-terminus (FIG. 7). In other embodiments, an Fc domain monomer includes an additional moiety, e.g., an albumin-binding peptide, attached to the C-terminus. In the present disclosure, an Fc domain monomer does not contain any type of antibody variable region, e.g., $V_H$, $V_L$, a complementarity determining region (CDR), or a hypervariable region (HVR). The Fc domain monomer can be of different origins, e.g., human, mouse, or rat.

II. Fc Domains

As defined herein, an Fc domain includes two Fc domain monomers that are dimerized by the interaction between the $C_H3$ antibody constant domains. In the present disclosure, an Fc domain does not include a variable region of an antibody, e.g., $V_H$, $V_L$, CDR, or HVR. An Fc domain forms the minimum structure that binds to an Fc receptor, e.g., Fc-gamma receptors (i.e., Fcγ receptors (FcγR)), Fc-alpha receptors (i.e., Fcα receptors (FcαR)), Fc-epsilon receptors (i.e., Fcε receptors (FcεR)), and/or the neonatal Fc receptor (FcRn). In some embodiments, an Fc domain of the present disclosure binds to an Fcγ receptor (e.g., FcγRI (CD64), FcγRIIA (CD32), FcγRIIB (CD32), FcγRIIIA (CD16a), and/or FcγRIIIB (CD16b)) and/or the neonatal Fc receptor (FcRn).

III. Fc Domain Modifications

An unmodified Fc domain monomer can be a naturally occurring human Fc domain monomer or a WT human Fc domain monomer. An Fc domain monomer can be a naturally occurring human Fc domain monomer comprising a hinge, a $C_H2$ domain, and a $C_H3$ domain; or a variant thereof having up to 16 (e.g., up to 2, 3, 4, 5, 6, 7, 8, 9, 10, 11, 12, 13, 14, 15, or 16) amino acid modifications (e.g., single amino acid modifications) to accommodate or promote directed dimerization. In some cases, the Fc domain includes at least one amino acid modification, wherein the amino acid modifications alter one or more of (i) binding affinity to one or more Fc receptors, (ii) effector functions, (iii) the level of Fc domain sulfation, (iv) half-life, (v) protease resistance, (vi) Fc domain stability, and/or (vii) susceptibility to degradation (e.g., when compared to the unmodified Fc domain). In some cases, the Fc domain includes no more than 16 amino acid modifications (e.g., no more than 2, 3, 4, 5, 6, 7, 8, 9, 10, 11, 12, 13, 14, 15, or 16 amino acid modifications in the $C_H3$ domain).

The Fc domains of the disclosure include at least one (e.g., 1, 2, 3, 4, 5, 6, 7, 8, 9, 10, 20, 30, 40, 50, 60, 70, 80, 90, or 100) or more amino acid modifications at residues selected from positions 40, 92-103, 113-116, 118, 131, 137-146, 169-175, 196, 199, 203, 206, 211, 214, 217, 219-341, 344-346, 349-370, 372-374, 376-380, 382-405, 407-422, 424, 426-442, and/or 445-447. In some embodiments, the amino acid modification is an amino acid substitution, wherein the substituted amino acid is a natural or non-natural amino acid. In some embodiments, an amino acid modification is an amino acid deletion, wherein at least one (e.g., 1, 2, 3, 4, 5, 6, 7, 8, 9, 10, 20, 30, or 40) or more residues are deleted from the Fc domain. In some embodiments, an Fc domain modification is an amino acid insertion, wherein at least one (e.g., 1, 2, 3, 4, 5, 6, 7, 8, 9, 10, 20, 30, or 40) or more residues are inserted into the Fc domain. The amino acid modification can be a combination of multiple modifications, for example, a combination of one or more amino acid substitutions, deletions, and/or insertions.

Fc Receptor Binding Affinity

Amino acid modifications of the present disclosure may alter (i.e., increase or decrease) the binding affinity of an Fc domain to one (e.g., 1, 2, 3, 4, 5, or 6) or more Fc receptors (e.g., Fc-gamma receptors (FcγR), Fc-alpha receptors (FcαR), Fc-epsilon receptors (FcεR), and/or to the neonatal Fc receptor (FcRn)). A modified Fc domain may bind to an FcγR (e.g., FcγRI (CD64), FcγRIIA (CD32), FcγRIIB (CD32), FcγRIIIA (CD16a), and/or FcγRIIIB (CD16b)) and/or to the neonatal Fc receptor (FcRn) with an altered (i.e., increased or decreased) affinity as compared to an unmodified Fc domain. A modified Fc domain may have an altered (i.e., increased or decreased) dissociation constant (Kd) for one (e.g., 1, 2, 3, 4, 5, or 6) or more Fc receptors as compared to an unmodified Fc domain. Additionally, a modified Fc domain may have an altered (i.e., increased or decreased) level of glycosylation (e.g., glygan modification (e.g., mannose, sialic acids, fucose (Fuc), and/or galactose (Gal))) as compared to an unmodified Fc domain. An Fc modification may alter the affinity of an Fc domain to one (e.g., 1, 2, 3, 4, 5, or 6) or more Fc receptors, while inversely altering the affinity to at least one (e.g., 1, 2, 3, 4, 5, or 6) or more other Fc receptors.

Table 1 lists exemplary Fc domain residues that may be modified to alter Fc receptor binding affinity. In some embodiments, one (e.g., 1, 2, 3, 4, 5, 6, 7, 8, 9, 10, 20, 30, or 40) or more residues listed in Table 1 are modified, wherein the modified Fc domain has an altered binding affinity to an Fc receptor as compared to an unmodified Fc domain. In some embodiments, the Fc domain modification is an amino acid substitution occurring at one (e.g., 1, 2, 3, 4, 5, 6, 7, 8, 9, 10, 20, 30, or 40) or more residues listed in Table 1. In some embodiments, an Fc domain modification is an amino acid deletion occurring at one (e.g., 1, 2, 3, 4, 5, 6, 7, 8, 9, 10, 20, 30, or 40) or more residues listed in Table 1. In some embodiments, an Fc domain modification is an amino acid insertion occurring at one (e.g., 1, 2, 3, 4, 5, 6, 7, 8, 9, 10, 20, 30, or 40) or more residues listed in Table 1. The Fc domain modification can be a combination of multiple modifications, for example, the modification can comprise amino acid substitutions, deletions, and/or insertions.

Table 2 lists exemplary amino acid modifications that alter Fc domain binding affinity to Fc receptors. A modified Fc domain may include one (e.g., 1, 2, 3, 4, 5, 6, 7, 8, 9, 10, 20, 30, or 40) or more of the modifications listed in Table 2. In addition, modifications in Table 2 may be combined with modifications of any one (e.g., 1, 2, 3, 4, 5, 6, 7, 8, 9, 10, 20, 30, or 40) or more of the residues listed in Table 1.

An Fc domain modification may increase the affinity of a modified Fc domain binding to one (e.g., two, three, four, five, or six) or more Fc receptors by at least 1×, (e.g., 2×, 3×, 4×, 5×, 6×, 7×, 8×, 9×, 10×, 20×, 30×, 40×, 50×, 60×, 70×, 80×, 90×, 100×, 200×, 300×, 400×, 500×), as compared to an unmodified Fc domain. In some embodiments, an Fc domain modification increases binding affinity to an Fcγ receptor (e.g., FcγRI (CD64), FcγRIIA (CD32), FcγRIIB (CD32), FcγRIIIA (CD16a), and/or FcγRIIIB (CD16b)) and/or to the neonatal Fc receptor (FcRn). In some embodiments, an Fc domain modification increases binding affinity to FcγRIIIA (CD16a).

An Fc domain modification may decrease the affinity of a modified Fc domain binding to one (e.g., two, three, four, five, or six) or more Fc receptors by at least 1×, (e.g., 2×, 3×, 4×, 5×, 6×, 7×, 8×, 9×, 10×, 20×, 30×, 40×, 50×, 60×, 70×, 80×, 90×, 100×, 200×, 300×, 400×, 500×), as compared to an unmodified Fc domain. In some embodiments, an Fc domain modification decreases binding affinity to an Fcγ receptor (e.g., FcγRI (CD64), FcγRIIA (CD32), FcγRIIB (CD32), FcγRIIIA (CD16a), and/or FcγRIIIB (CD16b)) and/or to the neonatal Fc receptor (FcRn). In some embodiments, an Fc domain modification decreases binding affinity to FcγRIIB (CD32). In some embodiments, an Fc domain modification decreases binding affinity to FcRn.

Exemplary Fc domains with altered binding affinity to Fc receptors include Fc monomers containing the double mutants S267E/L328F. S267E/L328F mutations have been previously shown to significantly and specifically enhance IgG1 binding to the FcγRIIb receptor (Chu et al. Molecular Immunology. 2008 September; 45(15):3926-33).

TABLE 1

Fc domain residues that may be modified to alter Fc receptor binding affinity

Fc Domain Residues

| | | | | | | | |
|---|---|---|---|---|---|---|---|
| 92 | 172 | 240 | 272 | 304 | 336 | 376 | 413 |
| 93 | 173 | 241 | 273 | 305 | 337 | 377 | 414 |
| 94 | 174 | 242 | 274 | 306 | 338 | 378 | 415 |
| 95 | 175 | 243 | 275 | 307 | 339 | 379 | 416 |
| 96 | 196 | 244 | 276 | 308 | 340 | 380 | 417 |
| 97 | 199 | 245 | 277 | 309 | 341 | 382 | 418 |
| 98 | 203 | 246 | 278 | 310 | 343 | 383 | 419 |
| 99 | 206 | 247 | 279 | 311 | 344 | 384 | 420 |
| 100 | 211 | 248 | 280 | 312 | 345 | 385 | 421 |
| 101 | 214 | 249 | 281 | 313 | 346 | 386 | 422 |
| 102 | 217 | 250 | 282 | 314 | 350 | 387 | 424 |
| 103 | 219 | 251 | 283 | 315 | 351 | 388 | 426 |
| 113 | 220 | 252 | 284 | 316 | 352 | 389 | 427 |
| 114 | 221 | 253 | 285 | 317 | 353 | 390 | 428 |
| 115 | 222 | 254 | 286 | 318 | 354 | 391 | 429 |
| 116 | 223 | 255 | 287 | 319 | 355 | 392 | 430 |
| 118 | 224 | 256 | 288 | 320 | 356 | 393 | 431 |
| 131 | 225 | 257 | 289 | 321 | 357 | 394 | 432 |
| 133 | 226 | 258 | 290 | 322 | 358 | 396 | 433 |
| 137 | 227 | 259 | 291 | 323 | 359 | 397 | 434 |
| 138 | 228 | 260 | 292 | 324 | 360 | 398 | 435 |
| 139 | 229 | 261 | 293 | 325 | 361 | 399 | 436 |
| 140 | 230 | 262 | 294 | 326 | 362 | 400 | 437 |
| 141 | 231 | 263 | 295 | 327 | 363 | 401 | 438 |
| 142 | 232 | 264 | 296 | 328 | 365 | 402 | 439 |
| 143 | 233 | 265 | 297 | 329 | 366 | 404 | 440 |
| 144 | 234 | 266 | 298 | 330 | 367 | 405 | 441 |
| 145 | 235 | 267 | 299 | 331 | 369 | 408 | 442 |
| 146 | 236 | 268 | 300 | 332 | 370 | 409 | 445 |
| 169 | 237 | 269 | 301 | 333 | 372 | 410 | 446 |

TABLE 1-continued

Fc domain residues that may be modified to alter Fc receptor binding affinity

Fc Domain Residues

| | | | | | | |
|---|---|---|---|---|---|---|
| 170 | 238 | 270 | 302 | 334 | 373 | 411 | 447 |
| 171 | 239 | 271 | 303 | 335 | 374 | 412 | |

TABLE 2

Fc domain modifications altering Fc receptor binding affinity
Amino Acid Modifications

| | | |
|---|---|---|
| 100ins + A63A5: A85A5: A5: A42 | 250; 291 | 322; 299 |
| 101ins | 250; 299 | 323; 275 |
| 102ins | 250T; 251L; 252M; 253I; 254S | 323; 281 |
| 103ins | 250X; 314X | 323; 284 |
| 137ins | 250X; 314X; 428X | 323; 291 |
| 138ins | 250X; 428X | 323; 299 |
| 139ins | 252Y; 254T; 256E; 433K; 434F | 324; 275 |
| 140ins | 252Y; 254T; 256E; 433K; 434F; 436Y | 324; 281 |
| 141ins | 252Y; 254T; 256E; 433K; 434F; 446del | 324; 284 |
| 142ins | 252Y; 428L | 324; 291 |
| 143ins | 252Y; 434S | 324; 299 |
| 144ins | 255L; 396L | 325; 275 |
| 145ins | 256T; 257P | 325; 281 |
| 146ins | 258; 275 | 325; 284 |
| 169ins | 258; 281 | 325; 291 |
| 170ins | 258; 284 | 325; 299 |
| 171ins | 258; 291 | 325S; 326A; 327A; 328F |
| 172ins | 258; 299 | 325S; 326K; 327A; 328F |
| 173ins | 259I; 308F | 326; 275 |
| 174ins | 259I; 308F | 326; 281 |
| 175ins | 259I; 308F; 428L | 326; 284 |
| 235insA | 262; 275 | 326; 291 |
| 235insD | 262; 281 | 326; 299 |
| 235insG | 262; 284 | 326A; I332E; 333A |
| 235insL | 262; 291 | 326A; 333A |
| 235insN | 262; 299 | 327; 275 |
| 235insS | 263; 275 | 327; 281 |
| 235insT | 263; 281 | 327; 284 |
| 235insV | 263; 284 | 327; 291 |
| 254insN | 263; 291 | 327; 299 |
| 281insA | 263; 299 | 328; 275 |
| 281insD | 264; 275 | 328; 281 |
| 281insS | 264; 281 | 328; 284 |
| 281insT | 264; 284 | 328; 291 |
| 297insA | 264; 291 | 328; 299 |
| 297insD | 264; 299 | 328D; 332E |
| 297insG | 264E; 297D; 332E | 328E; 332E |
| 297insS | 264I; 298A; 332E | 328H; 332E |
| 326insA | 264I; 330L; 332E | 328I; 332E |
| 326insD | 264I; 330Y; 332E | 328M; 332E |
| 326insE | 264I; 332E | 328N; 332E |
| 326insG | 265; 275 | 328Q; 332E |
| 326insT | 265; 281 | 328R; 236insR |
| 92ins | 265; 284 | 328R; 236R |
| 93ins | 265; 291 | 328T; 332E |
| 94ins | 265; 299 | 328V; 332E |
| 95ins | 265A; 269A | 329; 275 |

TABLE 2-continued

| Fc domain modifications altering Fc receptor binding affinity Amino Acid Modifications | | |
|---|---|---|
| 96ins | 265F; 297E; 332E | 329; 281 |
| 97ins | 265X; 269X | 329; 284 |
| 98ins | 265X; 270X | 329; 291 |
| 99ins | 265X; 297X | 329; 299 |
| 281insA | 265X; 327X | 330; 275 |
| 281insD | 265Y; 297D; 299L; 332E | 330; 281 |
| 281insS | 265Y; 297D; 332E | 330; 284 |
| 281insT | 266; 275 | 330; 291 |
| 131C; 133R; 137E; 138S; 196K; 199T; 203D; 214R; 217S; 219Y; 220G; 221del; 222del; 223del; 224P; 233D; 237D; 238D; 268D; 271G; 296D; 330R; 439E | 266; 281 | 330; 299 |
| 221; 275 | 266; 284 | 330A; 331P; 339T |
| 221; 281 | 266; 291 | 330L; 332E |
| 221; 284 | 266; 299 | 330Y; 332E |
| 221; 291 | 267; 275 | 331; 275 |
| 221; 299 | 267; 281 | 331; 281 |
| 221del; 222del; 223del; 224del; 225del; 252Y; 254T; 256E; 433K; 434F; 446del | 267; 284 | 331; 284 |
| 221E; 270E; 308A; 311H; 396L; 402D | 267; 291 | 331; 291 |
| 222; 275 | 267; 299 | 331; 299 |
| 222; 281 | 267; 328 | 332; 275 |
| 222; 284 | 267E; 268F; 324T; I332E | 332; 281 |
| 222; 291 | 267E; 268F; 324T; 332E | 332; 284 |
| 222; 299 | 267E; 328F | 332; 291 |
| 223; 275 | 267E; 332E | 332; 299 |
| 223; 281 | 267L; 327S | 332X; 221X |
| 223; 284 | 267Q; 327S | 332X; 222X |
| 223; 291 | 268; 275 | 332X; 223X |
| 223; 299 | 268; 281 | 332X; 224X |
| 224; 275 | 268; 284 | 332X; 227X |
| 224; 281 | 268; 291 | 332X; 228X |
| 224; 284 | 268; 299 | 332X; 230X |
| 224; 291 | 268F; 324T; I332E | 332X; 231X |
| 224; 299 | 268F; 324T; 332E | 332X; 233X |
| 227; 275 | 268H; 355R; 419Q; 434N | 332X; 234X |
| 227; 281 | 268H; 355R; 419Q; 434N; 131C; 133R; 137E; 138S; 220C | 332X; 235X |
| 227; 284 | 268N; 396L | 332X; 236X |
| 227; 291 | 268P; 294K; 361S; 382V; 428L | 332X; 237X |

TABLE 2-continued

| Fc domain modifications altering Fc receptor binding affinity Amino Acid Modifications | | |
|---|---|---|
| 227; 299 | 268Q; 309L; 330S; 331S | 332X; 238X |
| 228; 275 | 269; 275 | 332X; 239X |
| 228; 281 | 269; 281 | 332X; 240X |
| 228; 284 | 269; 284 | 332X; 241X |
| 228; 291 | 269; 291 | 332X; 243X |
| 228; 299 | 269; 299 | 332X; 244X |
| 230; 275 | 269X; 270X | 332X; 245X |
| 230; 281 | 269X; 297X | 332X; 246X |
| 230; 284 | 269X; 327X | 332X; 247X |
| 230; 291 | 270 | 332X; 249X |
| 230; 299 | 270E | 332X; 250X |
| 231; 275 | 270; 275 | 332X; 258X |
| 231; 281 | 270; 281 | 332X; 262X |
| 231; 284 | 270; 284 | 332X; 263X |
| 231; 291 | 270; 291 | 332X; 264X |
| 231; 299 | 270; 299 | 332X; 265X |
| 233; 275 | 270X; 297X | 332X; 266X |
| 233; 281 | 270X; 327X | 332X; 268X |
| 233; 284 | 271; 275 | 332X; 269X |
| 233; 291 | 271; 281 | 332X; 270X |
| 233; 299 | 271; 284 | 332X; 271X |
| 233D; 237D; 238D; 264I; 267A; 268E; 271G; 272D; 296D; 439E | 271; 291 | 332X; 272X |
| 233D; 237D; 238D; 264I; 267A; 268E; 271G; 272P; 330R; 439E | 271; 299 | 332X; 273X |
| 233D; 237D; 238D; 264I; 267A; 268E; 271G; 296D; 327G; 330R; 396M; 439E | 272; 275 | 332X; 274X |
| 233D; 237D; 238D; 264I; 267A; 268E; 271G; 296D; 330R; 396L; 439E | 272; 281 | 332X; 275X |
| 233D; 237D; 238D; 264I; 267A; 268E; 271G; 296D; 330R; 396M; 439E | 272; 284 | 332X; 276X |
| 233D; 237D; 238D; 264I; 267A; 268E; 271G; 296D; 330R; 439E | 272; 291 | 332X; 278X |
| 233D; 237D; 238D; 264I; 267A; 268E; 271G; 330R; 396L; 439E | 272; 299 | 332X; 280X |
| 233D; 237D; 238D; 264I; 267A; 268E; | 273; 275 | 332X; 281X |

TABLE 2-continued

Fc domain modifications altering Fc receptor binding affinity
Amino Acid Modifications

| | | |
|---|---|---|
| 271G; 330R; 396M; 439E | | |
| 233D; 237D; 238D; 264I; 267A; 268E; 271G; 330R; 439E | 273; 281 | 332; 283X |
| 233D; 237D; 238D; 264I; 267A; 268E; 271G; 439E | 273; 284 | 332X; 285X |
| 233D; 237D; 238D; 264I; 267G; 268E; 271G; 330R; 439E | 273; 291 | 332X; 286X |
| 233D; 237D; 238D; 267A; 268E; 271G; 296D; 330R; 332T; 439E | 273; 299 | 332X; 288X |
| 233D; 237D; 238D; 268D; 271G; 296D; 327G; 330R; 439E | 274; 275 | 332X; 290X |
| 233D; 237D; 238D; 268D; 271G; 296D; 330R; 332T; 439E | 274; 281 | 332X; 291X |
| 233D; 237D; 238D; 268D; 271G; 296D; 330R; 439E | 274; 284 | 332X; 293X |
| 233D; 238D; 264I; 267A; 268E; 271G | 274; 291 | 332X; 294X |
| 233D; 238D; 264I; 267A; 268E; 271G; 296D; 439E | 274; 299 | 332X; 295X |
| 233P; 234A; 235A; 237A; 238P | 275; 275 | 332X; 296X |
| 233P; 234A; 235A; 237A; 238S | 275; 281 | 332X; 297X |
| 233P; 234V; 235A; 236del | 275; 284 | 332X; 298X |
| 233S; 234A; 235A; 237A; 238S | 275; 291 | 332X; 299X |
| 234; 275 | 275; 299 | 332X; 300X |
| 234; 281 | 276; 275 | 332X; 302X |
| 234; 284 | 276; 281 | 332X; 313X |
| 234; 291 | 276; 284 | 332X; 317X |
| 234; 299 | 276; 291 | 332X; 318X |
| 234A; 237A; 238S; 268A; 309L; 330S; 331S | 276; 299 | 332X; 320X |
| 234F; 235L; 409R | 278; 275 | 332X; 322X |
| 234L; 235L; 297N | 278; 281 | 332X; 323X |
| 234L; 235L; 297N; 327A; 330A; 331P | 278; 284 | 332X; 324X |
| 234L; 235L; 327A; 330A; 331P | 278; 291 | 332X; 325X |
| 234L; 235L; 327A; 330A; 331P; 268H; 274L; 355R; 356D; 358L; 419Q | 278; 299 | 332X; 326X |
| 234L; 235L; 327A; 330A; 331P; 434N | 280; 275 | 332X; 327X |
| 234V; 237G; 297N | 280; 281 | 332X; 328X |
| 234V; 237G; 330A | 280; 284 | 332X; 329X |
| 234V; 237G; 330A; 331P; 339T; 297N | 280; 291 | 332X; 330X |
| 235; 275 | 280; 299 | 332X; 331X |
| 235; 281 | 281; 275 | 332X; 333X |
| 235; 284 | 281; 281 | 332X; 334X |
| 235; 291 | 281; 284 | 332X; 335X |
| 235; 299 | 281; 291 | 332X; 336X |
| 236; 275 | 281; 299 | 332X; 428X |
| 236; 281 | 283; 275 | 333; 275 |
| 236; 284 | 283; 281 | 333; 281 |
| 236; 291 | 283; 284 | 333; 284 |
| 236; 299 | 283; 291 | 333; 291 |
| 236A; 239D | 283; 299 | 333; 299 |
| 236N; 267E | 284M; 298N; 334E; 355W; 416T | 334; 275 |
| 236S; 239D | 285; 275 | 334; 281 |
| 237; 275 | 285; 281 | 334; 284 |
| 237; 281 | 285; 284 | 334; 291 |
| 237; 284 | 285; 291 | 334; 299 |
| 237; 291 | 285; 299 | 334E; 292L |
| 237; 299 | 286; 275 | 335; 275 |
| 237A; 239D; I332E | 286; 281 | 335; 281 |
| 237A; 239D; 332E | 286; 284 | 335; 284 |
| 237D; 238D; 264I; 267A; 268E; 271G; 272P; 296D; 330R; 439E | 286; 291 | 335; 291 |
| 237D; 238D; 264I; 267A; 268E; 271G; 296D; 330R; 439E | 286; 299 | 335; 299 |
| 237D; 238D; 264I; 267A; 268E; 271G; 296D; 330R; 332T; 439E | 288; 275 | 336; 275 |
| 237D; 238D; 267A; 268E; 271G; 296D; 330R; 332T; 439E | 288; 281 | 336; 281 |
| 237D; 238D; 267A; 268E; 271G; 296D; 330R; 439E | 288; 284 | 336; 284 |
| 237D; 238D; 267G; 268D; 271G; 296D; 330R; 439E | 288; 291 | 336; 291 |
| 237D; 238D; 267G; 268E; 271G; 296D; 330R; 439E | 288; 299 | 336; 299 |
| 237D; 238D; 268D; 271G; 296D; 330R; 439E | 288M; 334E | 370E; 396L |
| 237D; 238D; 268E; 271G; 296D; 330R; 439E | 288N; 330S; 396L | 378T; 226G |
| 237D; 239D; I332E | 290; 275 | 378T; 230L |

TABLE 2-continued

Fc domain modifications altering Fc receptor binding affinity
Amino Acid Modifications

| | | | | | |
|---|---|---|---|---|---|
| 237D; 239D; 332E | 290; 281 | 378T; 230S | | 239D; 265L; 297D; 332E | 297; 284 | 428L; 308F |
| 237P; 239D; I332E | 290; 284 | 378T; 230T | | 239D; 265T; 297D; 332E | 297; 291 | 428L; 434S |
| 237P; 239D; 332E | 290; 291 | 378T; 241L | | 239D; 265V; 297D; 332E | 297; 299 | 428L; 434X |
| 237Q; 239D; I332E | 290; 299 | 378T; 264E | | 239D; 265Y; 297D; 332E | 297D; 298A; 330Y; 332E | 434S; 226G |
| 237Q; 239D; 332E | 291; 275 | 378T; 307P | | 239D; 268F; 324T; I332E | 297D; 299E; 332E | 434S; 230L |
| 237S; 239D; I332E | 291; 281 | 378T; 315D | | 239D; 268F; 324T; 332E | 297D; 299F; 332E | 434S; 230S |
| 237S; 239D; 332E | 291; 284 | 378T; 330V | | 239D; 297D; 332E | 297D; 299H; 332E | 434S; 230T |
| 238 | 291; 291 | 378T; 362R | | 239D; 298A; 332E | 297D; 299I; 332E | 434S; 241L |
| 238; 271 | 291; 299 | 378T; 389K | | 239D; 326A; 333A | 297D; 299L; 332E | 434S; 264E |
| 238; 275 | 292; 305 | 378T; 389T | | 239D; 330L; 332E | 297D; 299V; 332E | 434S; 307P |
| 238; 281 | 292P | 378T; 434S | | 239D; 330Y; 332E | 297D; 330Y; 332E | 434S; 311I |
| 238; 284 | 292P; 305I | 378T; 434Y | | 239D; 332D | 297D; 332E | 434S; 311V |
| 238; 291 | 293; 275 | 378T; P228L | | 239D; 332E | 297E; 332E | 434S; 315D |
| 238; 299 | 293; 281 | 378T; P228R | | 239D; 332E; 330L | 297N; 298X; 299S | 434S; 330V |
| 238; 271; 233; 330 | 293; 284 | 378V; 226G | | 239D; 332N | 297N; 298X; 299T | 434S; 362R |
| 238; 271; 237; 330 | 293; 291 | 378V; 230L | | 239D; 332Q | 297S; 332E | 434S; 378T |
| 238; 271; 237; 268 | 293; 299 | 378V; 230S | | 239E; 264I; 298A; 330Y; 332E | 297X; 327X | 434S; 378V |
| 238; 271; 237; 268; 330 | 293del; 294del | 378V; 230T | | | | |
| 238D | 293V; 295E | 378V; 241L | | 239E; 264I; 330Y; 332E | 298; 275 | 434S; 389K |
| 238D; 271G | 294; 275 | 378V; 264E | | 239E; 264I; 332E | 298; 281 | 434S; 389T |
| 238D; 271G; 233D; 330R | 294; 281 | 378V; 307P | | 239E; 265G | 298; 284 | 434S; 436I |
| 238D; 271G; 237D; 330R | 294; 284 | 378V; 315D | | 239E; 265N | 298; 291 | 434S; 436V |
| 238D; 271G; 237D; 268D | 294; 291 | 378V; 330V | | 239E; 265Q | 298; 299 | 434S; P228L |
| 238D; 271G; 237D; 268D; 330R | 294; 299 | 378V; 362R | | 239E; 297D; 332E | 298A; 332E | 434S; P228R |
| 238D; 264I; 267A; 268E; 271G | 295; 275 | 378V; 389K | | 239E; 332D | 298G; 299A | 434Y; 226G |
| 238D; 264I; 267A; 268E; 271G; 272D; 296D; 439E | 295; 281 | 378V; 389T | | 239E; 332E | 298X; 299X; 268X; 294X; 361X; 382X; 428X | 434Y; 230L |
| 238D; 264I; 267A; 268E; 271G; 296D; 439E | 295; 284 | 378V; 434S | | 239E; 332N | 298X; 299X; 382X | 434Y; 230S |
| 238D; 264I; 267A; 268E; 271G; 439E | 295; 291 | 378V; 434Y | | 239E; 332Q | 298X; 299X; 382X; 263X | 434Y; 230T |
| 239; 275 | 295; 299 | 378V; P228L | | 239N; 298A; 332E | 298X; 299X; 382X; 390X; 428X | 434Y; 241L |
| 239; 281 | 296; 275 | 378V; P228R | | | | |
| 239; 284 | 296; 281 | 380X; 434X | | 239N; 330L; 332E | 298X; 299X; 392X; 382X; 397X; 428X | 434Y; 264E |
| 239; 291 | 296; 284 | 382X; 263E | | | | |
| 239; 299 | 296; 291 | 382V; 390D; 428L | | 239N; 330Y; 332E | 298X; 333X; 334X | 434Y; 307P |
| 239; 332 | 296; 299 | 392E; 382V; 397M; 428L | | 239N; 332D | 298X; 334X | 434Y; 315D |
| 239; 330; 332 | 296D; 297D; 332E | 392E; 396L | | 239N; 332E | 299; 275 | 434Y; 330V |
| 239D; I332E | 296E; 297D; 332E | 392T; 396L | | 239N; 332N | 299; 281 | 434Y; 362R |
| 239D; 264I; 298A; 332E | 296H; 297D; 332E | 428; 275 | | 239N; 332Q | 299; 284 | 434Y; 378T |
| 239D; 264I; 330L; 332E | 296N; 297D; 332E | 428; 281 | | 239Q; 264I; 332E | 299; 291 | 434Y; 378V |
| 239D; 264I; 332E | 296Q; 297D; 332E | 428; 284 | | 239Q; 332D | 299; 299 | 434Y; 389K |
| 239D; 265F; 297D; 332E | 296T; 297D; 332E | 428; 291 | | 239Q; 332E | 300; 275 | 434Y; 389T |
| 239D; 265H; 297D; 332E | 297; 275 | 428; 299 | | 239Q; 332N | 300; 281 | 434Y; P228L |
| 239D; 265I; 297D; 332E | 297; 281 | 428L; 252X | | 239Q; 332Q | 300; 284 | 434Y; P228R |
| | | | | 240; 275 | 300; 291 | 436I; 434S |
| | | | | 240; 281 | 300; 299 | 436I; 428L |
| | | | | 240; 284 | 302; 275 | 436I; 434S |
| | | | | 240; 291 | 302; 281 | 436V; 428L |
| | | | | 240; 299 | 302; 284 | 436V; 434S |
| | | | | 241; 275 | 302; 291 | A330S; P331S; T339A |
| | | | | 241; 281 | 302; 299 | D265Y; N297D; T299L; I332E |
| | | | | 241; 284 | 304D; 290D | F234A; L235A; R409L |
| | | | | 241; 291 | 304D; 284D | F241E; F243Q; V262T; V264E |

TABLE 2-continued

Fc domain modifications altering Fc receptor binding affinity
Amino Acid Modifications

| | | |
|---|---|---|
| 241; 299 | 304D; 284E | F241E; F243Q; V262T; V264E; I332E |
| 241E; 243R1262E; 264R; 332E | 304D; 285D | F241E; F243R; V262E; V264R |
| 241E; 243Q; 262T; 264E | 304D; 285E | F241E; F243R; V262E; V264R; I332E |
| 241E; 243Q; 262T; 264E; 332E | 304D; 286D | F241E; F243Y; V262T; V264R |
| 241E; 243R; 262E; 264R | 304D; 286E | F241E; F243Y; V262T; V264R; I332E |
| 241E; 243Y; 262T; 264R | 304D; 288D | |
| 241E; 243Y; 262T; 264R; 332E | 304D; 288E | F241L; F243L; V262I; V264I |
| 241L; 243L; 262I; 264I | 304D; 290E | F241L; V262I |
| 241L; 262I | 304D; 305D | F241R; F243Q; V262T; V264R |
| 241R; 243Q; 262T; 264R | 304D; 305E | F241R; F243Q; V262T; V264R; I332E |
| 241R; 243Q; 262T; 264R; 332E | 304E; 284D | F241W; F243W; V262A; V264A |
| 241W; 243W | 304E; 284E | F241Y; F243Y; V262T; V264T |
| 241W; 243W; 262A; 264A | 304E; 285D | F241Y; F243Y; V262T; V264T; N297D; I332E |
| 241Y; 243Y; 262T; 264T | 304E; 285E | F243L; V262I; V264W |
| 241Y; 243Y; 262T; 264T; 297D; 332E | 304E; 286D | R292P |
| 243; 275 | 304E; 286E | F243L; R292P |
| 243; 281 | 304E; 288D | F243L; R292P; Y300L |
| 243; 284 | 304E; 288E | F243L; R292P; P396L |
| 243; 291 | 304E; 290D | H268G; R355Q; Q419E; N434A |
| 243; 292 | 304E; 290E | H268Q; R355Q; Q419E; N434A; C131S; R133K; E137G; S138G; C220S D270E |
| 243; 299 | 304E; 305D | |
| 243; 292; 300 | 304E; 305E | H433K; N434F |
| 243; 292; 396 | 305I; 292P | K326I; A327E; L328A |
| 243I; 379L | V305I; R292P | K326I; A327Y; L328G |
| 243I; 379L; 420V | 306L; 307T; 308V; 309L; 310H; 311Q; 312D | L234A; L235A; A327G; A330S; P331S |
| 243L; 255L | 307Q; 434S | L234A; L235A; A327G; A330S; P331S; H268Q; K274Q; R355Q; D356E; L358M; Q419E |
| 243L; 262I; 264W | 307X; 380X | L234A; L235A; A327G; A330S; P331S; N434A |
| 243L; 264I | 307X; 380X; 434X | L234A; L235A; N297A; |
| 243L; 292P | 307X; 434X | L234A; L235A; N297A; A327G; A330S; P331S |
| 243L; 292P; 300L | 311I; 434S | L234A; L235D; A327G; A330S; P331S |
| 243L; 292P; 396L | 311V; 434S | K267E; L328F |
| 243L; 292P; 300L; 305I; 396L | 313; 275 | S267E; L328F |
| 243L; 292P; 300L; 396L | 313; 281 | N297D; S298A |
| 243L; 305I; 378D; 404S; 396L | 313; 284 | N297D; S298T |
| 244; 275 | 313; 291 | N297D; T299E; I332E |
| 244; 281 | 313; 299 | N297D; T299F; I332E |
| 244; 284 | 314L; 315N; 316G | N297D; T299H; I332E |
| 244; 291 | 314X; 428X | N297D; T299I; I332E |
| 244; 299 | 315D; 382V; 428L | N297D; T299V; I332E |
| 244H; | 315I; 379M; | N297H; S298A |
| 245A; 247V | 399E | |
| 245; 275 | 316D; 378V; 399E | N315D; A330V; A378V; N434Y |
| 245; 281 | 317; 275 | N315D; A330V; N361D; A378V; N434Y |
| 245; 284 | 317; 281 | N315D; A378V; N434Y |
| 245; 291 | 317; 284 | N315D; K334E; A378V; N434Y |
| 245; 299 | 317; 291 | P113E; V114L; A115L; InG115/116; S118D; G206A; I211E |
| 246; 275 | 317; 299 | P228L; N315D; A330V; N361D; A378V; N434Y |
| 246; 281 | 318; 275 | P228L; P230S; N315D; A330V; N361D; A378V; N434Y |
| 246; 284 | 318; 281 | P228R; N315D; A330V; N361D; A378V; N434Y |
| 246; 291 | 318; 284 | P228R; P230S; N315D; A330V; N361D; A378V; N434Y |
| 246; 299 | 318; 291 | P230A; E233D |
| 247; 275 | 318; 299 | P230A; E233D; I332E |
| 247; 281 | 319F; 352L; 396L | P230S; N315D; A330V; N361D; A378V; N434Y |
| 247; 284 | 320; 275 | P230T; V264E; N315D; K370R; A378V |
| 247; 291 | 320; 281 | P244H; P245A; P247V |
| 247; 299 | 320; 284 | S239D; I332E |
| 248M; 247L; 420V | 320; 291 | S239D; A330L; I332E |
| 249; 275 | 320; 299 | S239D; N297D; I332E; A330Y; F241S; F243H; V262T; V264T |
| 249; 281 | 322; 275 | V234A; G237A; A330S; P331S; T339A |
| 249; 284 | 322; 281 | V234A; G237A; A330S; P331S; T339A; N297A |
| 249; 291 | 322; 284 | V234A; G237A; N297A |
| 249; 299 | 322; 291 | P238D |
| 250; 275 | 252Y; 254T; 256E | P238D; P271G |
| 250; 281 | V264E; N315D; A378V; N390S; G420R; N434Y | P238D; P271G; E233D; A330R |
| 250; 284 | V264E; N315D; A378V R292P; V305I | P238D; P271G; G237D; A330R; P238D; P271G; G237D; H268D; P238D; P271G; G237D; H268D; A330R | ins = insertion
del = deletion
X = any amino acid

Half-Life

Fc domain modifications that alter half-life may alter the binding of a modified Fc domain to FcRn, for example, by altering the affinity of the interaction at pH 6.0 and/or pH 7.4. Amino acid modifications that alter half-life may alter the pH dependence of the binding of and Fc domain to the FcRn receptor. Table 3 lists exemplary Fc domain residues that may be modified to alter the half-life (e.g., serum half-life) of Fc domains. In some embodiments, one (e.g., 1, 2, 3, 4, 5, 6, 7, 8, 9, 10, 20, 30, or 40) or more residues listed in Table 3 may be modified, wherein the modified Fc domain has an altered half-life as compared to an unmodified Fc domain. In some embodiments, the Fc domain modification is an amino acid substitution occurring at one (e.g., 1, 2, 3, 4, 5, 6, 7, 8, 9, 10, 20, 30, or 40) or more residues listed in Table 3. In some embodiments, an Fc domain modification is an amino acid deletion occurring at one (e.g., 1, 2, 3, 4, 5, 6, 7, 8, 9, 10, 20, 30, or 40) or more residues listed in Table 3. In some embodiments, an Fc domain modification is an amino acid insertion occurring at one (e.g., 1, 2, 3, 4, 5, 6, 7, 8, 9, 10, 20, 30, or 40) or more residues listed in Table 3. The Fc domain modification can be a combination of multiple modifications, for example, the modification can comprise amino acid substitutions, deletions, and/or insertions.

Table 4 lists exemplary modifications that alter Fc domain half-life. A modified Fc domain may include one (e.g., 1, 2, 3, 4, 5, 6, 7, 8, 9, 10, 20, 30, or 40) or more of the modifications listed in Table 4. In addition, modifications in Table 4 may be combined with modifications of residue positions listed in Table 3.

In some embodiments, an Fc domain modification may increase the half-life of a modified Fc domain at least 0.5×, (e.g., 1×, 2×, 3×, 4×, 5×, 6×, 7×, 8×, 9×, or 10×), as compared to an unmodified Fc domain.

In some embodiments, an Fc domain modification may decrease the half-life of a modified Fc domain by at least 0.5×, (e.g., 1×, 2×, 3×, 4×, 5×, 6×, 7×, 8×, 9×, or 10×), as compared to an unmodified Fc domain.

TABLE 3

Fc domain residues that may be modified to alter half-life

Fc Domain Residues

| | | | | | | |
|---|---|---|---|---|---|---|
| 92 | 141 | 248 | 282 | 314 | 380 | 436 |
| 93 | 142 | 249 | 284 | 315 | 383 | 438 |
| 94 | 143 | 250 | 285 | 316 | 385 | 446 |
| 95 | 144 | 251 | 286 | 317 | 386 | 447 |
| 96 | 145 | 252 | 287 | 322 | 387 | |
| 97 | 146 | 253 | 288 | 330 | 388 | |
| 98 | 169 | 254 | 289 | 331 | 389 | |
| 99 | 170 | 255 | 290 | 335 | 419 | |
| 100 | 171 | 256 | 304 | 339 | 424 | |
| 101 | 172 | 257 | 305 | 340 | 426 | |
| 102 | 173 | 258 | 306 | 343 | 428 | |
| 103 | 174 | 259 | 307 | 344 | 429 | |
| 131 | 175 | 260 | 308 | 345 | 430 | |
| 133 | 219 | 268 | 309 | 346 | 431 | |
| 137 | 220 | 277 | 310 | 355 | 432 | |
| 138 | 234 | 279 | 311 | 374 | 433 | |
| 139 | 235 | 280 | 312 | 376 | 434 | |
| 140 | 236 | 281 | 313 | 378 | 435 | |

TABLE 4

Fc domain modifications altering half-life
Amino Acid Modifications

| | | |
|---|---|---|
| 259I; 308F | 258N | 345T |
| 434S; 311I | 258Q | 345N |
| 434S; 311V | 279R | 345Q |
| 434S; 436I | 279H | 376S |
| 434S; 436V | 279K | 376T |
| H433K; N434F | 279D | 376N |
| 428L; 434S | 279E | 376Q |
| C131X; R133X; C220X; E137X; S138X; H268X; R355X; Q419X | 280R | 376R |
| C131X; R133X; C220X; E137X; S138X; H268X; R355X; Q419X; G446del; 447Kdel | 280H | 376H |
| C131X; R133X; C220X; E137X; S138X; H268X; R355X; Q419X; A330X; P331X; T339X | 280D | 376K |
| C131X; R133X; C220X; E137X; S138X; H268X; R355X; Q419X; A330X; P331X; T339X; G446del; K447del | 280E | 376D |
| C219X; C220X | 281R | 376E |
| C219X; C220X; H268X; R355X; Q419X | 281H | 378S |
| C219X; C220X; H268X; R355X; Q419X; G446del; K447del | 281K | 383R |
| C219X; C220X; G446del; K447del | 281D | 383H |
| C219S; C220S | 281E | 383K |

TABLE 4-continued

Fc domain modifications altering half-life
Amino Acid Modifications

| | | |
|---|---|---|
| C219X; C220X; H268X; R355X; Q419X | 282R | 383D |
| C219S; C220S; H268X; R355X; Q419X | 282H | 383E |
| C219S; C220S; H268Q; R355Q; Q419E | 282D | 385R |
| C219X; C220X; H268X; R355X; Q419X; G446del; K447del | 282E | 385H |
| C219S; C220S; G446del; K447del | 284S | 385K |
| C219S; C220S; H268X; R355X; Q419X; G446del; K447del | 284T | 385D |
| C219S; C220S; H268Q; R355Q; Q419E; G446del; K447del | 284N | 385E |
| 428L | 284Q | 389D |
| 434S | 284R | 389E |
| 251del | 284H | 424R |
| 253del | 284D | 424H |
| 255del | 284E | 424K |
| 285del | 285R | 424D |
| 286del | 285H | 424E |
| 287del | 285K | 426R |
| 288del | 285D | 426H |
| 289del | 285S | 426K |
| 290del | 285T | 426D |
| 308del | 285N | 426E |
| 309del | 285Q | 430R |
| 310del | 286E | 430H |
| 322del | 286T | 430D |
| 312del | 286M | 430E |
| 313del | 287S | 430S |
| 314del | 287T | 430T |
| 385del | 287N | 430N |
| 386del | 287Q | 430Q |
| 387del | 287R | 431R |
| 388del | 287H | 431H |
| 389del | 287K | 431K |
| 428del | 287D | 431D |
| 429del | 287E | 431E |
| 430del | 288R | 432S |
| 431del | 288H | 432T |
| 432del | 288K | 432N |
| 433del | 288D | 432Q |
| 434del | 288E | 434K |
| 435del | 304S | 434R |
| 436del | 304T | 434L |
| 251ins | 304N | 436D |
| 253ins | 304Q | 436E |
| 255ins | 304R | 438R |
| 285ins | 304H | 438H |
| 286ins | 304K | 438K |
| 287ins | 304D | 438D |
| 288ins | 304E | 438E |
| 289ins | 305S | 285E |
| 290ins | 305T | 286D |
| 308ins | 305N | 290E |
| 309ins | 305Q | 250R |
| 310ins | 305R | 250K |
| 322ins | 305H | 251R |
| 312ins | 305K | 251K |
| 313ins | 305D | 254S |
| 314ins | 305E | 255L |
| 385ins | 307S | 255D |
| 386ins | 307T | 255M |
| 387ins | 307N | 260K |
| 388ins | 307R | 257K |
| 389ins | 307H | 277R |
| 428ins | 307K | 277D |
| 429ins | 307D | 277Q |
| 430ins | 307E | 277K |
| 431ins | 308R | 281Q |
| 432ins | 308H | 282K |
| 433ins | 308K | 287P |
| 434ins | 308D | 285F |
| 435ins | 308E | 290D |
| 436ins | 309R | 306R |
| 435L | 309H | 306D |
| 252Y; 428L | 309K | 306E |
| 252Y; 434S | 309D | 306K |
| 428L; 252X | 309E | 310L |
| 428L; 434X | 310R | 374R |

TABLE 4-continued

Fc domain modifications altering half-life
Amino Acid Modifications

| | | |
|---|---|---|
| 433K; 434F; 436H | 310H | 374K |
| 255V | 310K | 374L |
| 309N | 310D | 428R |
| 312I | 310E | 428Q |
| 386L | 310S | 428K |
| 252Y | 310T | 431P |
| 252F | 310N | 432R |
| 252S | 310Q | 308F |
| 252W | 311R | 259I |
| 252T | 311H | 259I; 308F |
| 254T | 311K | 436I; 428L |
| 256S | 312R | 436I; 434S |
| 256R | 312H | 436V; 434S |
| 256Q | 312K | 436V; 428L |
| 256E | 312S | 259I; 308F; 428L |
| 256D | 312T | 436I; 434S |
| 309P | 312N | 252Y; 254T; 256E |
| 311S | 312Q | 308C |
| 311E | 313R | 308Y |
| 311L | 313H | 308W |
| 433R | 313K | 428L; 308F |
| 433S | 313D | 308P; 434A |
| 433I | 313E | 234F |
| 433P | 315R | 235A |
| 433Q | 315H | 235N |
| 434H | 315K | 235F |
| 434F | 315D | 235Q |
| 434Y | 315E | 235V |
| 251D | 316R | 322A |
| 251E | 316H | 322D |
| 307Q | 316K | 322E |
| 308P | 317R | 322H |
| 378V | 317H | 322N |
| 430A | 317K | 322Q |
| 430K | 317D | 331A |
| 434A | 317E | 331G |
| 436I | 317S | 92ins |
| 380A | 317T | 93ins |
| 250E | 317N | 94ins |
| 250Q | 317Q | 95ins |
| 428F | 340R | 96ins |
| 248R | 340H | 97ins |
| 248H | 340K | 98ins |
| 248K | 340D | 99ins |
| 248D | 340E | 100ins |
| 248E | 343R | 101ins |
| 249R | 343H | 102ins |
| 249K | 343K | 103ins |
| 251S | 343D | 137ins |
| 251T | 343E | 138ins |
| 251N | 343S | 139ins |
| 251Q | 343T | 140ins |
| 252N | 343N | 141ins |
| 252Q | 343Q | 142ins |
| 255S | 344L | 143ins |
| 255T | 345R | 144ins |
| 255N | 345H | 145ins |
| 255Q | 345K | 146ins |
| 256K | 345D | 169ins |
| 257R | 345E | 170ins |
| 257H | 345S | 171ins |
| 257D | 258T | 172ins |
| 257E | 175ins | 173ins |
| 258S | 174ins | 252Y; 254T; 256E; 433K; 434F; 436Y | ins = insertion
del = deletion
X = any amino acid

Effector Function

Table 5 lists exemplary Fc domain residues that may be modified to alter Fc domain effector function (e.g., cell lysis (e.g., antibody-dependent cell-mediated toxicity (ADCC) and/or complement dependent cytotoxicity activity (CDC)), phagocytosis (e.g., antibody dependent cellular phagocytosis (ADCP) and/or complement-dependent cellular cytotoxicity (CDCC)), immune activation, and T-cell activation). In some embodiments, one (e.g., 1, 2, 3, 4, 5, 6, 7, 8, 9, 10, 20, 30, or 40) or more residues listed in Table 5 may be modified, wherein the modified Fc domain has an altered effector function (e.g., ADCC, CDC, ADCP, CDCC, immune activation, and/or T-cell activation) as compared to an unmodified Fc domain. In some embodiments, the Fc domain modification is an amino acid substitution occurring at one (e.g., 1, 2, 3, 4, 5, 6, 7, 8, 9, 10, 20, 30, or 40) or more residues listed in Table 5. In some embodiments, an Fc domain modification is an amino acid deletion occurring at one (e.g., 1, 2, 3, 4, 5, 6, 7, 8, 9, 10, 20, 30, or 40) or more residues listed in Table 5. In some embodiments, an Fc modification is an amino acid insertion occurring at one (e.g., 1, 2, 3, 4, 5, 6, 7, 8, 9, 10, 20, 30, or 40) or more residues listed in Table 5.

Table 6 lists exemplary modifications that alter Fc domain effector function (e.g., ADCC, CDC, ADCP, CDCC, immune activation, and/or T-cell activation). A modified Fc domain may include one (e.g., 1, 2, 3, 4, 5, 6, 7, 8, 9, 10, 20, 30, or 40) or more of the modifications listed in Table 6. In addition, modifications in Table 6 may be combined with modifications of residues listed in Table 5.

An Fc domain modification may increase the effector function (e.g., ADCC, CDC, ADCP, CDCC, immune activation, and/or T-cell activation) of a modified Fc domain at least 0.5×, (e.g., 1×, 2×, 3×, 4×, 5×, 6×, 7×, 8×, 9×, or 10×), as compared to an unmodified Fc domain.

An Fc domain modification may decrease the effector functions (e.g., cell lysis (e.g., ADCC, CDC, ADCP, CDCC, immune activation, and/or T-cell activation) of a modified Fc domain by at least 0.5×, (e.g., 1×, 2×, 3×, 4×, 5×, 6×, 7×, 8×, 9×, or 10×), as compared to an unmodified Fc domain.

TABLE 5

Fc domain residues that may be modified to alter effector function
Fc Domain Residues

| | | | | | |
|---|---|---|---|---|---|
| 40 | 264 | 297 | 332 | 390 | 436 |
| 224 | 265 | 298 | 333 | 391 | 439 |
| 225 | 266 | 299 | 334 | 393 | 440 |
| 228 | 267 | 300 | 339 | 394 | 441 |
| 230 | 268 | 301 | 345 | 399 | 442 |
| 234 | 269 | 304 | 355 | 404 | 445 |
| 235 | 273 | 305 | 356 | 408 | 446 |
| 236 | 276 | 306 | 358 | 409 | 447 |
| 239 | 278 | 307 | 359 | 411 | |
| 240 | 279 | 309 | 361 | 412 | |
| 241 | 280 | 311 | 362 | 414 | |
| 243 | 283 | 312 | 365 | 421 | |
| 244 | 285 | 315 | 370 | 422 | |
| 246 | 288 | 320 | 372 | 426 | |
| 247 | 289 | 322 | 376 | 427 | |
| 251 | 290 | 323 | 377 | 428 | |
| 252 | 291 | 324 | 378 | 430 | |
| 253 | 292 | 325 | 382 | 431 | |
| 254 | 293 | 328 | 383 | 432 | |
| 258 | 294 | 329 | 386 | 433 | |
| 261 | 295 | 330 | 388 | 434 | |
| 262 | 296 | 331 | 389 | 435 | |

TABLE 6

Fc domain modifications altering effector function
Amino Acid Modifications

| | | |
|---|---|---|
| 224N | 301H | 411I |
| 224Y | 301K | 412A |
| 225A | 301N | 414M |
| 228L | 301Q | 421S |
| 228P; 235E | 301R | 422I |
| 230S | 301S | 426F |
| 234A; 235A | 301T | 426P |
| 234F | 304G | 427F |
| 235A | 305A | 428T |
| 235F | 306F | 430K |
| 235N | 306I | 431S |
| 235Q | 307P | 432P |
| 235V | 309K | 433P |
| 236A | 309M | 435A |
| 236R; 328R | 309P | 435G |
| 239D; 378F | 311R | 435N |
| 239D; 378G | 312N | 435Q |
| 239D; 378S | 315D | 435S |
| 239D; 378W | 315K | 435T |
| 239D; 378Y | 315S | 435Y |
| 239E; 378F | 320R | 439E |
| 239E; 378G | 322A | 439R |
| 239E; 378S | 322D | 440G |
| 239E; 378W | 322E | 441F |
| 239E; 378Y | 322H | 442T |
| 239P | 322N | 445R |
| 240A | 322Q | 446A |
| 241H | 323A | 447E |
| 241L | 323F | A330H |
| 241Q | 324T | A330L |
| 243G | 325A | A378F |
| 243H | 328D | A378K |
| 243I | 328G | A378T |
| 243L | 328K | A378W |
| 244L | 328T | D265E |
| 246E | 329G | D356 |
| 247A | 329R | E293D |
| 247L | 330H | E294S |
| 251A | 330L | E294T |
| 251F | 331A | E345 |
| 251G | 331G | E356 |
| 251I | 332D | E382 |
| 251L | 332D; 261A | E430 |
| 251M | 332D; 378F | F241H |
| 251P | 332D; 378K | F241Q |
| 251S | 332D; 378W | G236A |
| 251V | 332D; 378Y | H435A |
| 251W | 332D; 435G | H435G |
| 252S | 332D; 435S | H435S |
| 252T | 332E | I253 |
| 252W | 332K | I332D |
| 252Y | 332Q | I332E |
| 254P | 333X; 334X | I332K |
| 254T | 334R | I332Q |
| 258K | 355W | K334L |
| 261A | 356G | K334R |
| 261Y | 356W | K439D; S440H |
| 262L | 358T | K439D; S440K |
| 264T | 361D | K439D; S440R |
| 265D | 361Y | K439E; S440K |
| 265E | 362L | K447 |
| 265V | 364C | L251A |
| 266A | 365P | L251G |
| 266F | 365Q | L261A |
| 267G | 370R | L268P |
| 267N | 372L | N376F |
| 268D | 376C | N376H |
| 268E | 376D | N376K |
| 268N | 376E | N376R |
| 268P | 376F | N376W |
| 269G | 376H | N434A |
| 269K | 376K | N434F |
| 273A | 376N | N434H |
| 276D | 376Q | N434W |
| 278H | 376R | N434Y |
| 279M | 376S | P247 |
| 280N | 376T | Q311 |
| 283G | 376W | Q386 |
| 285R | 376Y | R301K |
| 288R | 377V | R301N |
| 289A | 378D | R301Q |
| 290E | 378E | R301S |
| 291L | 378F | R301T |
| 292Q | 378H | S239P |
| 293C | 378K | S254 |
| 293D | 378Q | S440W |
| 294C | 378R | S440Y |
| 294R | 378T | T299A; 297Z |
| 294S | 378W | T299C; 297Z |
| 294T | 378Y | T299C; N297Z |
| 295C | 383N | T299D; 297Z |
| 296C | 389S | T299E; 297Z |
| 297C | 390D | T299F; 297Z |
| 297D | 391C | T299G; 297Z |
| 297G; 356E; 358M | 393A | T299H; 297Z |
| 297Q | 394A | T299I; 297Z |
| 298C | 399G | T299K; 297Z |
| 298N; 300S | 399S | T299L; 297Z |
| 298N; 300T | 404S | T299M; 297Z |
| 298X; 333X | 408G | T299N; 297Z |
| 298X; 334X | 409R | T299P; 297Z |
| 299A | 40F | T299R; 297Z |
| 299K | 301E | T299V; 297Z |
| 300C | Y436 | T299W; 297Z |
| 300H | T359 | T299X; N297Z |
| 301C | 301D | T299Y; 297Z | ins = insertion
del = deletion
X = any amino acid

Alters Stability

Altering Fc domain stability can impact thermal stability (e.g., a melting temperature or Tm) and aggregate formation (e.g., aggregate formation under acidic, or low-pH, conditions).

In some embodiments, the thermal stability of a modified Fc domain may be altered (i.e., increased or decreased) by at least about 0.1° C. (e.g., about 0.25° C., about 0.5° C., about 0.75° C., about 1° C., about 1.25° C., about 1.5° C., about 1.75° C., about 2° C., about 3° C., about 4° C., about 5° C., about 6° C., about 7° C., about 8° C., about 9° C., about 10° C., about 20° C., about 30° C., about 40° C., or about 50° C.) or as compared to an unmodified Fc domain. In some embodiments, the thermal stability of a modified Fc domain is increased as compared to an unmodified Fc domain. In some embodiments, the thermal stability of a modified Fc domain is decreased as compared to an unmodified Fc domain. In certain embodiments, a modified Fc domain has altered (i.e., increased or decreased) aggregation properties of at least 1% (e.g., 2%, 3%, 4%, 5%, 6%, 7%, 8%, 9%, 10%, 20%, 30%, 40%, 50%, 60%, 70%, 80%, or 90%) or more as compared to an unmodified Fc domain. In some embodiments, the aggregation properties of a modified Fc domain are increased as compared to an unmodified Fc domain. In some embodiments, the aggregation properties are decreased as compared to an unmodified Fc domain.

Table 7 lists exemplary Fc domain residues that may be modified to alter Fc domain stability. In some embodiments, one (e.g., 1, 2, 3, 4, 5, 6, 7, 8, 9, 10, 20, 30, or 40) or more residues listed in Table 7 may be modified, wherein the modified Fc domain has an altered stability as compared to an unmodified Fc domain. In some embodiments, the Fc domain modification is an amino acid substitution occurring at one (e.g., 1, 2, 3, 4, 5, 6, 7, 8, 9, 10, 20, 30, or 40) or more residues listed in Table 7. In some embodiments, an Fc domain modification is an amino acid deletion occurring at one (e.g., 1, 2, 3, 4, 5, 6, 7, 8, 9, 10, 20, 30, or 40) or more residues listed in Table 7. In some embodiments, an Fc domain modification is an amino acid insertion occurring at one (e.g., 1, 2, 3, 4, 5, 6, 7, 8, 9, 10, 20, 30, or 40) or more residues listed in Table 7.

Table 8 lists exemplary modifications that alter Fc domain stability. A modified Fc domain may include one (e.g., 1, 2, 3, 4, 5, 6, 7, 8, 9, 10, 20, 30, or 40) or more of the modifications listed in Table 8. In addition, modifications in Table 8 may be combined with modifications of residues listed in Table 7.

An Fc domain modification may increase the stability of a modified Fc domain at least 0.5×, (e.g., 1×, 2×, 3×, 4×, 5×, 6×, 7×, 8×, 9×, or 10×), as compared to an unmodified Fc domain.

An Fc domain modification may decrease the stability of a modified Fc domain by at least 0.5×, (e.g., 1×, 2×, 3×, 4×, 5×, 6×, 7×, 8×, 9×, or 10×), as compared to an unmodified Fc domain.

TABLE 7

Fc domain residues that may be modified to alter stability
Fc Domain Residues

| 40  | 252 | 300 | 354 | 368 | 402 |
|-----|-----|-----|-----|-----|-----|
| 217 | 262 | 307 | 355 | 370 | 403 |
| 219 | 264 | 309 | 356 | 392 | 404 |
| 225 | 266 | 322 | 357 | 394 | 405 |
| 228 | 267 | 323 | 358 | 395 | 407 |
| 232 | 273 | 331 | 359 | 396 | 409 |
| 234 | 275 | 339 | 360 | 397 | 427 |
| 235 | 277 | 349 | 361 | 398 |     |
| 236 | 279 | 351 | 362 | 399 |     |
| 238 | 297 | 352 | 364 | 400 |     |
| 250 | 299 | 353 | 366 | 401 |     |

TABLE 8

Fc domain modifications altering stability
Amino Acid Modifications

| 217R | 228P; 235E | 273R | 359del | 235Q | 309L |
|------|------------|------|--------|------|------|
| 219N | 228P; 235E; 409K | 273Y | 360del | 235V | 309M |
| 219Q | 228P; 235E; 409L | 275F | 361del | 236S | 309P |
| 225I | 228P; 235E; 409M | 275K | 362del | 236T | 322A |
| 225T | 228P; 235E; 409T | 275Q | 392K | 238R | 322D |
| 225V | 228P; 235P | 277E | 397del | 250E | 322E |
| 228E | 228P; 235P; 409K | 279D | 397V | 250Q | 322H |
| 228E; 235E | 228P; 235P; 409L | 279N | 398del | 252S | 322N |
| 228E; 235E; 409K | 228P; 235P; 409M | 279V | 399del | 252T | 322Q |
| 228E; 235E; 409L | 228P; 235P; 409T | 297D | 399S | 252W | 323F |
| 228E; 235E; 409M | 232K | 297G; 356E; 358M | 400del | 252Y | 331A |
| 228E; 235E; 409T | 232R | 297Q | 401del | 262L | 331G |
| 228E; 235P | 234F | 299K | 402del | 264T | 339A |
| 228E; 235P; 409K | 234K | 300Y | 403del | 266F | 354del |
| 228E; 235P; 409L | 234N | 307P | 404del | 267S | 355del |
| 228E; 235P; 409M | 234R | 309K | 409K | 267T | 356del |
| 228E; 235P; 409T | 235A | 427F | 409L | 273K | 357del |
| 228P | 235E | 235P | 409M | 273Q |      |
| 235N | 235F | 409T | 40F | 358del |     | ins = insertion
del = deletion
X = any amino acid

Alters Susceptibility to Degradation

Susceptibility to degradation can impact how an Fc domain containing molecule can be stored and transported. Reducing an Fc domain's susceptibility to environmental conditions (e.g., temperature, humidity, pH), such as temperature, can make an Fc domain comprising molecule more readily transportable and/or storable over longer periods of time. Exemplary Fc residues that may be modified to alter Fc domain susceptibility to degradation include 233, 234, 235, 236, 237, 239, 241, and 249. In some embodiments, one (e.g., 1, 2, 3, 4, 5, 6, 7, or 8) residues selected from the group consisting of residues 233, 234, 235, 236, 237, 239, 241, and 249 may be modified, wherein the modified Fc domain has an altered susceptibility to degradation as compared to an unmodified Fc domain. In some embodiments, the Fc modification is an amino acid substitution occurring at one (e.g., 1, 2, 3, 4, 5, 6, 7, or 8) residue positions selected from the groups consisting of 233, 234, 235, 236, 237, 239, 241, and 249. In some embodiments, an Fc modification is an amino acid deletion occurring at one (e.g., 1, 2, 3, 4, 5, 6, 7, or 8) residue positions selected from the group consisting of 233, 234, 235, 236, 237, 239, 241, and 249. In some embodiments, an Fc modification is an amino acid insertion occurring at one (e.g., 1, 2, 3, 4, 5, 6, 7, or 8) residue positions selected from the group consisting of 233, 234, 235, 236, 237, 239, 241, and 249.

Exemplary modifications that alter Fc domain susceptibility to degradation may include one (e.g., 1, 2, 3, 4, 5, 6, 7, or 8) modifications selected from the group consisting of C233X, D234X, K235X, S236X, T236X, H237X, C239X, S241X, and G249X, in which X is any amino acid.

An Fc domain modification may decrease the degradation of a modified Fc domain by at least 1%, (e.g., 2%, 3%, 4%, 5%, 6%, 7%, 8%, 9%, 10%, 20%, 30%, 40%, 50%, 60%, 70%, 80%, or 90%) or more as compared to an unmodified Fc domain. In some embodiments, an Fc domain modification may decrease the degradation of a modified Fc domain upon heating by at least 1%, (e.g., 2%, 3%, 4%, 5%, 6%, 7%, 8%, 9%, 10%, 20%, 30%, 40%, 50%, 60%, 70%, 80%, or 90%) or more as compared to an unmodified Fc domain. In some embodiments, the Fc domain is heated over a period of at least one hour (e.g., 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, or 1 week) or more. In some embodiments, the temperature to which an Fc domain is heated is at least 45° C. (e.g., 50° C., 55° C., 60° C., 65° C., 70° C., 75° C., 85° C., or 95° C.) or higher. The level of degradation a modified Fc domain is susceptible to may be measured by assessing the degrees of aggregation, degradation, or fragmentation by methods known to those skilled in the art, including but not limited to reduced Capillary Gel Electrophoresis (rCGE), Sodium Dodecyl Sulfate Polyacrylamide Gel Electrophoresis (SDS-PAGE) and high performance size exclusion chromatography (HPSEC).

Sulfation

Exemplary Fc residues that may be modified to alter Fc domain sulfation include residues 241, 243, 246, 260, and 301. In some embodiments, one (e.g., 1, 2, 3, 4, or 5) Fc domain residues selected from the group consisting of 241, 243, 246, 260, and 301 may be modified, wherein the modified Fc domain has altered sulfation as compared to an unmodified Fc domain. In some embodiments, the Fc domain modification is an amino acid substitution occurring at one (e.g., 1, 2, 3, 4, or 5) residues selected from the group consisting of residues 241, 243, 246, 260, and 301. In some embodiments, an Fc domain modification is an amino acid deletion occurring at one (e.g., 1, 2, 3, 4, or 5) residues selected from the group consisting of residues 241, 243, 246, 260, and/or 301. In some embodiments, an Fc modification is an amino acid insertion occurring at one (e.g., 1, 2, 3, 4, or 5) residue positions selected from the group consisting of Fc domain residues 241, 243, 246, 260, and 301.

Exemplary modifications that alter Fc domain sulfation include 241F, 243F, 246K, 260T, and/or 301 R. A modified Fc domain may include one (e.g., 1, 2, 3, 4, or 5) modifications selected from the group consisting of 241F, 243F, 246K, 260T, and 301R. Any one of these modifications may be combined with additional modifications of residues 241, 243, 246, 260, and/or 301.

An Fc domain modification may increase the sulfation of a modified Fc domain at least 0.5×, (e.g., 1×, 2×, 3×, 4×, 5×, 6×, 7×, 8×, 9×, or 10×), as compared to an unmodified Fc domain.

An Fc domain modification may decrease the sulfation of a modified Fc domain by at least 0.5×, (e.g., 1×, 2×, 3×, 4×, 5×, 6×, 7×, 8×, 9×, or 10×), as compared to an unmodified Fc domain.

Protease Resistance

The Fc domain may be modified to increase protease resistance, for example, resistance to endosomal proteases, extracellular proteases (e.g., trypsin, chymotypsin, plasmin), digestive proteases (e.g., pepsin), serum proteases (e.g., clotting factors), proteases released from leukocytes (e.g., elastase and cathepsin G) and tissue-specific proteases (e.g., tumor-specific proteases (e.g. matrix metalloproteinases). Susceptibility to protease degradation can play an important role in regulating the half-life of an Fc domain, with increased susceptibility contributing to a shorter half-life and reduced susceptibility contributing to a longer half-life. To alter protease resistance, amino acid modifications of may be made within regions of the Fc domain that comprise or affect protease cleavage sites. Alternatively, amino acid modifications that alter the glycosylation state of the Fc domain may alter the protease resistance and/or susceptibility characteristics of an Fc domain.

Exemplary Fc residues that may be modified to alter protease resistance comprise 233, 234, 235, 236, 237, 239, 243, 267, 268, 292, 300, 324, 326, 332, and 333. In some embodiments, one (e.g., 1, 2, 3, 4, 5, 6, 7, 8, 9, 10, 11, 12, 13, 14, or 15) Fc domain residues selected from 233, 234, 235, 236, 237, 239, 243, 267, 268, 292, 300, 324, 326, 332, and 333 may be modified, wherein the modified Fc domain has an altered protease resistance as compared to an unmodified Fc domain. An Fc domain modification may be an amino acid substitution occurring at one (e.g., 1, 2, 3, 4, 5, 6, 7, 8, 9, 10, 11, 12, 13, 14, or 15) residues selected from residues 233, 234, 235, 236, 237, 239, 243, 267, 268, 292, 300, 324, 326, 332, and 333. An Fc modification may also be an amino acid deletion occurring at one (e.g., 1, 2, 3, 4, 5, 6, 7, 8, 9, 10, 11, 12, 13, 14, 15 or 16) residues selected from 233, 234, 235, 236, 237, 239, 243, 267, 268, 292, 300, 324, 326, 332, and 333. In some embodiments, an Fc modification is an amino acid insertion occurring at one (e.g., 1, 2, 3, 4, 5, 6, 7, 8, 9, 10, 11, 12, 13, 14, or 15) residue positions selected from 233, 234, 235, 236, 237, 239, 243, 267, 268, 292, 300, 324, 326, 332, and 333. In some embodiments, the Fc domain modification may be a combination of any one of the above (e.g., a combination of an amino acid substitution, deletion, and/or insertion).

Exemplary modifications that alter Fc domain protease resistance may comprise any one (e.g., 1, 2, 3, 4, 5, 6, 7, 8, 9, 10, 11, 12, 13, 14, or 15) of the following 233P, 234V, 235A, and 236del; 237A, 239D, and 332E; 237D, 239D, and 332E; 237P, 239D, and 332E; 237Q, 239D, and 332E; 237S, 239D, and 332E; 239D, 268F, 324T, and 332E; 239D, 326A, and 333A; 239D and 332E; 243L, 292P, and 300L; 267E, 268F, 324T, and 332E; 267E and 332E; 268F, 324T, and 332E; 326A, 332E, and 333A; and 326A and 333A.

An Fc domain modification may increase the protease resistance of a modified Fc domain at least 1%, (e.g., 1%, 2%, 3%, 4%, 5%, 6%, 7%, 8%, 9%, 10%, 20%, 30%, 40%, 50%, 60%, 70%, 80%, or 90%) or more, as compared to an unmodified Fc domain.

IV. Dimerization Selectivity Modules

In the present disclosure, a dimerization selectivity module is the part of the Fc domain monomer that facilitates the preferred pairing of two Fc domain monomers to form an Fc domain. Specifically, a dimerization selectivity module is that part of the $C_H3$ antibody constant domain of an Fc domain monomer which includes amino acid substitutions positioned at the interface between interacting $C_H3$ antibody constant domains of two Fc monomers. In a dimerization selectivity module, the amino acid substitutions make favorable the dimerization of the two $C_H3$ antibody constant domains as a result of the compatibility of amino acids chosen for those substitutions. The ultimate formation of the favored Fc domain is selective over other Fc domains which form from Fc domain monomers lacking dimerization selectivity modules or with incompatible amino acid substitutions in the dimerization selectivity modules. This type of amino acid substitution can be made using conventional molecular cloning techniques well-known in the art, such as QuikChange® mutagenesis.

In some embodiments, a dimerization selectivity module includes an engineered cavity (described further herein) in the $C_H3$ antibody constant domain. In other embodiments, a dimerization selectivity module includes an engineered protuberance (described further herein) in the $C_H3$ antibody constant domain. To selectively form an Fc domain, two Fc domain monomers with compatible dimerization selectivity modules, e.g., one $C_H3$ antibody constant domain containing an engineered cavity and the other $C_H3$ antibody constant domain containing an engineered protuberance, combine to form a protuberance-into-cavity pair of Fc domain monomers.

In other embodiments, an Fc domain monomer with a dimerization selectivity module containing positively-charged amino acid substitutions and an Fc domain monomer with a dimerization selectivity module containing negatively-charged amino acid substitutions may selectively combine to form an Fc domain through the favorable electrostatic steering (described further herein) of the charged amino acids. Specific dimerization selectivity modules are further listed, without limitation, in Tables 1 and 2 described further below.

In other embodiments, two Fc domain monomers include dimerization selectivity modules containing identical reverse charge mutations in at least two positions within the ring of charged residues at the interface between $C_H3$ domains. By reversing the charge of both members of two or more complementary pairs of residues in the two Fc domain monomers, mutated Fc domain monomers remain complementary to Fc domain monomers of the same mutated sequence, but have a lower complementarity to Fc domain monomers without those mutations. In one embodiment, an Fc domain includes Fc monomers including the double mutants K409D/D339K, K392D/D399K, E357K/K370E, D356K/K439D, K409E/D339K, K392E/D399K, E357K/K370D, or D356K/K439E. In another embodiment, an Fc domain includes Fc monomers including quadruple mutants combining any pair of the double mutants, e.g., K409D/D399K/E357K/K370E.

The formation of such Fc domains is promoted by the compatible amino acid substitutions in the $C_H3$ antibody constant domains. Two dimerization selectivity modules containing incompatible amino acid substitutions, e.g., both containing engineered cavities, both containing engineered protuberances, or both containing the same charged amino acids at the $C_H3$-$C_H3$ interface, will not promote the formation of an Fc domain.

Furthermore, other methods used to promote the formation of Fc domains with defined Fc domain monomers include, without limitation, the LUZ-Y approach (U.S. Patent Application Publication No. WO2011034605) which includes C-terminal fusion of a monomer α-helices of a leucine zipper to each of the Fc domain monomers to allow heterodimer formation, as well as strand-exchange engineered domain (SEED) body approach (Davis et al., *Protein Eng Des Sel.* 23:195-202, 2010) that generates Fc domain with heterodimeric Fc domain monomers each including alternating segments of IgA and IgG $C_H3$ sequences.

V. Engineered Cavities and Engineered Protuberances

The use of engineered cavities and engineered protuberances (or the "knob-into-hole" strategy) is described by Carter and co-workers (Ridgway et al., *Protein Eng.* 9:617-612, 1996; Atwell et al., *J Mol Biol.* 270:26-35, 1997; Merchant et al., *Nat Biotechnol.* 16:677-681, 1998). The knob and hole interaction favors heterodimer formation, whereas the knob-knob and the hole-hole interaction hinder homodimer formation due to steric clash and deletion of favorable interactions. The "knob-into-hole" technique is also disclosed in U.S. Pat. No. 5,731,168.

In the present disclosure, engineered cavities and engineered protuberances are used in the preparation of the Fc constructs described herein. An engineered cavity is a void that is created when an original amino acid in a protein is replaced with a different amino acid having a smaller side-chain volume. An engineered protuberance is a bump that is created when an original amino acid in a protein is replaced with a different amino acid having a larger side-chain volume. Specifically, the amino acid being replaced is in the $C_H3$ antibody constant domain of an Fc domain monomer and is involved in the dimerization of two Fc domain monomers. In some embodiments, an engineered cavity in one $C_H3$ antibody constant domain is created to accommodate an engineered protuberance in another $C_H3$ antibody constant domain, such that both $C_H3$ antibody constant domains act as dimerization selectivity modules (described above) that promote or favor the dimerization of the two Fc domain monomers. In other embodiments, an engineered cavity in one $C_H3$ antibody constant domain is created to better accommodate an original amino acid in another $C_H3$ antibody constant domain. In yet other embodiments, an engineered protuberance in one $C_H3$ antibody constant domain is created to form additional interactions with original amino acids in another $C_H3$ antibody constant domain.

An engineered cavity can be constructed by replacing amino acids containing larger side chains such as tyrosine or tryptophan with amino acids containing smaller side chains such as alanine, valine, or threonine. Specifically, some dimerization selectivity modules (described further above) contain engineered cavities such as Y407V mutation in the $C_H3$ antibody constant domain. Similarly, an engineered protuberance can be constructed by replacing amino acids containing smaller side chains with amino acids containing larger side chains. Specifically, some dimerization selectivity modules (described further above) contain engineered protuberances such as T366W mutation in the $C_H3$ antibody constant domain. In the present disclosure, engineered cavities and engineered protuberances are also combined with inter-$C_H3$ domain disulfide bond engineering to enhance heterodimer formation. Specifically, the cavity Fc contains an Y349C mutation, and the protuberance Fc contains an S354C mutation. Other engineered cavities and engineered protuberances, in combination with either disulfide bond engineering or structural calculations (mixed HA-TF) are included, without limitation, in Table 9.

TABLE 9

| Strategy | $CH_3$ antibody constant domain of Fc domain monomer 1 | $CH_3$ antibody constant domain of Fc domain monomer 2 | Reference |
| --- | --- | --- | --- |
| Engineered cavities and protuberances ("knob-into-hole") | Y407T | T366Y | U.S. Pat. No. 8,216,805 |
| | Y407A | T366W | U.S. Pat. No. 8,216,805 |
| | F405A | T394W | U.S. Pat. No. 8,216,805 |
| | Y407T | T366Y | U.S. Pat. No. 8,216,805 |
| | T394S | F405W | U.S. Pat. No. 8,216,805 |
| | T394W:Y407T | T366Y:F405A | U.S. Pat. No. 8,216,805 |
| | T394S:Y407A | T366W:F405W | U.S. Pat. No. 8,216,805 |
| | T366W:T394S | F405W:Y4074 | U.S. Pat. No. 8,216,805 |
| Engineered cavities and protuberances ("knob-into-hole"), S-S engineering | T366S:L368A: Y407V:Y349C | T366W:S354C | Zeidler et al., *J Immunol.* 163: 1246-52, 1999 |
| Mixed HA-TF | S364H:F405A | Y349T:T394F | WO2006106905 |

Replacing an original amino acid residue in the $C_H3$ antibody constant domain with a different amino acid residue can be achieved by altering the nucleic acid encoding the original amino acid residue. The upper limit for the number of original amino acid residues that can be replaced is the total number of residues in the interface of the $C_H3$ antibody constant domains, given that sufficient interaction at the interface is still maintained.

VI. Electrostatic Steering

Electrostatic steering is the utilization of favorable electrostatic interactions between oppositely charged amino acids in peptides, protein domains, and proteins to control the formation of higher ordered protein molecules. A method of using electrostatic steering effects to alter the interaction of antibody domains to reduce for formation of homodimer in favor of heterodimer formation in the generation of bi-specific antibodies is disclosed in U.S. Patent Application Publication No. 2014-0024111.

In the present disclosure, electrostatic steering is used to control the dimerization of Fc domain monomers and the formation of Fc constructs. In particular, to control the dimerization of Fc domain monomers using electrostatic steering, one or more amino acid residues that make up the $C_H3$-$C_H3$ interface are replaced with positively- or negatively-charged amino acid residues such that the interaction becomes electrostatically favorable or unfavorable depending on the specific charged amino acids introduced. In some embodiments, a positively-charged amino acid in the interface, such as lysine, arginine, or histidine, is replaced with a negatively-charged amino acid such as aspartic acid or glutamic acid. In other embodiments, a negatively-charged amino acid in the interface is replaced with a positively-charged amino acid. The charged amino acids may be introduced to one of the interacting $C_H3$ antibody constant domains, or both. By introducing charged amino acids to the interacting $C_H3$ antibody constant domains, dimerization selectivity modules (described further above) are created that can selectively form dimers of Fc domain monomers as controlled by the electrostatic steering effects resulting from the interaction between charged amino acids.

In one particular example, to create a dimerization selectivity module including reversed charges, amino acid Asp399 in the $C_H3$ antibody constant domain is replaced with Lys, and amino acid Lys409 is replaced with Asp. Heterodimerization of Fc domain monomers can be promoted by introducing different, but compatible, mutations in the two Fc domain monomers, such as the charge residue pairs included, without limitation, in Table 10, Homodimerization of Fc domain monomers can be promoted by introducing the same mutations in both Fc domain monomers in a symmetric fashion, such as the double mutants K409D/D339K or K392D/D399K.

TABLE 10

| $CH_3$ antibody constant domain of Fc domain monomer 1 | $CH_3$ antibody constant domain of Fc domain monomer 2 | Reference |
| --- | --- | --- |
| K408D | D399K | US 2014/0024111 |
| K409D | D399R | US 2014/0024111 |
| K409E | D399K | US 2014/0024111 |
| K409E | D399R | US 2014/0024111 |
| K392D | D399K | US 2014/0024111 |
| K392D | D399R | US 2014/0024111 |
| K392E | D399K | US 2014/0024111 |
| K392E | D399R | US 2014/0024111 |
| K409D:K392D | D399K:E356K | Gunasekaran et al., *J Biol Chem.* 285: 19637-46, 2010 |
| K370E:K409D: K439E | E356K:E357K: D399K | Martens et al., *Clin Cancer Res.* 12: 6144-52, 2006 |

VII. Linkers

In the present disclosure, a linker is used to describe a linkage or connection between polypeptides or protein domains and/or associated non-protein moieties. In some embodiments, a linker is a linkage or connection between at least two Fc domain monomers, for which the linker connects the C-terminus of the $C_H3$ antibody constant domain of a first Fc domain monomer to the N-terminus of the hinge domain of a second Fc domain monomer, such that the two Fc domain monomers are joined to each other in tandem series. In other embodiments, a linker is a linkage between an Fc domain monomer and any other protein domains that are attached to it. For example, a linker can attach the C-terminus of the $C_H3$ antibody constant domain of an Fc domain monomer to the N-terminus of an albumin-binding peptide. In another example, a linker can connect the C-terminus of a $C_H1$ antibody constant domain to the N-terminus of the hinge domain of an Fc domain monomer. In yet other embodiments, a linker can connect two individual protein domains (not including an Fc domain), for example, the C-terminus of a $C_L$ antibody constant domain can be attached to the N-terminus of a $C_H1$ antibody constant domain by way of a linker.

A linker can be a simple covalent bond, e.g., a peptide bond, a synthetic polymer, e.g., a polyethylene glycol (PEG) polymer, or any kind of bond created from a chemical reaction, e.g. chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art, or by natural production from a host cell, wherein a polynucleotide sequence encoding the DNA sequences of both proteins, e.g., two Fc domain monomer, in tandem series can be directly transcribed and translated into a contiguous polypeptide encoding both proteins by the necessary molecular machineries, e.g., DNA polymerase and ribosome, in the host cell.

In the case that a linker is a synthetic polymer, e.g., a PEG polymer, the polymer can be functionalized with reactive chemical functional groups at each end to react with the terminal amino acids at the connecting ends of two proteins.

In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react to through synthetic chemistry means to form a chemical bond, thus connecting the two proteins together. Such chemical conjugation procedures are routine for those skilled in the art.

Spacer

Figure 6:
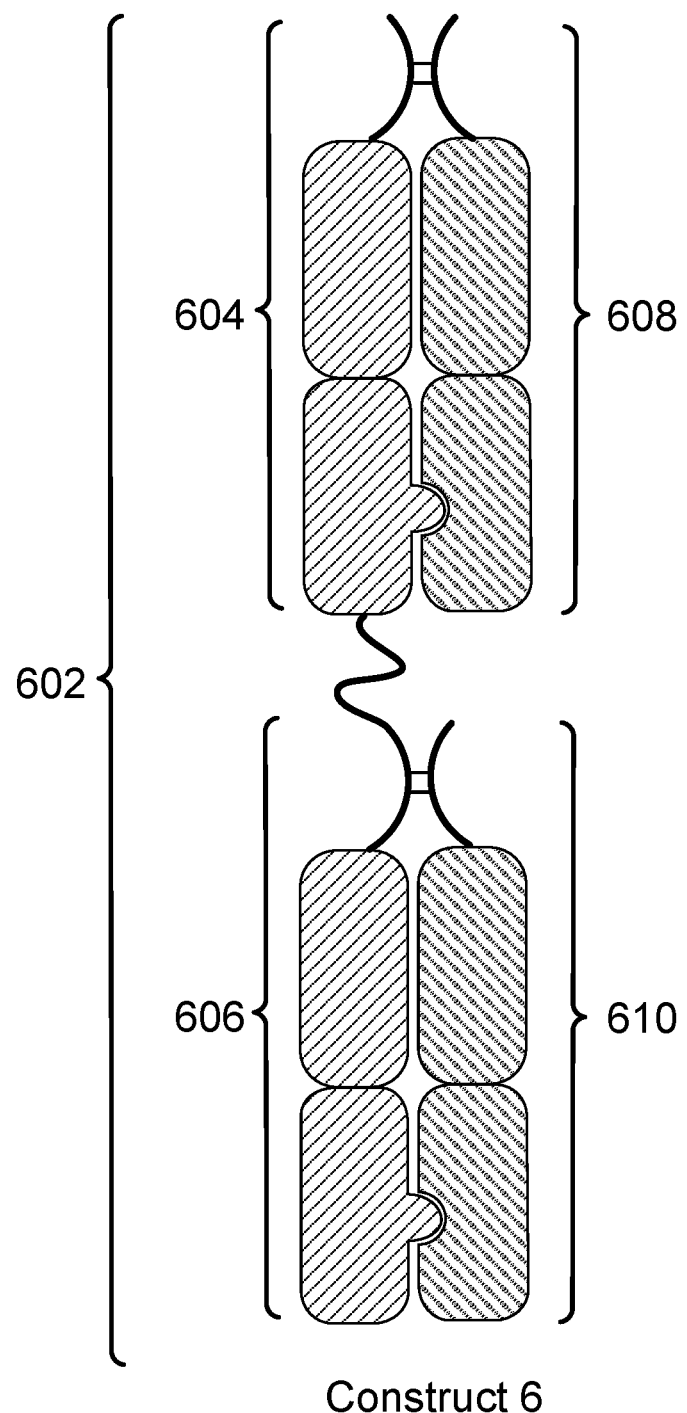
FIG. 6 is an illustration of an Fc construct (construct 6) containing two Fc domains formed from three polypeptides. The first polypeptide (602) contains two protuberance-containing Fc domain monomers (604 and 606) joined in a tandem series, while the second and third polypeptides (608 and 610, respectively) each contain an Fc domain monomer engineered to contain a corresponding cavity.
Figure 7A:
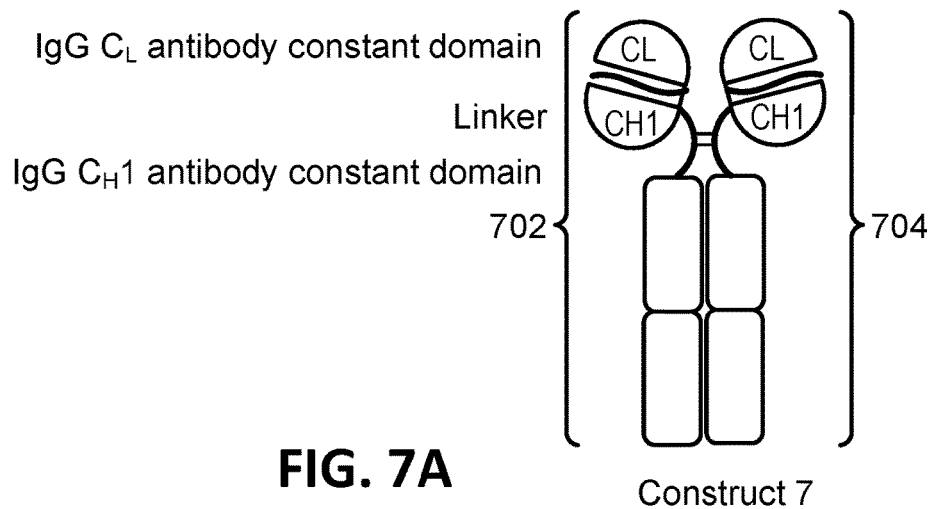
FIG. 7A is an illustration of another Fc construct (construct 7). This Fc construct contains a dimer of two $C_L$-$C_H1$-Fc domain monomers (702 and 704). In this embodiment, the $C_L$ antibody constant domains have joined to the adjacent $C_H1$ antibody constant domains.
Figure 7B:
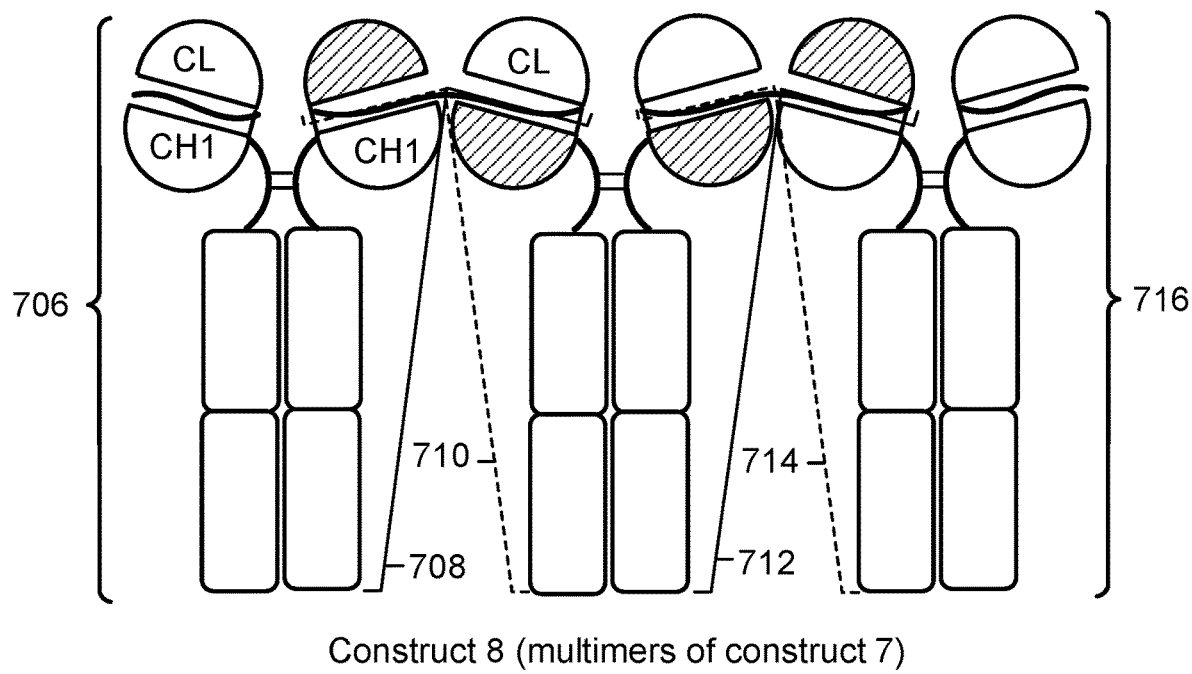
FIG. 7B is an illustration of an Fc construct (construct 8) containing multimers of $C_L$-$C_H1$-Fc domain monomers (e.g., 706, 708, and 710) containing multiple Fc domains. In this Fc construct, the constituent polypeptide can be the same as the constituent polypeptide in construct 7. The $C_L$ antibody constant domain of one Fc construct (e.g., 712) interacts with the $C_H1$ antibody constant domain of a second, neighboring Fc construct (e.g., 714).

In the present disclosure, a linker between two Fc domain monomers can be an amino acid spacer including 3-200 amino acids (e.g., 3-150, 3-100, 3-60, 3-50, 3-40, 3-30, 3-20, 3-10, 3-8, 3-5, 4-30, 5-30, 6-30, 8-30, 10-20, 10-30, 12-30, 14-30, 20-30, 15-25, 15-30, 18-22, and 20-30 amino acids). Suitable peptide spacers are known in the art, and include, for example, peptide linkers containing flexible amino acid residues such as glycine and serine. In certain embodiments, a spacer can contain motifs, e.g., multiple or repeating motifs, of GS, GGS, GGGGS (SEQ ID NO: 1), GGSG (SEQ ID NO: 2), or SGGG (SEQ ID NO: 3). In certain embodiments, a spacer can contain 2 to 12 amino acids including motifs of GS, e.g., GS, GSGS (SEQ ID NO: 4), GSGSGS (SEQ ID NO: 5), GSGSGSGS (SEQ ID NO: 6), GSGSGSGSGS (SEQ ID NO: 7), or GSGSGSGSGSGS (SEQ ID NO: 8). In certain other embodiments, a spacer can contain 3 to 12 amino acids including motifs of GGS, e.g., GGS, GGSGGS (SEQ ID NO: 9), GGSGGSGGS (SEQ ID NO: 10), and GGSGGSGGSGGS (SEQ ID NO: 11). In yet other embodiments, a spacer can contain 4 to 12 amino acids including motifs of GGSG (SEQ ID NO: 12), e.g., GGSG (SEQ ID NO: 13), GGSGGGSG (SEQ ID NO: 14), or GGSGGGSGGGSG (SEQ ID NO: 15). In other embodiments, a spacer can contain motifs of GGGGS (SEQ ID NO: 16), e.g., GGGGSGGGGSGGGGS (SEQ ID NO: 17). In other embodiments, a spacer can also contain amino acids other than glycine and serine, e.g., GENLYFQSGG (SEQ ID NO: 18), SACYCELS (SEQ ID NO: 19), RSIAT (SEQ ID NO: 20), RPACKIPNDLKQKVMNH (SEQ ID NO: 21), GGSAGGSGSGSSGGSSGASGTGTAGGTGSGSGTGSG (SEQ ID NO: 22), AAANSSIDLISVPVDSR (SEQ ID NO: 23), or GGSGGGSEGGGSEGGGSEGGGSEGGGSEGGGSGGGS (SEQ ID NO: 24). In certain embodiments in the present disclosure, a 12- or 20-amino acid peptide spacer is used to connect two Fc domain monomers in tandem series (FIGS. 4-6), the 12- and 20-amino acid peptide spacers consisting of sequences GGGSGGGSGGGS (SEQ ID NO: 25) and SGGGSGGGSGGGSGGGSGGG (SEQ ID NO: 26), respectively. In other embodiments, an 18-amino acid peptide spacer consisting of sequence GGSGGGSGGGSGGGSGGS (SEQ ID NO: 27) is used to connect $C_L$ and $C_H1$ antibody constant domains (FIG. 7A-7B). In certain embodiments, a spacer can contain motifs of GGGG (SEQ ID NO: 51), e.g., GGGGGGGG (SEQ ID NO: 52), GGGGGGGGGGGG (SEQ ID NO: 53), GGGGGGGGGGGGGGGG (SEQ ID NO: 54), or GGGGGGGGGGGGGGGGGGGG (SEQ ID NO: 55). In certain embodiments, a spacer is GGGGGGGGGGGGGGGGGGGG (SEQ ID NO: 55).

VIII. Serum Protein-Binding Peptides

Binding to serum protein peptides can improve the pharmacokinetics of protein pharmaceuticals, and in particular the Fc constructs described here may be fused with serum protein-binding peptides As one example, albumin-binding peptides that can be used in the methods and compositions described here are generally known in the art. In one embodiment, the albumin binding peptide comprises, consists of, or consists essentially of the sequence DICLPRWGCLW (SEQ ID NO: 28). In one embodiment, the albumin binding peptide comprises, consists of, or consists essentially of the sequence DICLPRWGCLW (SEQ ID NO: 28) with up to 10 (e.g., up to 9, 8, 7, 6, 5, 4, 3, 2, or 1) single amino acid modifications (e.g., substitutions, e.g., conservative substitutions).

Figure 4:
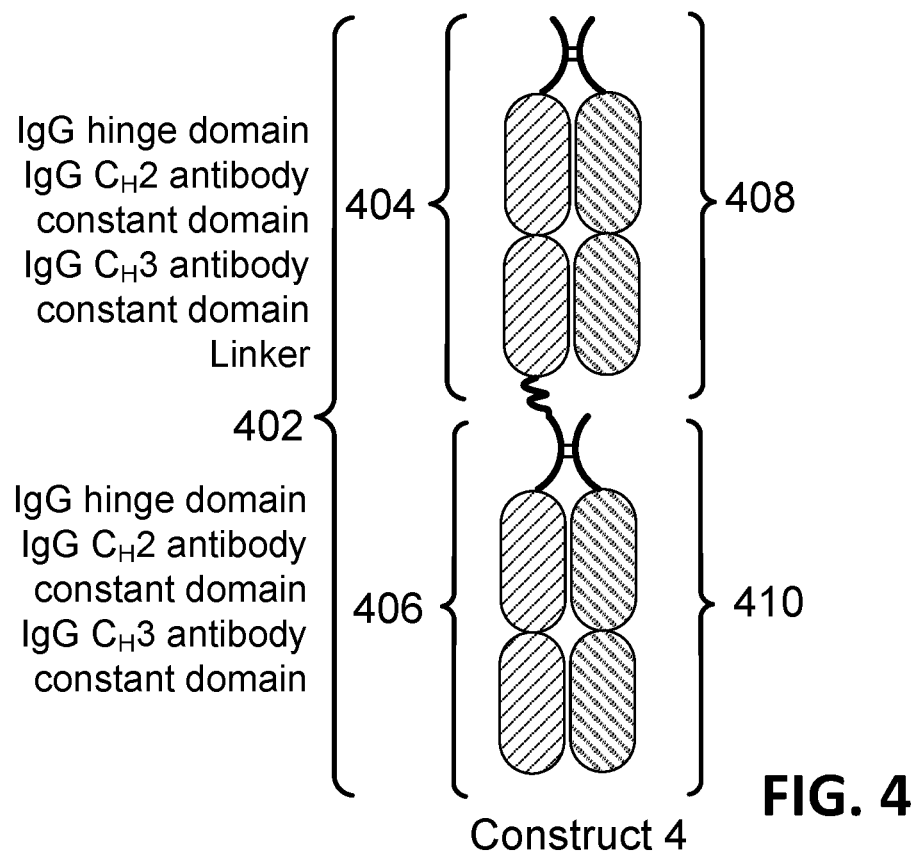
FIG. 4 is an illustration of an Fc construct (construct 4) containing two Fc domains. This construct is formed from three polypeptides. The first polypeptide (402) contains two wt Fc domain monomers (404 and 406) joined in a tandem series. Each of the second and third polypeptides (408 and 410, respectively) contains a wt Fc domain monomer.
Figure 5:
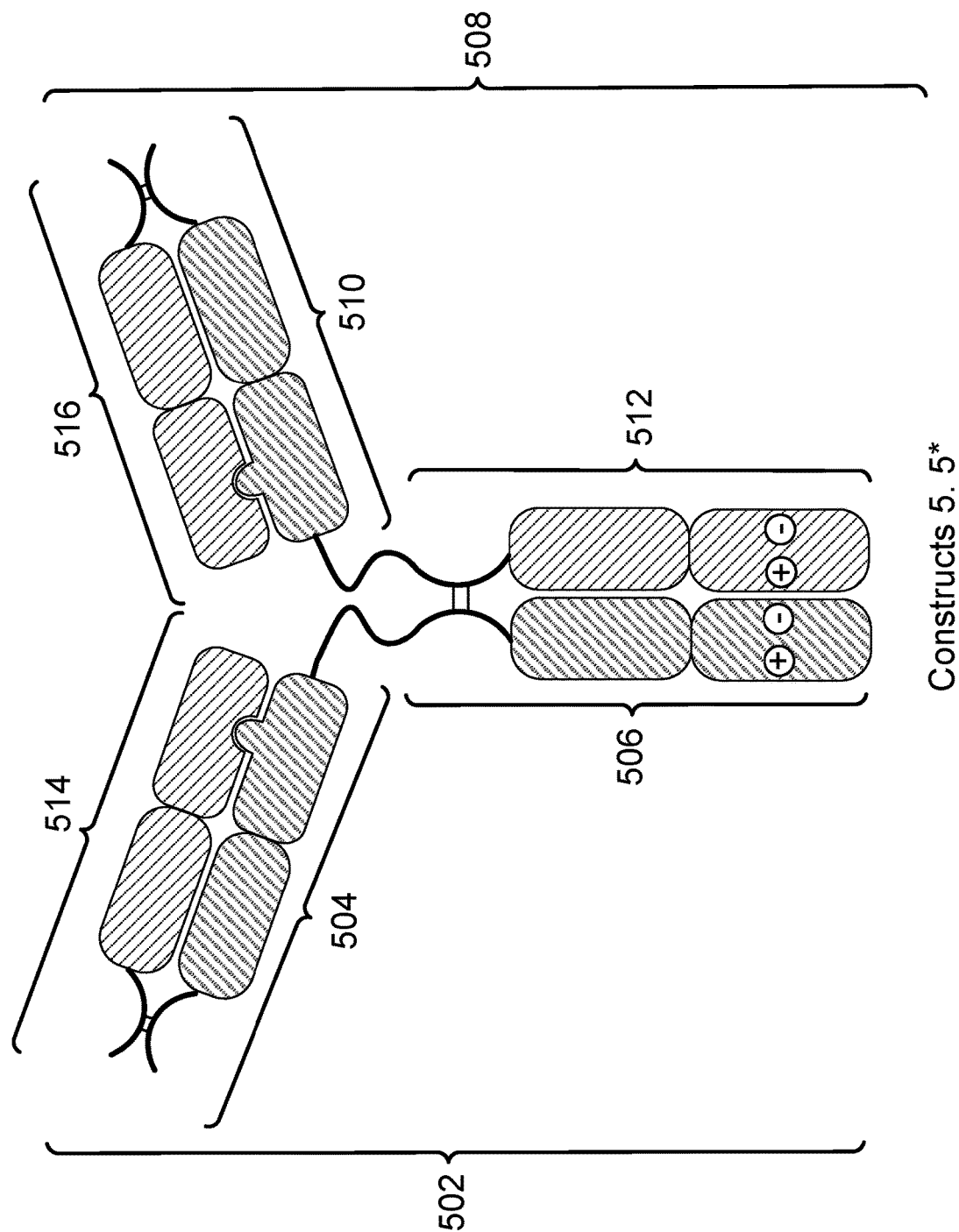
FIG. 5 is an illustration of an Fc construct (construct 5 or construct 5*) containing three Fc domains formed from four polypeptides. The first polypeptide (502) contains one Fc domain monomer containing different charged amino acids at the $C_H3$-$C_H3$ interface than the wt sequence (506) joined in a tandem series with a protuberance-containing Fc domain monomer (504). The second polypeptide (508) contains an Fc domain monomer containing different charged amino acids at the $C_H3$-$C_H3$ interface than the wt sequence (512) joined in a tandem series with another protuberance-containing Fc domain monomer (510). The third and fourth polypeptides (514 and 516, respectively) each contain a cavity-containing Fc domain monomer.

In the present disclosure, albumin-binding peptides may be attached to the N- or C-terminus of certain polypeptides in the Fc construct. In one embodiment, an albumin-binding peptide may be attached to the C-terminus of one or more polypeptides in constructs 1, 2, 3, or 7A (FIGS. 1, 2, 3, and 7A, respectively). In another embodiment, an albumin-binding peptide can be fused to the C-terminus of the polypeptide encoding two Fc domain monomers linked in tandem series in constructs 4, 5, and 6 (FIGS. 4, 5, and 6, respectively). In yet another embodiment, an albumin-binding peptide can be attached to the C-terminus of Fc domain monomer which is joined to the second Fc domain monomer in the polypeptide encoding the two Fc domain monomers linked in tandem series, as shown in constructs 4 and 6 (FIGS. 4 and 6, respectively). Albumin-binding peptides can be fused genetically to Fc constructs or attached to Fc constructs through chemical means, e.g., chemical conjugation. If desired, a spacer can be inserted between the Fc construct and the albumin-binding peptide. Without being bound to a theory, it is expected that inclusion of an albumin-binding peptide in an Fc construct of the disclosure may lead to prolonged retention of the therapeutic protein through its binding to serum albumin.

IX. Fc Constructs

In general, the disclosure features Fc constructs having 2-10 Fc domains (e.g., 2, 3, 4, 5, 6, 7, 8, 9, or 10 Fc domains; 2-8 Fc domains, 2-6 Fc domains, 2-4 Fc domains, 2-3 Fc domains, 5-10 Fc domains, 5-8 Fc domains, or 5-6 Fc domains). These may have greater binding affinity and/or avidity than a single wild-type Fc domain for an Fc receptor, e.g., FcγRIIIa. The disclosure discloses methods of engineering amino acids at the interface of two interacting $C_H3$ antibody constant domains such that the two Fc domain monomers of an Fc domain selectively form a dimer with each other, thus preventing the formation of unwanted multimers or aggregates. An Fc construct includes an even number of Fc domain monomers, with each pair of Fc domain monomers forming an Fc domain. An Fc construct includes, at a minimum, one functional Fc domain formed from a dimer of two Fc domain monomers.

Figure 2:
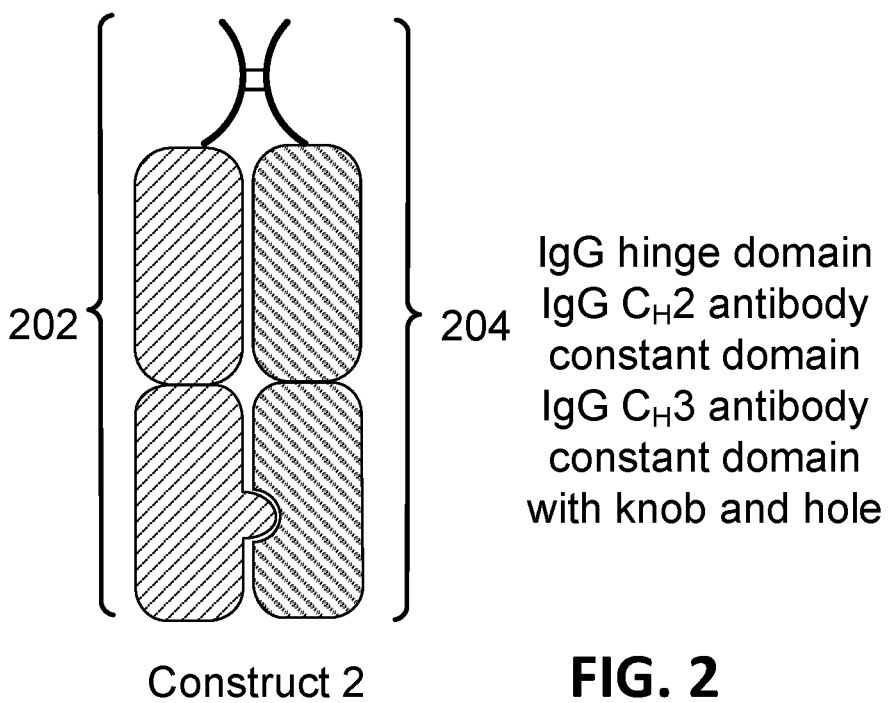
FIG. 2 is an illustration of an Fc construct (construct 2) containing a dimer of two Fc domain monomers. The first Fc domain monomer (202) contains a protuberance in its $C_H3$ antibody constant domain, while the second Fc domain monomer (204) contains a cavity in the juxtaposed position in its $C_H3$ antibody constant domain.
Figure 3:
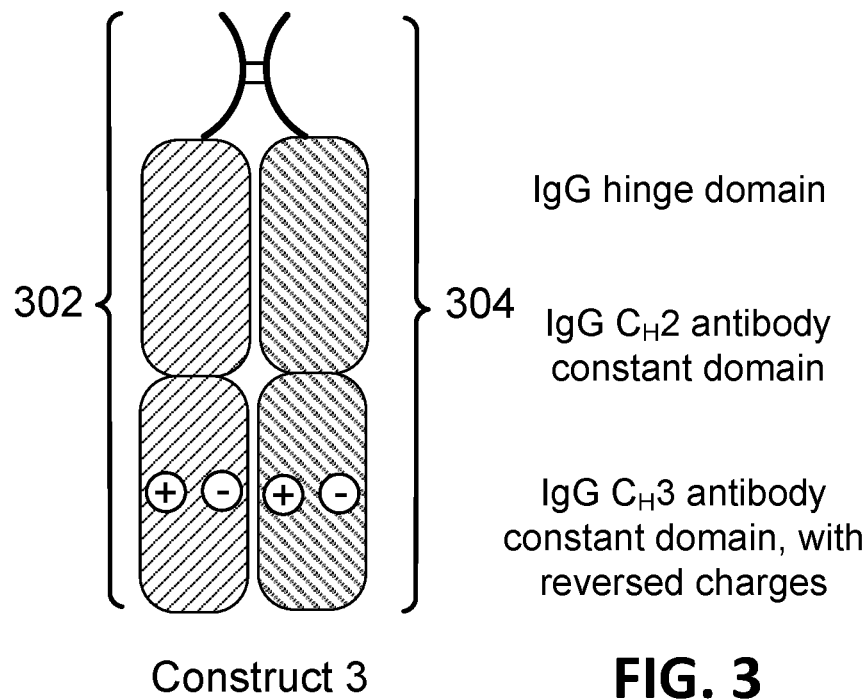
FIG. 3 is an illustration of another Fc construct (construct 3). This Fc construct contains a dimer of two Fc domain monomers (302 and 304), wherein both Fc domain monomers contain different charged amino acids at their $C_H3$-$C_H3$ interface than the wt sequence to promote favorable electrostatic interaction between the two Fc domain monomers.

In some embodiments, an Fc construct contains one Fc domain including a dimer of two Fc domain monomers (FIGS. 1-3 and 7A). The interacting $C_H3$ antibody constant domains may be unmodified (FIG. 1) or may contain amino acid substitutions at their interface. Specifically, the amino acid substitutions can be engineered cavities (FIG. 2), engineered protuberances (FIG. 2), or charged amino acids (FIG. 3).

In other embodiments, an Fc construct contains two Fc domains (FIGS. 4 and 6) formed from three polypeptides. The first polypeptide contains two Fc domain monomers joined in tandem series joined by way of a linker, and the second and third polypeptides contain one Fc domain monomer. The second and third polypeptides may be the same polypeptide or may be different polypeptides. FIG. 4 depicts an example of such an Fc construct. The first polypeptide contains two wild-type Fc domain monomers joined in tandem series by way of a linker, and the second and third polypeptides each contain one wild-type Fc domain monomer. One of the Fc domain monomers in the first polypeptide forms a first Fc domain with the second polypeptide, while the other Fc domain monomer in the first polypeptide forms a second Fc domain with the third polypeptide. The second and third polypeptides are not attached or linked to each other. FIG. 6 depicts a similar Fc construct to that of FIG. 4. In FIG. 6, the Fc domain monomers in the first polypeptide both contain engineered protuberances in the $C_H3$ antibody constant domains, while the second and third polypeptides contain engineered cavities in the $C_H3$ antibody constant domains. The engineered protuberance-into-cavity $C_H3$-$C_H3$ interface favors the formation of heterodimers of Fc domain monomers and prevents the uncontrolled formation of unwanted multimers. As described further herein, in Example 4, dimerization selectivity modules including engineered $C_H3$ antibody constant domains prevent the formation of unwanted multimers that are seen in Example 3, which describes Fc construct formation from Fc domain monomers lacking dimerization selectivity modules.

Furthermore, in other embodiments, an Fc construct can contain three Fc domains formed from four polypeptides (FIG. 5). The first and second polypeptides can be the same or different, as can the third and fourth polypeptides. In this example, the first and second polypeptides both encode two Fc domain monomers connected by way of a linker in tandem series, wherein one Fc domain monomer contains charged amino acid substitutions in the $C_H3$ antibody constant domain while the other Fc domain monomer contains a protuberance in the $C_H3$ antibody constant domain. The third and fourth polypeptides both encode an Fc domain monomer with a cavity. The first and second polypeptides form a first Fc domain with each other through interaction of the reverse charges in their $C_H3$ antibody constant domains. The second and third Fc domains are formed from protuberance-into-cavity interactions between the protuberances in the first and second polypeptides and the cavities in the third and fourth polypeptides. Each Fc domain monomer in this Fc construct contains a dimerization selectivity module which promotes the formation of specific Fc domains.

In yet other embodiments, a single polypeptide can form dimers (e.g., construct 7A; FIG. 7A) or multimers (e.g., construct 7B; FIG. 7B), not through interaction between $C_H3$ antibody constant domains, but through interaction between $C_L$ constant domains and $C_H1$ constant domains. FIG. 7B depicts an Fc construct containing multiple Fc domains in which the $C_L$ domain of one Fc domain interacts with the $C_H1$ domain of a neighboring Fc domain.

Figure 8:
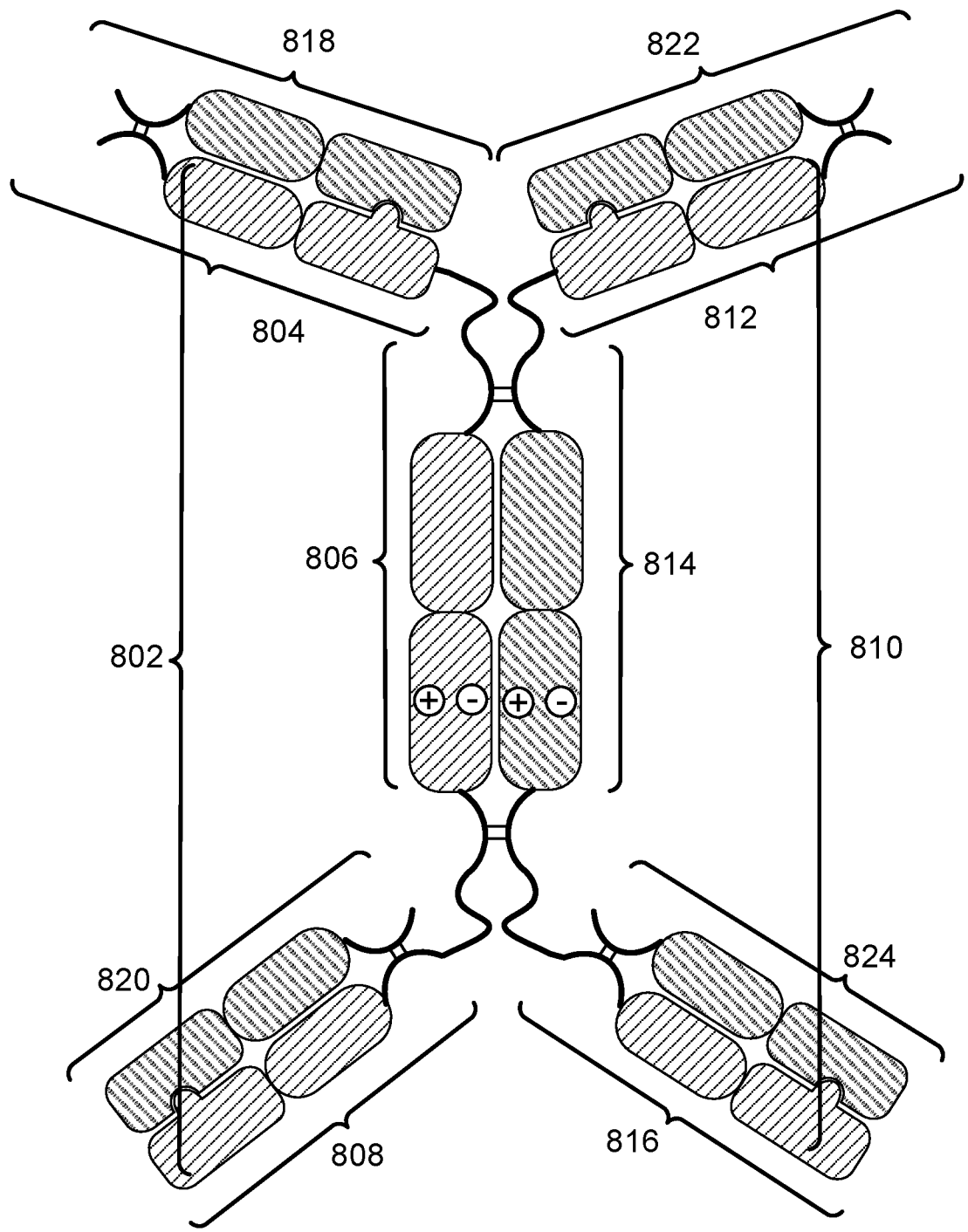
FIG. 8 is an illustration of an Fc construct (construct 9) containing five Fc domains formed from six polypeptides. The first and second polypeptides (802 and 810) each contain three Fc domain monomers (804, 806, 808, and 812, 814, 816, respectively) joined in a tandem series. Specifically, in polypeptide 802 or 810, a first protuberance-containing Fc domain monomer (804 or 812) is connected to a second Fc domain monomer containing different charged amino acids at the $C_H3$-$C_H3$ interface than the wt sequence (806 or 814), which is connected to a third protuberance-containing Fc domain monomer (808 or 816). The third through sixth polypeptides (818, 820, 822, and 824) each contain a cavity-containing Fc domain monomer and form an Fc domain with each of Fc domain monomers 804, 808, 812 and 816, respectively.
Figure 9:
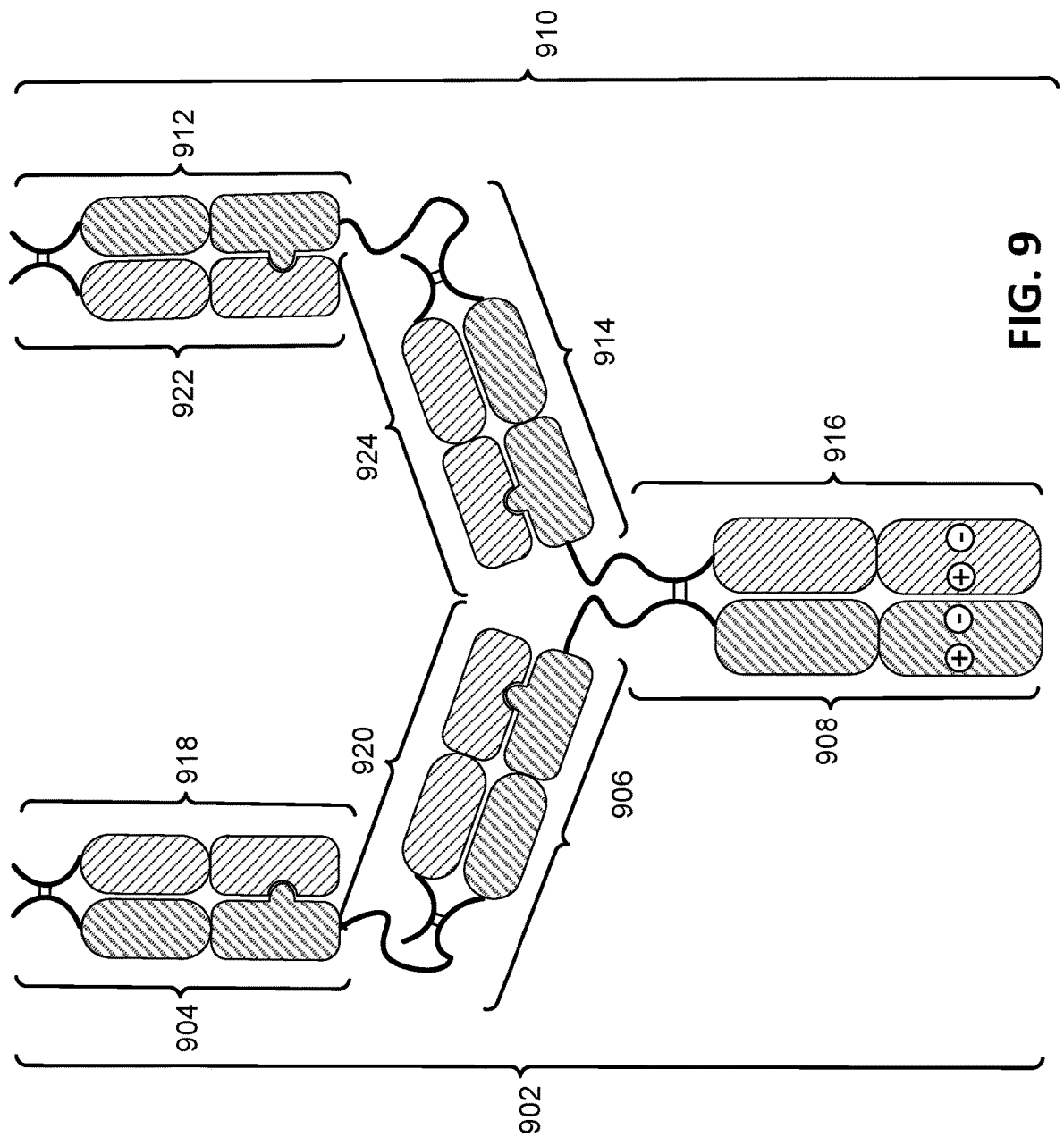
FIG. 9 is an illustration of an Fc construct (construct 10) containing five Fc domains formed from six polypeptides. The first and second polypeptides (902 and 910) each contain three Fc domain monomers (904, 906, 908, and 912, 914, 916, respectively) joined in a tandem series. Specifically, in polypeptide 902 or 910, a first protuberance-containing Fc domain monomer (904 or 912) is connected to a second protuberance-containing Fc domain monomer (906 or 914), which is connected to a third Fc domain monomer containing different charged amino acids at the $C_H3$-$C_H3$ interface than the wt sequence (908 or 916). The third through sixth polypeptides (918, 920, 922, and 924) each contain a cavity-containing Fc domain monomer and form an Fc domain with each of Fc domain monomers 904, 906, 912 and 914, respectively.

In yet other embodiments, Fc constructs can contain five Fc domains formed from six polypeptides. Two examples are depicted in FIGS. 8 and 9. While these depicted Fc constructs are comprised of six polypeptides, four of the polypeptides can be encoded by the same nucleic acid, and the remaining two polypeptides can also be encoded by the same nucleic acid. As a result, these Fc constructs can be produced by the expression of two nucleic acids in a suitable host cell.

Figure 10:
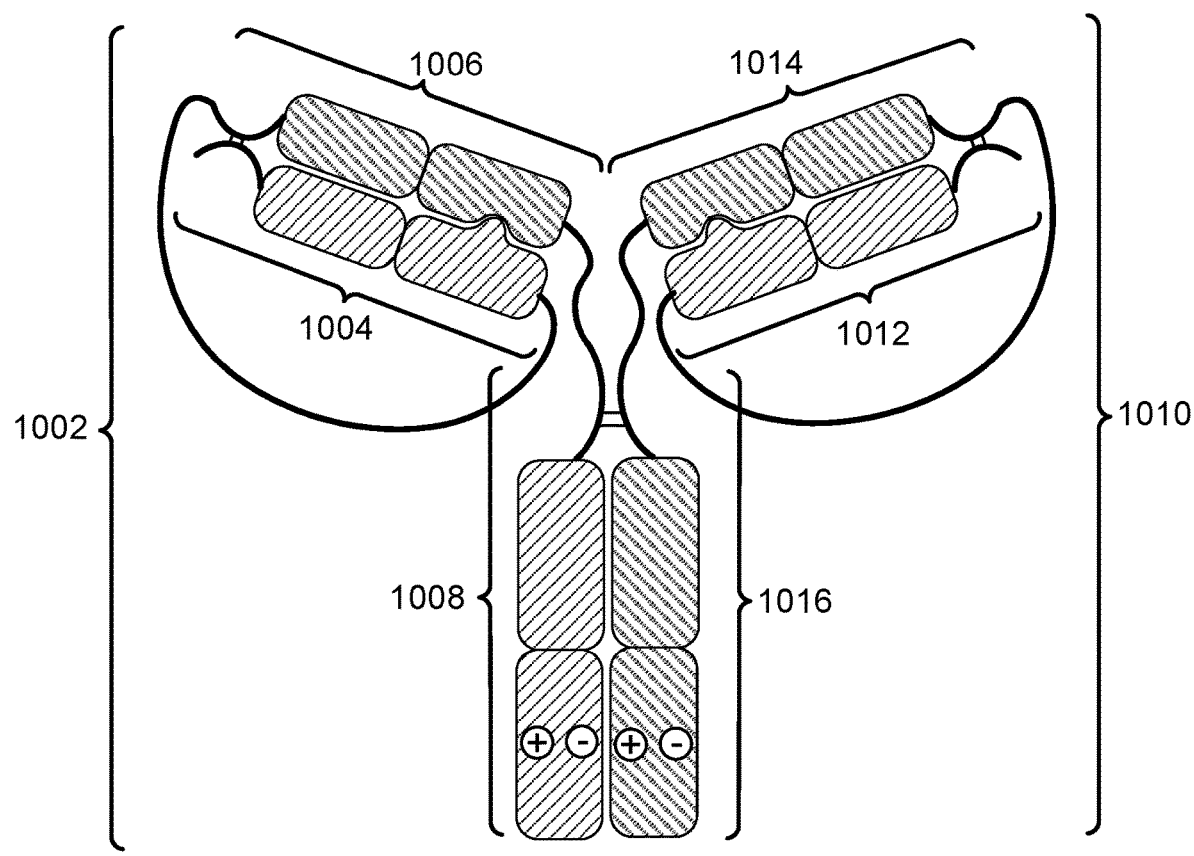
FIG. 10 is an illustration of an Fc construct (construct 11) containing three Fc domains formed from two polypeptides of identical sequence. The two polypeptides (1002 and 1010) each contain three Fc domain monomers (1004, 1006, 1008, and 1012, 1014, 1016, respectively) joined in a tandem series. Specifically, each polypeptide contains a first protuberance-containing Fc domain monomer (1004 or 1012) connected to a second cavity-containing Fc domain monomer (1006 or 1014), which is connected to a third Fc domain monomer with different charged amino acids at the $C_H3$-$C_H3$ interface than the wt sequence (1008, or 1016). Fc domain monomers 1008 and 1016 associate to form a first Fc domain; Fc domain monomers 1004 and 1006 associate to form a second Fc domain; and Fc domain monomers 1012 and 1014 associate to form a third Fc domain. Construct 11 can be formed from expression of a single polypeptide sequence in a host cell.

In another embodiment, an Fc construct containing two or more Fc domains can be formed from two polypeptides having the same primary sequence. Such a construct can be formed from expression of a single polypeptide sequence in a host cell. An example is depicted in FIG. 10. In this example, a single nucleic acid is sufficient to encode an Fc construct containing three Fc domains. Two Fc domain monomers that are part of the same polypeptide are permitted to form an Fc domain by the inclusion of a flexible linker of a sufficient length and flexibility; this linker may be a cleavable linker. This same polypeptide also contains a third Fc domain monomer joined by way of an optional flexible linker. This third Fc domain monomer is capable of joining to another Fc domain monomer to produce the Y-shaped Fc construct depicted in FIG. 10. Formation of Fc domains can be controlled through the use of dimerization selectivity modules, as is also depicted in FIG. 10. In some cases, an Fc construct containing three Fc domains can be formed from two polypeptides, e.g., as shown in FIG. 5. Such a construct can be formed from expression of two polypeptide sequences in a host cell.

In some embodiments, one or more Fc polypeptides in an Fc construct contain a terminal lysine residue. In some embodiments, one or more Fc polypeptides in an Fc construct do not contain a terminal lysine residue. In some embodiments, all of the Fc polypeptides in an Fc construct contain a terminal lysine residue. In some embodiments, all of the Fc polypeptides in an Fc construct do not contain a terminal lysine residue. In one example, the terminal lysine residue in an Fc polypeptide comprises, consists of, or consists essentially of the sequence of any one of SEQ ID NOs: 30, 32, 34, 36, 38, 40, 42, 44, 45, and 46 (see Example 1) may be removed to generate a corresponding Fc polypeptide that does not contain a terminal lysine residue. In another example, a terminal lysine residue may be added to an Fc polypeptide comprising, consisting of, or consisting essentially of the sequence of SEQ ID NO: 48 or 50 (see Example 1) to generate a corresponding Fc polypeptide that contains a terminal lysine residue. In another embodiment, a terminal lysine residue may be added to an Fc polypeptide comprising, consisting of, or consisting essentially of the sequence of SEQ ID NO: 48 or 50 (see Example 1) to generate a corresponding Fc polypeptide that contains a terminal lysine residue with up to 10 (e.g., up to 9, 8, 7, 6, 5, 4, 3, 2, or 1) single amino acid modifications (e.g., substitutions, e.g., conservative substitutions).

X. Host Cells and Protein Production

In the present disclosure, a host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (transformation, transfection, electroporation, calcium phosphate precipitation, direct microinjection, etc.). Host cells can be of either mammalian or bacterial origin. Mammalian host cells include, but are not limited to, CHO (or CHO-derived cell strains, e.g., CHO-K1, CHO-DXB11 CHO-DG44), murine host cells (e.g., NS0, Sp2/0), VERY, HEK (e.g., HEK293), BHK, HeLa, COS, MDCK, 293, 3T3, W138, BT483, Hs578T, HTB2, BT20 and T47D, CRL7O3O and HsS78Bst cells. Host cells can also be chosen that modulate the expression of the protein constructs, or modify and process the protein product in the specific fashion desired. Different host cells have characteristic and specific mechanisms for the post-translational processing and modification of protein products. Appropriate cell lines or host systems can be chosen to ensure the correct modification and processing of the protein expressed.

For expression and secretion of protein products from their corresponding DNA plasmid constructs, host cells may be transfected or transformed with DNA controlled by appropriate expression control elements known in the art, including promoter, enhancer, sequences, transcription terminators, polyadenylation sites, and selectable markers. Methods for expression of therapeutic proteins are known in the art. See, for example, Paulina Balbas, Argelia Lorence (eds.) *Recombinant Gene Expression: Reviews and Protocols* (Methods in Molecular Biology), Humana Press; 2nd ed. 2004 edition (Jul. 20, 2004); Vladimir Voynov and Justin A. Caravella (eds.) *Therapeutic Proteins: Methods and Protocols* (Methods in Molecular Biology) Humana Press; 2nd ed. 2012 edition (Jun. 28, 2012).

XI. Purification

An Fc construct can be purified by any method known in the art of protein purification, for example, by chromatography (e.g., ion exchange, affinity (e.g., Protein A affinity), and size-exclusion column chromatography), centrifugation, differential solubility, or by any other standard technique for the purification of proteins. For example, an Fc construct can be isolated and purified by appropriately selecting and combining affinity columns such as Protein A column with chromatography columns, filtration, ultra filtration, salting-out and dialysis procedures (see, e.g., *Process Scale Purification of Antibodies*, Uwe Gottschalk (ed.) John Wiley & Sons, Inc., 2009; and Subramanian (ed.) *Antibodies—Volume I—Production and Purification*, Kluwer Academic/Plenum Publishers, New York (2004)). In some instances, an Fc construct can be conjugated to marker sequences, such as a peptide to facilitate purification. An example of a marker amino acid sequence is a hexa-histidine peptide, which binds to nickel-functionalized agarose affinity column with micromolar affinity. Other peptide tags useful for purification include, but are not limited to, the hemagglutinin "HA" tag, which corresponds to an epitope derived from the influenza hemagglutinin protein (Wilson et al., 1984, Cell 37:767).

For the Fc constructs, Protein A column chromatography may be employed as a purification process. Protein A ligands interact with Fc constructs through the Fc region, making Protein A chromatography a highly selective capture process that is able to remove most of the host cell proteins. In the present disclosure, Fc constructs may be purified using Protein A column chromatography as described in Example 2.

XII. Pharmaceutical Compositions/Preparations

The disclosure features pharmaceutical compositions that include one or more Fc constructs described herein. In one embodiment, a pharmaceutical composition includes a substantially homogenous population of Fc constructs that are identical or substantially identical in structure. In various examples, the pharmaceutical composition includes a substantially homogenous population of any one of constructs 1-10 and 5*.

A therapeutic protein construct, e.g., an Fc construct, of the present disclosure can be incorporated into a pharmaceutical composition. Pharmaceutical compositions including therapeutic proteins can be formulated by methods know to those skilled in the art. The pharmaceutical composition can be administered parenterally in the form of an injectable formulation including a sterile solution or suspension in water or another pharmaceutically acceptable liquid. For example, the pharmaceutical composition can be formulated by suitably combining the Fc construct with pharmaceutically acceptable vehicles or media, such as sterile water for injection (WFI), physiological saline, emulsifier, suspension agent, surfactant, stabilizer, diluent, binder, excipient, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™ HCO-50, and the like commonly known in the art. Formulation methods for therapeutic protein products are known in the art, see e.g., Banga (ed.) *Therapeutic Peptides and Proteins: Formulation, Processing and Delivery Systems* (2d ed.) Taylor & Francis Group, CRC Press (2006).

XIII. Dosage

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, oral dosage forms such as ingestible solutions, drug release capsules, and the like. The appropriate dosage for the individual subject depends on the therapeutic objectives, the route of administration, and the condition of the patient. Generally, recombinant proteins are dosed at 1-200 mg/kg, e.g., 1-100 mg/kg, e.g., 20-100 mg/kg. Accordingly, it will be necessary for a healthcare provider to tailor and titer the dosage and modify the route of administration as required to obtain the optimal therapeutic effect.

XIV. Indications

The pharmaceutical compositions and methods of the disclosure are useful to reduce inflammation in a subject, to promote clearance of autoantibodies in a subject, to suppress antigen presentation in a subject, to reduce the immune response, e.g., to block immune complex-based activation of the immune response in a subject, and to treat immunological and inflammatory conditions or diseases in a subject. Exemplary conditions and diseases include rheumatoid arthritis (RA); systemic lupus erythematosus (SLE); ANCA-associated vasculitis; antiphospholipid antibody syndrome; autoimmune hemolytic anemia; chronic inflammatory demyelinating neuropathy; clearance of anti-allo in transplant, anti-self in GVHD, anti-replacement, IgG therapeutics, IgG paraproteins; dermatomyositis; Goodpasture's Syndrome; organ system-targeted type II hypersensitivity syndromes mediated through antibody-dependent cell-mediated cytotoxicity, e.g., Guillain Barre syndrome, CIDP, dermatomyositis, Felty's syndrome, antibody-mediated rejection, autoimmune thyroid disease, ulcerative colitis, autoimmune liver disease; idiopathic thrombocytopenia purpura; Myasthenia Gravis, neuromyelitis optica; pemphigus and other autoimmune blistering disorders; Sjogren's Syndrome; autoimmune cytopenias and other disorders mediated through antibody-dependent phagocytosis; other FcR-dependent inflammatory syndromes e.g., synovitis, dermatomyositis, systemic vasculitis, glomerulitis and vasculitis.

EXAMPLES

Example 1—Design and Cloning of DNA Plasmid Constructs

A total of eight DNA plasmid constructs were used to assemble eight Fc constructs (FIGS. 1-7B). The DNA plasmid constructs were transfected into human embryonic kidney (HEK) 293 cells for protein production. The eight encoded secreted polypeptides had the general structures as described below:

A. wt Fc: wild-type Fc domain monomer (FIG. 1: 102 and 104; FIG. 4: 408 and 410).

B. protuberance Fc: Fc domain monomer with engineered protuberance in $C_H3$ antibody constant domain (FIG. 2: 202).

C. cavity Fc: Fc domain monomer with engineered cavity in $C_H3$ antibody constant domain (FIG. 2: 204; FIG. 5: 514 and 516).

C. cavity Fc*: Fc domain monomer with engineered cavity in $C_H3$ antibody constant domain (FIG. 2: 204; FIG. 5: 514 and 516). Cavity Fc* also contains additional amino acid substitutions relative to cavity Fc.

D. charges Fc: Fc domain monomer with reversed charges in $C_H3$ antibody constant domain (FIG. 3: 302 and 304).

E. wt-12-wt Fc2: Two Fc domain monomers joined in series by way of a 12-amino acid GGGS peptide linker (FIG. 4: 402).

F. protuberance-20-charges Fc2: Fc domain monomer with reversed charges in $C_H3$ antibody constant domain and Fc domain monomer with engineered protuberance in $C_H3$ antibody constant domain joined in series by way of a 20-amino acid SGGG peptide linker (FIG. 5: 502 and 508).

F*. protuberance-20-charges Fc2*: Fc domain monomer with reversed charges in $C_H3$ antibody constant domain and Fc domain monomer with engineered protuberance in $C_H3$ antibody constant domain joined in series by way of a 20-amino acid SGGG peptide linker (FIG. 5: 502 and 508). Protuberance-20-charges Fc2* also contains additional amino acid substitutions relative to protuberance Fc.

G. protuberance-20-protuberance Fc2: Two Fc domain monomers both with engineered protuberance in $C_H3$ antibody constant domain joined in series by way of a 20-amino acid GGGS peptide linker (FIG. 6: 602).

H. $C_HC_L$ Fc+: Fc domain monomer with $C_H1$ and $C_L$ constant domains attached to the hinge domain (FIG. 7A: 702 and 704; FIG. 7B: 706, 708, 710, 712, 714, and 716). The $C_L$ constant domain is attached by way of an 18 amino acid GGGS peptide linker to a $C_H$, constant domain.

Fc DNA sequences were derived from human IgG1 Fc. Protuberance, cavity and charges mutations were substituted in the parental Fc sequence. DNA encoding a leader peptide derived from the human immunoglobulin Kappa Light chain was attached to the 5' region. All but one of the polypeptides ($C_HC_L$ Fc+) contained this encoded peptide on the amino terminus to direct protein translocation into the endoplasmic reticulum for assembly and secretion. It will be understood that any one of a variety of leader peptides may be used in connection with the present disclosure. The leader peptide is usually clipped off in the ER lumen. An 11 nucleotide sequence containing a 5' terminal EcoR1 site was added upstream of the ATG start codon. A 30 nucleotide sequence containing a 3' terminal Xho1 site was added downstream of the 3' terminal TGA translation termination codon. The DNA sequences were optimized for expression in mammalian cells and cloned into the pcDNA3.4 mammalian expression vector.

Mutations are denoted by the wild-type amino acid residue followed by the position using the EU Kabat numbering system (Kabat et al., *Sequences of Proteins of Immunological Interest*, National Institutes of Health, Bethesda, Md., ed. 5, 1991) and then the replacement residue in single-letter code. The nucleotide and amino acid sequences of secreted polypeptides A-H described above are provided below (except for cavity Fc* and protuberance-20-charges Fc2*, for which only the amino acid sequences are provided).

Wt Fc
SEQ ID NO: 29:
GACAAGACCCACACCTGTCCGCCTTGCCCTGCCCCTGAGCTG CTGGGAGGCCCCAGCGTGTTCCTGTTCCCCCCAAA GCCCAAG GACACCCTGATGATCAGCCGGACCCCCGAAGTGACCTGCGTG GTGGTGGACGTGTCCCACGAGGACCCTGAAGTGAAGTTCAATT GGTACGTGGACGGCGTGGAAGTGCACAACGCCAAGACCAAGC CCAGAGAGGAACAGTACAACAGCACCTACCGGGTGGTGTCCG TGCTGACCGTGCTGCACCAGGACTGGCTGAACGGCAAAGAAT ACAAGTGCAAAGTCTCCAACAAGGCCCTGCCTGCCCCCATCGA GAAAACCATCAGCAAGGCCAAGGGCCAGCCCCGCGAGCCCCA GGTGTACACACTGCCCCCCAGCCGGGACGAGCTGACCAAGAA CCAGGTGTCCCTGACCTGCCTGGTGAAAGGCTTCTACCCCAGC GATATCGCCGTGGAATGGGAGAGCAACGGCCAGCCCGAGAAC AACTACAAGACCACCCCCCCTGTGCTGGACAGCGACGGCTCAT TCTTCCTGTACAGCAAGCTGACCGTGGACAAGAGCCGGTGGC AGCAGGGCAACGTGTTCAGCTGCAGCGTGATGCACGAGGCC TGCACAACCACTACACCCAGAAGTCCCTGAGCCTGAGCCCCG GCAAG

SEQ ID NO: 30:
DKTHTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPSR DELTKNQVSLTCLVKGFYPSDIAVEWESNGQPENNYKTTPPVLDS DGSFFLYSKLTVDKSRWQQGNVFSCSVMHEALHNHYTQKSLSLS PGK protuberance Fc
SEQ ID NO: 31:
GACAAGACCCACACCTGTCCGCCTTGCCCTGCCCCTGAGCTG CTGGGAGGCCCCAGCGTGTTCCTGTTCCCCCCAAA GCCCAAG GACACCCTGATGATCAGCCGGACCCCCGAAGTGACCTGCGTG GTGGTGGACGTGTCCCACGAGGACCCTGAAGTGAAGTTCAATT GGTACGTGGACGGCGTGGAAGTGCACAACGCCAAGACCAAGC CCAGAGAGGAACAGTACAACAGCACCTACCGGGTGGTGTCCG TGCTGACCGTGCTGCACCAGGACTGGCTGAACGGCAAAGAAT ACAAGTGCAAAGTCTCCAACAAGGCCCTGCCTGCCCCCATCGA GAAAACCATCAGCAAGGCCAAGGGCCAGCCCCGCGAGCCCCA GGTGTACACACTGCCCCCCTGCCGGGACGAGCTGACCAAGAA CCAGGTGTCCCTGTGGTGCCTGGTGAAAGGCTTCTACCCCAG CGATATCGCCGTGGAATGGGAGAGCAACGGCCAGCCCGAGAA CAACTACAAGACCACCCCCCCTGTGCTGGACAGCGACGGCTC ATTCTTCCTGTACAGCAAGCTGACCGTGGACAAGAGCCGGTGG CAGCAGGGCAACGTGTTCAGCTGCAGCGTGATGCACGAGGCC CTGCACAACCACTACACCCAGAAGTCCCTGAGCCTGAGCCCC GGCAAG SEQ ID NO: 32:
DKTHTCPPCPAPELLGGPSVFLFPPKPKDTLMISRTPEVTCVVVD VSHEDPEVKFNVVYVDGVEVHNAKTKPREEQYNSTYRVVSVLTVL HQDVVLNGKEYKCKVSNKALPAPIEKTISKAKGQPREPQVYTLPPC RDELTKNQVSLWCLVKGFYPSDIAVEWESNGQPENNYKTTPPVL DSDGSFFLYSKLTVDKSRWQQGNVFSCSVMHEALHNHYTQKSLS LSPGK Cavity Fc
SEQ ID NO: 33:
GACAAGACCCACACCTGTCCGCCTTGCCCTGCCCCTGAGCTG CTGGGAGGCCCCAGCGTGTTCCTGTTCCCCCCAAA GCCCAAG GACACCCTGATGATCAGCCGGACCCCCGAAGTGACCTGCGTG GTGGTGGACGTGTCCCACGAGGACCCTGAAGTGAAGTTCAATT GGTACGTGGACGGCGTGGAAGTGCACAACGCCAAGACCAAGC CCAGAGAGGAACAGTA CAACAGCACCTACCGGGTGGTGTCCGTGCTGACCGTGCTGCACCAGGACTGGCTGAACGGCAAAGAAT ACAAGTGCAAAGTCTCCAACAAGGCCCTGCCTGCCCCCATCGAGAAAACCATCAGCAAGGCCAAGGGCCAGCCCCGCGAGCCCCAAGTGTGTACACTGCCCCCCAGCCGGGACGAGCTGACCAAGAA CCAGGTGTCCCTGAGCTGCGCCGTGAAAGGCTTCTACCCCAGCGATATCGCCGTGGAATGGGAGAGCAACGGCCAGCCCGAGAA CAACTACAAGACCACCCCCCCTGTGCTGGACAGCGACGGCTCATTCTTCCTGGTTAGCAAGCTGACCGTGGACAAGAGCCGGTGGCAGCAGGGCAACGTGTTCAGCTGCAGCGTGATGCACGAGGCC CTGCACAACCACTACACCCAGAAGTCCCTGAGCCTGAGCCCCGGCAAG SEQ ID NO: 34:
DKTHTCPPCPAPELLGGPSVFLFPPKPKDTLMISRTPEVTCVVVDV SHEDPEVKFNWYVDGVEVHNAKTKPREEQYNSTYRVVSVLTVLH QDVVLNGKEYKCKVSNKALPAPIEKTISKAKGQPREPQVCTLPPSR DELTKNQVSLSCAVKGFYPSDIAVEWESNGQPENNYKTTPPVLDS DGSFFLVSKLTVDKSRWQQGNVFSCSVMHEALHNHYTQKSLSLS PGK Cavity Fc*
SEQ ID NO: 45:
DKTHTCPPCPAPELLGGPSVFLFPPKPKDTLMISRTPEVTCVVVD VSHEDPEVKFNVVYVDGVEVHNAKTKPREEQYNSTYRVVSVLTVL HQDVVLNGKEYKCKVSNKALPAPIEKTISKAKGQPREPQVCTLPPS RDELTKNQVSLSCAVEGFYPSDIAVEWESNGQPENNYKTTPPVLD SDGSFFLVSKLTVDKSRWQQGNVFSCSVMHEALHNHYTQKSLSL SPGK Cavity Fc
SEQ ID NO: 47:
GACAAGACCCACACCTGTCCGCCTTGCCCTGCCCCTGAGCTGCTGGGAGGCCCCAGCGTGTTCCTGTTCCCCCCAAAGCCCAAGGACACCCTGATGATCAGCCGGACCCCCGAAGTGACCTGCGTGGTGGTGGACGTGTCCCACGAGGAC CCTGAAGTGAAGTTCAATTGGTACGTGGACGGCGTGGAAGTGCACAACGC CAAGACCAAGCCCAGAGAGGAACAGTACAACAGCACCTACCGGGTGGTGTCCGTGCTGACCGTGCTGCACCAGGACTGGCTGAACGGCAAAGAATACAAG TGCAAAGTCTCCAACAAGGCCCTGCCTGCCCCCATCGAGAAAACCATCAGCAAGGCCAAGGGCCAGCCCCGCGAGCCCCAAGTGTGTACACTGCCCCCAGCCGGGACGAGCTGACCAAGAACCAGGTGTCCCTGAGCTGCGCCGTGGAC GGCTTCTACCCCAGCGATATCGCCGTGGAATGGGAGAGCAACGGCCAGCCCGAGAACAACTACAAGACCACCCCCCCTGTGCTGGACAGCGACGGCTCATTCTTCCTGGTTAGCAAGCTGACCGTGGACAAGAGCCGGTGGCAGCAGGGCAACGTGTTCAGCTGCAGCGTGATGCACGAGGCCCTGCACAACCACTACACCCAGAAGTCCCTGAGCCTGAGCCCCGGCTAG SEQ ID NO: 48:
DKTHTCPPCPAPELLGGPSVFLFPPKPKDTLMISRTPEVTCVVVDVSHED PEVKFNVVYVDGVEVHNAKTKPREEQYNSTYRVVSVLTVLHQDVVLNGKEYK CKVSNKALPAPIEKTISKAKGQPREPQVCTLPPSRDELTKNQVSLSCAVD GFYPSDIAVEWESNGQPENNYKTTPPVLDSDGSFFLVSKLTVDKSRWQQG NVFSCSVMHEALHNHYTQKSLSLSPG Charges Fc
SEQ ID NO: 35:
GACAAGACCCACACCTGTCCGCCTTGCCCTGCCCCTGAGCTG CTGGGAGGCCCCAGCGTGTTCCTGTTCCCCCCAAAGCCCAAG GACACCCTGATGATCAGCCGGACCCCCGAAGTGACCTGCGTG GTGGTGGACGTGTCCCACGAGGACCCTGAAGTGAAGTTCAATT GGTACGTGGACGGCGTGGAAGTGCACAACGCCAAGACCAAGC CCAGAGAGGAACAGTACAACAGCACCTACCGGGTGGTGTCCG TGCTGACCGTGCTGCACCAGGACTGGCTGAACGGCAAAGAAT ACAAGTGCAAAGTCTCCAACAAGGCCCTGCCTGCCCCCATCGA GAAAACCATCAGCAAGGCCAAGGGCCAGCCCCGCGAGCCCCA GGTGTACACTGCCCCCCAGCCGGGACGAGCTGACCAAGAA CCAGGTGTCCCTGACCTGCCTGGTGAAAGGCTTCTACCCCAGC GATATCGCCGTGGAATGGGAGAGCAACGGCCAGCCCGAGAAC AACTACAAGACCACCCCCCCTGTGCTGAAAAGCGACGGCTCAT TCTTCCTGTACAGCGACCTGACCGTGGACAAGAGCCGGTGGC AGCAGGGCAACGTGTTCAGCTGCAGCGTGATGCACGAGGCC TGCACAACCACTACACCCAGAAGTCCCTGAGCCTGAGCCCCG GCAAG SEQ ID NO: 36:
DKTHTCPPCPAPELLGGPSVFLFPPKPKDTLMISRTPEVTCVVVDV SHEDPEVKFNWYVDGVEVHNAKTKPREEQYNSTYRVVSVLTVLH QDVVLNGKEYKCKVSNKALPAPIEKTISKAKGQPREPQVYTLPPSR DELTKNQVSLTCLVKGFYPSDIAVEWESNGQPENNYKTTPPVLKS DGSFFLYSDLTVDKSRWQQGNVFSCSVMHEALHNHYTQKSLSLS PGK wt-12-wt Fc2
SEQ ID NO: 37:
GACAAGACCCACACCTGTCCCCCTTGCCCTGCCCCTGAGCTG CTGGGAGGCCCCAGCGTGTTCCTGTTCCCCCCAAAGCCCAAG GACACCCTGAT GATCAGCCGGACCCCCGAAGTGACCTGCGTG
GTGGTGGACGTGTCCCACGAGGACCCT-
GAAGTGAAGTTCAATT
GGTACGTGGACGGCGTGGAAGTGCACAACGC-
CAAGACCAAGC CCAGAGAGGAACAGTA-
CAACAGCACCTACCGGGTGGTGTCCG
TGCTGACCGTGCTGCACCAGGACTGGCT-
CAACGGCAAAGAGT ACAAGTGCAAGGTGTC-
CAACAAGGCCCTGCCTGCCCCCATCG
AGAAAACCATCAGCAAGGC-
CAAGGGCCAGCCCCGCGAGCCCC AGGTCTA-
CACACTGCCCCCAGCCGGGACGAGCTGAC-
CAAGA
ACCAGGTCTCCCTGACCTGCCTGGT-
GAAAGGCTTCTACCCCAG CGATATCGCCGTG-
GAATGGGAGAGCAACGGCCAGCCCGAGAA
CAACTACAAGAC-
CACCCCCCCTGTGCTGGACAGCGACGGCTC
ATTCTTCCTGTA-
CAGCAAGCTGACCGTGGACAAGAGCCGGTGG
CAGCAGGGCAACGTGTTCAGCTGCAGCGT-
GATGCACGAGGCC CTGCACAACCACTA-
CACCCAGAAGTCCCTGAGCCTGAGCCCC
GGCAAAGGCGGGGGATCTGGGGGAG-
GAAGCGGAGGCGGCAG CGATAAGACCCAT-
ACCTGCCCTCCCTGTCCGCTCCCGAACTG
CTGGGGGGACCCTCCGTGTTTCTGTTTC-
CACCTAAGCCTAAGG ATACGCTCAT-
GATCTCCAGAACCCCTGAAGTCA-
CATGTGTGGT
GGTCGATGTGTCTCATGAAGATCCCGAAGT-
CAAGTTTAACTGG TATGTG-
GATGGGGTCGAGGTCCACAATGC-
CAAAACAAAGCCTC
GGGAAGAACAGTATAACTCCACCTA-
CAGAGTCGTCAGCGTGCT GACAGTCCTT-
CATCAGGATTGGCTGAATGGGAAAGAGTA-
CAAA
TGTAAAGTGTCTAACAAAGCTCTGCCCGCTCC-
TATCGAAAAGA CCATCTCCAAAGC-
CAAAGGGCAGCCCAGAGAACCTCAGGTGTA
CACCCTGCCACCCTCCAGAGAT-
GAGCTGACAAAAAATCAGGTG TCACTGA-
CATGTCTGGTGAAAGGGTTTTATCCCTCCGA-
CATTGC
TGTGGAATGGGAATCCAATGGGCAGCCT-
GAAAACAATTATAAG
ACAACACCTCCCGTGCTGGACTCCGATGGCT-
CATTTTTTCTGTA CTCTAAACTGACAGTGGA-
TAAGTCCAGATGGCAGCAGGGAAAT
GTGTTTTCCTGCTCTGTGATGCAT-
GAAGCTCTGCATAATCACTA
TACACAGAAAAGCCTGTCCCTGTCCCCGGCA
AG SEQ ID NO: 38:
DKTHTCPPCPAPELLGGPSVFLFPPKPKDTLMISRTPEVTCVVVDV SHEDPE-
VKFNWYVDGVEVHNAKTKPREEQYN-
STYRVVSVLTVLH
QDVVLNGKEYKCKVSNKALPA-
PIEKTISKAKGQPREPQVYTLPPSR DELT-
KNQVSLTCLVKGFYPSDIAVEWESNGQPEN-
NYKTTPPVLDS
DGSFFLYSK-
LTVDKSRWQQGNVFSCSVMHEALHN-
HYTQKSLSLS PGKGGGSGGGSGGGSDKTH-
TCPPCPAPELLGGPSVFLFPPKPK DTLMISRTPEVTCVVVDVSHEDPEVKFNV-
VYVDGVEVHNAKTKPR EEQYN-
STYRVVSVLTVLHQDWLNGKEYKCKVSNKAL-
PAPIEKTISK
AKGQPREPQVYTLPPSRDELTKNQVSLT-
CLVKGFYPSDIAVEWES NGQPEN-
NYKTTPPVLDSDGSFFLYSK-
LTVDKSRWQQGNVFSCSV
MHEALHNHYTQKSLSLSPGK Protuberance-20-Charges Fc2
SEQ ID NO: 39:
GACAAGACC-
CACACCTGTCCCCCTTGCCCAGCCCCT-
GAGCTG CTGG-
GAGGCCCCAGCGTGTTCCTGTTCCCCCCAAA
GCCCAAG GACACCCTGAT-
GATCAGCCGGACCCCCGAAGTGACCTGCGTG
GTGGTGGACGTGTCCCACGAGGACCCT-
GAAGTGAAGTTCAATT
GGTACGTGGACGGCGTGGAAGTGCACAACGC-
CAAGACCAAGC CCAGAGAGGAACAGTA-
CAACAGCACCTACCGGGTGGTGTCCG
TGCTGACCGTGCTGCACCAGGACTGGCT-
GAACGGCAAAGAGT ACAAGTGCAAGGTGTC-
CAACAAGGCCCTGCCTGCCCCCATCG
AGAAAACCATCAGCAAGGC-
CAAGGGCCAGCCCCGCGAGCCCC AGGTGTA-
CACCCTGCCCCCTTGCAGAGATGAGCTGAC-
CAAGAA
CCAGGTGTCCCTGTGGTGCCTGGT-
CAAGGGCTTCTACCCCAG CGATATCGCCGTG-
GAATGGGAGAGCAACGGCCAGCCCGAGAA
CAACTACAAGAC-
CACCCCCCCTGTGCTGGACAGCGACGGCTC
ATTCTTCCTGTA-
CAGCAAGCTGACCGTGGACAAGAGCCGGTGG
CAGCAGGGCAACGTGTTCAGCTGCAGCGT-
GATGCACGAGGCC CTGCACAACCACTA-
CACCCAGAAGTCCCTGAGCCTGAGCCCC
GGCAAGTCTGGGGGAGGATCAGGGGGTG-
AAGTGGCGGTGG ATCTGGTGGTGGAAGCG-
GAGGCGGCGATAAGACACACACATG
CCCCCCCTGTCCAGCTCCCGAACTGCTGGGG
GGACCCTCCGT GTTTCTGTTTC-
CACCTAAGCCTAAGGATACGCTCATGATCTCCA
GAACCCCTGAAGTCACATGTGTGGTGGTC-
GATGTGTCTCATGA AGATCCCGAAGTCAAGTT-
TAATTGGTATGTCGATGGGGTCGAG
GTGCACAATGCCAAAACAAAACCTCGG-
GAAGAACAGTATAACT CCACATA-
CAGAGTGGTGTCTGTCCTCACAGTCCTG-
CATCAGGA
TTGGCTCAATGGGAAAGAGTA-
CAAATGTAAAGTCTCTAACAAG
GCTCTCCCCGCTCCGATCGAAAAGACCATCTC-
CAAAGCCAAAG
GGCAGCCCAGAGAACCTCAGGTCTA-
CACACTGCCTCCCAGCC
GGGACGAGCTGACAAAAAAT-
CAAGTGTCTCTGACCTGCCTCGT
GAAGGGCTTTTATCCCTCCGACAT-
TGCCGTCGAGTGGGAGTCC AATGGACAGCCG-
GAAAACAATTATAAGACCACGCCTCCAGTGC
TGAAGTCCGACGGCAGCTTCTTTCTGTACTCC
GACCTGACAGT GGATAAGTCCA-
GATGGCAGCAAGGGAATGTGTTCCTGTTCC
GTGATGCATGAAGCCCTCCATAATCAC- SEQ ID NO: 40:
DKTHTCPPCPAPELLGGPSVFLFPPKPKDTLMISRTPEVTCVVVDVSHEDPEVKFNWYVDGVEVHNAKTKPREEQYNSTYRVVSVLTVLHQDVVLNGKEYKCKVSNKALPAPIEKTISKAKGQPREPQVYTLPPCR DELTKNQVSLWCLVKGFYPSDIAVEWESNGQPENNYKTTPPVLDSDGSFFLYSKLTVDKSRWQQGNVFSCSVMHEALHNHYTQKSLSLSPGKSGGGSGGGSGGGSGGGSGGGDKTHTCPPCPAPELLGGP SVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFY PSDIAVEWESNGQPENNYKTTPPVLKSDGSFFLYSDLTVDKSRWQQGNVFSCSVMHEALHNHYTQKSLSLSPGK Protuberance-20-Charges Fc2*

SEQ ID NO: 46:
DKTHTCPPCPAPELLGGPSVFLFPPKPKDTLMISRTPEVTCVVVDVSHEDPEVKFNWYVDGVEVHNAKTKPREEQYNSTYRVVSVLTVLHQDVVLNGKEYKCKVSNKALPAPIEKTISKAKGQPREPQVYTLPPCR DKLTKNQVSLWCLVKGFYPSDIAVEWESNGQPENNYKTTPPVLDSDGSFFLYSKLTVDKSRWQQGNVFSCSVMHEALHNHYTQKSLSLSPGKSGGGSGGGSGGGSGGGSGGGDKTHTCPPCPAPELLGGP SVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFY PSDIAVEWESNGQPENNYKTTPPVLKSDGSFFLYSDLTVDKSRWQQGNVFSCSVMHEALHNHYTQKSLSLSPGK protuberance-20-protuberance Fc2

SEQ ID NO: 41:
GACAAGACCCACACCTGTCCCCCTTGCCCTGCCCTGAGCTG CTGGGAGGCCCCAGCGTGTTCCTGTTCCCCCCAAAGCCCAAG GACACCCTGATGATCAGCCGGACCCCCGAAGTGACCTGCGTGGTGGTGGACGTGTCCCACGAGGACCCTGAAGTGAAGTTCAATTGGTACGTGGACGGCGTGGAAGTGCACAACGCCAAGACCAAGC CCAGAGAGGAACAGTACAACAGCACCTACCGGGTGGTGTCCGTGCTGACCGTGCTGCACCAGGACTGGCTGAACGGCAAAGAGT ACAAGTGCAAGGTGTCCAACAAGGCCCTGCCTGCCCCATCGAGAAAACCATCAGCAAGGCCAAGGGCCAGCCCCGCGAGCCCC AGGTGTACACCCTGCCCCCTTGCAGAGATGAACTGACCAAGAA CCAGGTGTCCCTGTGGTGCCTGGTCAAGGGCTTCTACCCCAG CGATATCGCCGTGGAATGGGAGAGCAACGGCCAGCCCGAGAACAACTACAAGACCACCCCCCCTGTGCTGGACAGCGACGGCTCATTCTTCCTGTACAGCAAGCTGACCGTGGACAAGAGCCGGTGGCAGCAGGGCAACGTGTTCAGCTGCAGCGTGATGCACGAGGCC CTGCACAACCACTACACCCAGAAGTCCCTGAGCCTGAGCCCCGGCAAGTCTGGGGGAGGATCAGGGGGTGGAAGTGGCGGTGG ATCGGTGGTGGAAGCGGAGGCGGCGATAAGACACACACATGCCCCCCCTGTCCAGCTCCCGAACTGCTGGGGGGACCCTCCGT GTTTCTGTTTCCACCTAAGCCTAAGGATACGCTCATGATCTCCAGAACCCCTGAAGTCACATGTGTGGTGGTCGATGTGTCTCATGA AGATCCCGAAGTCAAGTTTAACTGGTATGTGGATGGGGTCGAG GTCCACAATGCCAAAACAAAGCCTCGGGAAGAACAGTATAACT CCACCTACAGAGTCGTCAGCGTGCTGACAGTCCTGCATCAAGA TTGGCTCAATGGGAAAGAGTATAAGTGTAAAGTCTCGAACAAAGCCCTCCCCGCTCCTATCGAAAAGACCATCTCCAAAGCCAAAGGGCAGCCCAGAGAACCTCAGGTCTACACACTGCCTCCATGTCGGGACGAGCTGACAAAAAATCAGGTGTCACTGTGGTGTCTGGTG AAGGGGTTTACCCTTCCGACATTGCTGTGGAATGGGAATCCAATGGGCAGCCTGAAAACAATTATAAGACAACACCTCCCGTGCT GGACTCCGATGGCTCATTTTTTCTGTACTCTAAACTGACAGTGG ATAAGTCCAGATGGCAGCAGGGAAATGTGTTTTCCTGCTCTGT GATGCATGAAGCTCTGCATAATCACTATACACAGAAAAGCCTGT CCCTGTCCCCTGGCAAG

SEQ ID NO: 42:
DKTHTCPPCPAPELLGGPSVFLFPPKPKDTLMISRTPEVTCVVVDVSHEDPEVKFNWYVDGVEVHNAKTKPREEQYNSTYRVVSVLTVLHQDVVLNGKEYKCKVSNKALPAPIEKTISKAKGQPREPQVYTLPPCR DELTKNQVSLWCLVKGFYPSDIAVEWESNGQPENNYKTTPPVLDSDGSFFLYSKLTVDKSRWQQGNVFSCSVMHEALHNHYTQKSLSLSPGKSGGGSGGGSGGGSGGGSGGGDKTHTCPPCPAPELLGGP SVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFY PSDIAVEWESNGQPENNYKTTPPVLDSDGSFFLYSKLTVDKSRWQQGNVFSCSVMHEALHNHYTQKSLSLSPGK Protuberance-20-Charges Fc2

SEQ ID NO: 49:
GACAAGACCCACACCTGTCCCCCTTGCCCAGCCCCTGAGCTGCTGGGAGGCCCCAGCGTGTTCCTGTTCCCCCCAAAGCCCAAGGACACCCTGATGATCA

GCCGGACCCCCGAAGTGACCTGCGTGGTGGTGGACGTGTCCCACGAGGAC CCTGAAGTGAAGTTCAATTGGTACGTGGACGGCGTGGAAGTGCACAACGC CAAGACCAAGCCCAGAGAGGAACAGTACAACAGCACCTACCGGGTGGTGT CCGTGCTGACCGTGCTGCACCAGGACTGGCTGAACGGCAAAGAGTACAAG TGCAAGGTGTCCAACAAGGCCCTGCCTGCCCCCATCGAGAAAACCATCAG CAAGGCCAAGGGCCAGCCCCGCGAGCCCCAGGTGTACACCCTGCCCCCTT GCAGAGATAAGCTGACCAAGAACCAGGTGTCCCTGTGGTGCCTGGTCAAG GGCTTCTACCCCAGCGATATCGCCGTGGAATGGGAGAGCAACGGCCAGCC CGAGAACAACTACAAGACCACCCCCCCTGTGCTGGACAGCGACGGCTCAT TCTTCCTGTACAGCAAGCTGACCGTGGACAAGAGCCGGTGG CAGCAGGGC AACGTGTTCAGCTGCAGCGTGATGCACGAGGCCCTGCACAACCACTACAC CCAGAAGTCCCTGAGCCTGAGCCCCGGCAAGGGAGGGGGAGGAGGAGGGG GTGGAGGTGGCGGTGGAGGCGGTGGTGGAGGCGGAGGCGGCGATAA GACA CACACATGCCCCCCTGTCCAGCTCCCGAACTGCTGGGGGGACCCTCCGT GTTTCTGTTTCCACCTAAGCCTAAGGATACGCTCATGATCTCCAGAACCC CTGAAGTCACATGTGTGGTGGTCGATGTGTCTCATGAAGATCCCGAAGTC AAGTTTAATTGGTATGTCGATGGGGTCGAGGTGCACAATGCCAAAACAAA ACCTCGGGAAGAACAGTATAACTCCACATACAGAGTGGTGTCTGTCCTCA CAGTCCTGCATCAGGATTGGCTCAATGGGAAAGAGTACAAATGTAAAGTC TCTAACAAGGCTCTCCCCGCTCCGATCGAAAAGACCATCTCCAAAGCCAA AGGGCAGCCCAGAGAACCTCAGGTCTACACACTGCCTCCCAGCCGGGACG AGCTGACAAAAAATCAAGTGTCTCTGACCTGCCTCGTGAAGGGCTTTTAT CCCTCCGACATTGCCGTCGAGTGGGAGTCCAATGGACAGCCGGAAAACAA TTATAAGACCACGCCTCCAGTGCTGAAGTCCGACGGCAGCTTCTTTCTGT ACTCCGACCTGACAGTGGATAAGTCCAGATGGCAGCAAGGGAATGTGTTC TCCTGTTCCGTGATGCATGAAGCCCTCCATAATCACTATACCCAGAAAAG CCTGTCCCTGTCCCTGGCTAG

SEQ ID NO: 50:
DKTHTCPPCPAPELLGGPSVFLFPPKPKDTLMISRTPEVTCVVVDVSHED PEVKFNVVYVDGVEVHNAKTKPREEQYNSTYRVVSVLTVLHQDVVLNGKEYK CKVSNKALPAPIEKTISKAKGQPREPQVYTLPPCRDKLTKNQVSLWCLVK GFYPSDIAVEWESNGQPENNYKTTPPVLDSDGSFFLYSKLTVDKSRWQQG NVFSCSVMHEALHNHYTQKSLSLSPGKGGGGGGGGGGGGGGGGGGGDKT HTCPPCPAPELLGGPSVFLFPPKPKDTLMISRTPEVTCVVVDVSHEDPEV KFNVVYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFY PSDIAVEWESNGQPENNYKTTPPVLKSDGSFFLYSDLTVDKSRWQQGNVF SCSVMHEALHNHYTQKSLSLSPG $C_H C_L$ Fc+

SEQ ID NO: 43:
AGGACAGTGGCCGCTCCCAGCGTGTTCATCTTCCCACCCAGCGACGAGCA GCTGAAGTCCGGCACAGCCAGCGTGGTCTGCCTGCTGAACAACTTCTACC CCCGCGAGGCCAAGGTGCAGTGGAAGGTGGACAACGCCCTGCAGAGCGGC AACAGCCAGGAAAGCGTCACCGAGCAGGACAGCAAGGACTCCACCTACAG CCTGTCTAGCACCCTGACCCTGAGCAAGGCCGACTACGAGAAGCACAAGG TGTACGCCTGCGAAGTGACCCACCAGGGCCTGTCCAGCCCCGTGACCAAG AGCTTCAACAGAGGCGAGTGCGGCGGCTCTGGCGAGGATCCGGGGGAGG ATCAGGCGGCGAAGCGGAGGCAGCGCTAGCACAAAGGGCCCCTCCGTGT TCCCCCTGGCCCCCAGCAGCAAGAGCACATCTGGCGGAACAGCCGCCCTG GGCTGCCTGGTGAAAGACTACTTCCCCGAGCCCGTGACCGTGTCCTGGAA CTCTGGCGCCCTGACCAGCGGCGTGCACACCTTCCAGCCGTGCTGCAGA GCAGCGGCCTGTACTCCCTGAGCAGCGTGGTGACAGTGCCTAGCAGCAGC CTGGGCACCCAGACCTACATCTGCAACGTGAACCACAAGCCCAGCAACAC CAAAGTGGACAAGCGGGTGGAACCCAAGAGCTGCGACAAGACCCACACGT GTCCCCCCTGCCCAGCCCCTGAACTGCTGGGCGGACCTAGCGTGTTCCTG TTCCCCCCAAAGCCCAAGGACACCCTGATGATCAGCCGGACCCCCGAAGT GACCTGCGTGGTGGTGGACGTGTCCCACGAGGACCCTGAAGTGAAGTTCA ATTGGTACGTGGACGGCGTGGAAGTGCACAATGCCAAGACCAAGCCCAGA GAGGAACAGTACAACAGCACCTACCGGGTGGTGTCCGTGCTGACCGTGCT GCACCAGGACTGGCTGAACGGCAAAGAGTACAAGTGCAAGGTCTCCAACA AGGCCCTGCCTGCCCCCATCGAGAAAACCATCAGCAAGGCCAAGGGCCAG CCCCGCGAGCCCCAGGTGTACACACTGCCCCCAGCCGGGACGAGCTGAC CAAGAACCAGGTGTCCCTGACCTGTCTGGTGAAAGGCTTCTACCCCTCCG ATATCGCCGTGGAATGGGAGAGCAACGGCCAGCCCGAGAACAACTACAAG ACCACCCCCCCTGTGCTGGACTCCGACGGCTCATTCTTCCTGTACAGCAA GCTGACCGTGGACAAGAGCCGGTGGCAGCAGGGCAACGTGTTCAGCTGCT CCGTGATGCACGAGGCCCTGCACAACCACTACACCCAGAAGTCCCTGAGC CTGAGCCCCGGCAAA

SEQ ID NO: 44:
RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSFNRGECGGSGGGSGGGSGGGS GGSASTKGPS VFPLAPSSKSTSGGTAALGCLVKDYFPEPVTVSWNSGALTSGVHT FPAVLQSSGLYSLSSVVTVPSSSLGTQTYICNVNHKPSNTKVDKR VEPKSCDKTHTCPPCPAPELLGGPSVFLFPPKPKDTLMISRTPEVT CVVVDVSHEDPEVKFNVVYVDGVEVHNAKTKPREEQYNSTYRVVS VLTVLHQDWLNGKEYKCKVSNKALPAPIEKTISKAKGQPREPQVY TLPPSRDELTKNQVSLTCLVKGFYPSDIAVEWESNGQPENNYKTT PPVLDSDGSFFLYSKLTVDKSRWQQGNVFSCSVMHEALHNHYTQ KSLSLSPGK

In some embodiments, the Fc polypeptides in the Fc constructs described herein comprise, consist of, or consist essentially of any of the sequences described herein with up to 10 (e.g., up to 9, 8, 7, 6, 5, 4, 3, 2, or 1) single amino acid modifications (e.g., substitutions, e.g., conservative substitutions).

In some embodiments, one or more Fc polypeptides in an Fc construct contain a terminal lysine residue. In some embodiments, one or more Fc polypeptides in an Fc construct do not contain a terminal lysine residue. In some embodiments, all of the Fc polypeptides in an Fc construct contain a terminal lysine residue. In some embodiments, all of the Fc polypeptides in an Fc construct do not contain a terminal lysine residue. In one example, the terminal lysine residue in an Fc polypeptide comprising, consisting of, or consisting essentially of the sequence of any one of SEQ ID NOs: 30, 32, 34, 36, 38, 40, 42, 44, 45, and 46 may be removed to generate a corresponding Fc polypeptide that does not contain a terminal lysine residue. In another example, a terminal lysine residue may be added to an Fc polypeptide comprising, consisting of, or consisting essentially of the sequence of SEQ ID NO: 48 or 50 to generate a corresponding Fc polypeptide that contains a terminal lysine residue.

Example 2—Expression of Fc Construct Proteins

For protein expression of the Fc constructs, two of the DNA plasmid constructs selected from A-H described in Example 1 were transfected into EXPI293 cells (LifeTechnologies). Liposome transfection was used to introduce plasmid DNA into EXPI293 cells. The total amount of transfected plasmid constructs was fixed whereas the ratio of different plasmid constructs was varied to maximize the yield of desired constructs (see Table 11 below). For each Fc construct, the ratio (by mass) of the two transfected DNA plasmid constructs is shown in Table 11. Illustrations of the constructs are shown FIGS. 1-7B.

After protein expression, the expressed constructs were purified from the cell culture supernatant by Protein A-based affinity column chromatography. Media supernatants were loaded onto a Poros MabCapture A (LifeTechnologies) column using an AKTA Avant preparative chromatography system (GE Healthcare Life Sciences). Captured Fc constructs were then washed with phosphate buffered saline (low-salt wash) followed by phosphate buffered saline supplemented with 500 mM NaCl (high-salt wash). Fc constructs are eluted with 100 mM glycine, 150 mM NaCl, pH 3 buffer. The protein solution emerging from the column is neutralized by addition of 1M TRIS pH 7.4 to a final concentration of 100 mM. The Fc constructs were further fractionated by ion exchange chromatography using Poros® XS resin (Applied Biosciences Cat. #4404336). The column was pre-equilibrated with 10 mM MES, pH 6 (buffer A), and the sample was eluted with a gradient against 10 mM MES, 500 mM sodium chloride, pH 6 (buffer B).

We obtained a total of seven Fc constructs (see Table 11 below and FIGS. 1-7B). Purified Fc constructs were analyzed by SDS-PAGE (sodium dodecyl sulfate polyacrylamide gel electrophoresis) under both reducing and non-reducing conditions followed by Coomassie Blue staining to confirm the presence of protein bands of expected size.

TABLE 11

| Construct | Plasmids Transfected | Ratio of Plasmids A:B | Approx. MW in kDa (reducing SDS-Page) | Approx. MW in KDa (non-reducing SDS-Page) |
| --- | --- | --- | --- | --- |
| 1 | A: Wt Fc | n/a | 25 | 50 |
| 2 | A: Protuberance Fc<br>B: Cavity Fc | 1:1 | 25 | 50 |
| 3 | A: Charges Fc | | 25 | 50 |
| 4 | A: Wt-12-Wt Fc2<br>B: Wt FC | 1:2 | 25, 50 | 100 |
| 5 | A: Protuberance-20-Charges Fc2<br>B: Cavity Fc | 2:1 | 25, 50 | 150 |
| 5* | A: Protuberance-20-Charges Fc2*<br>B: Cavity Fc* | 2:1 | 25, 50 | 150 |
| 6 | A: Protuberance-20-Protuberance Fc2<br>B: Cavity Fc | 1:1 | 25, 50 | 100 |
| 7 and 8 | A: Ch, Cl, Fc+ | n/a | 50 | 100 |

Example 3—Preparation and SDS-PAGE Analysis of Construct 4

Figures 11A, 11B:
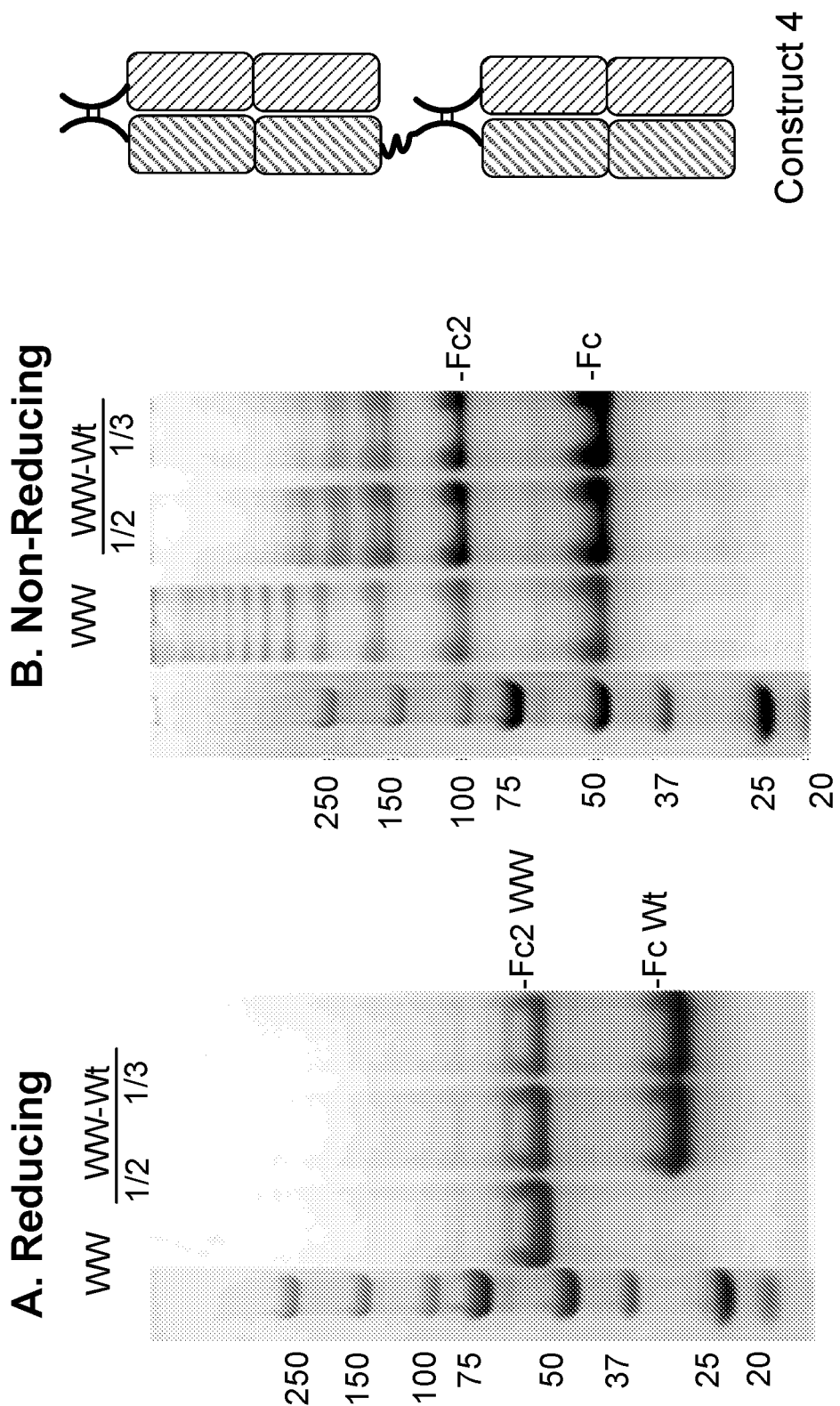
FIGS. 11A-11B show reducing and non-reducing SDS-PAGE of construct 4, respectively.

Two DNA plasmid constructs, wt-12-wt Fc2 (DNA plasmid construct E in Example 1) and wt Fc (DNA plasmid construct A in Example 1), were used to express construct 4 (FIG. 4). The two plasmid constructs were transfected into HEK 293 cells for protein expression and purification as described in Example 2. FIG. 11A-B shows the reducing and non-reducing SDS-PAGE of construct 4. On reducing SDS-PAGE (FIG. 11A), we observed a band at approximately 25 kDa (lanes 2 and 3, FIG. 11A) corresponding to the wt Fc domain monomer and a band at 50 kDa corresponding to the wt-12-wt Fc2 tandem dimer (lanes 1-3, FIG. 11A). On non-reducing SDS-PAGE (FIG. 11B), lanes 2 and 3 each contain the final protein product of construct 4 in higher (½) and lower (⅓) protein amounts, respectively. We observed one major band at approximately 100 kDa corresponding to the association of wt-12-wt Fc2 tandem dimer with two wt Fc domain monomers to form construct 4, and another major band of approximately equal signal intensity at approximately 50 kDa corresponding to free wt-12-wt Fc2 tandem dimer that is not joined with wt Fc domain monomers.

In addition, we observed higher molecular weight bands at approximately 150 kDa, 200 kDa and 250 kDa (lanes 2 and 3, FIG. 11B) corresponding to multimers of wt-12-wt Fc2 and wt Fc domain monomer.

Example 4—Preparation and SDS-PAGE Analysis of Construct 6

Figures 12A, 12B:
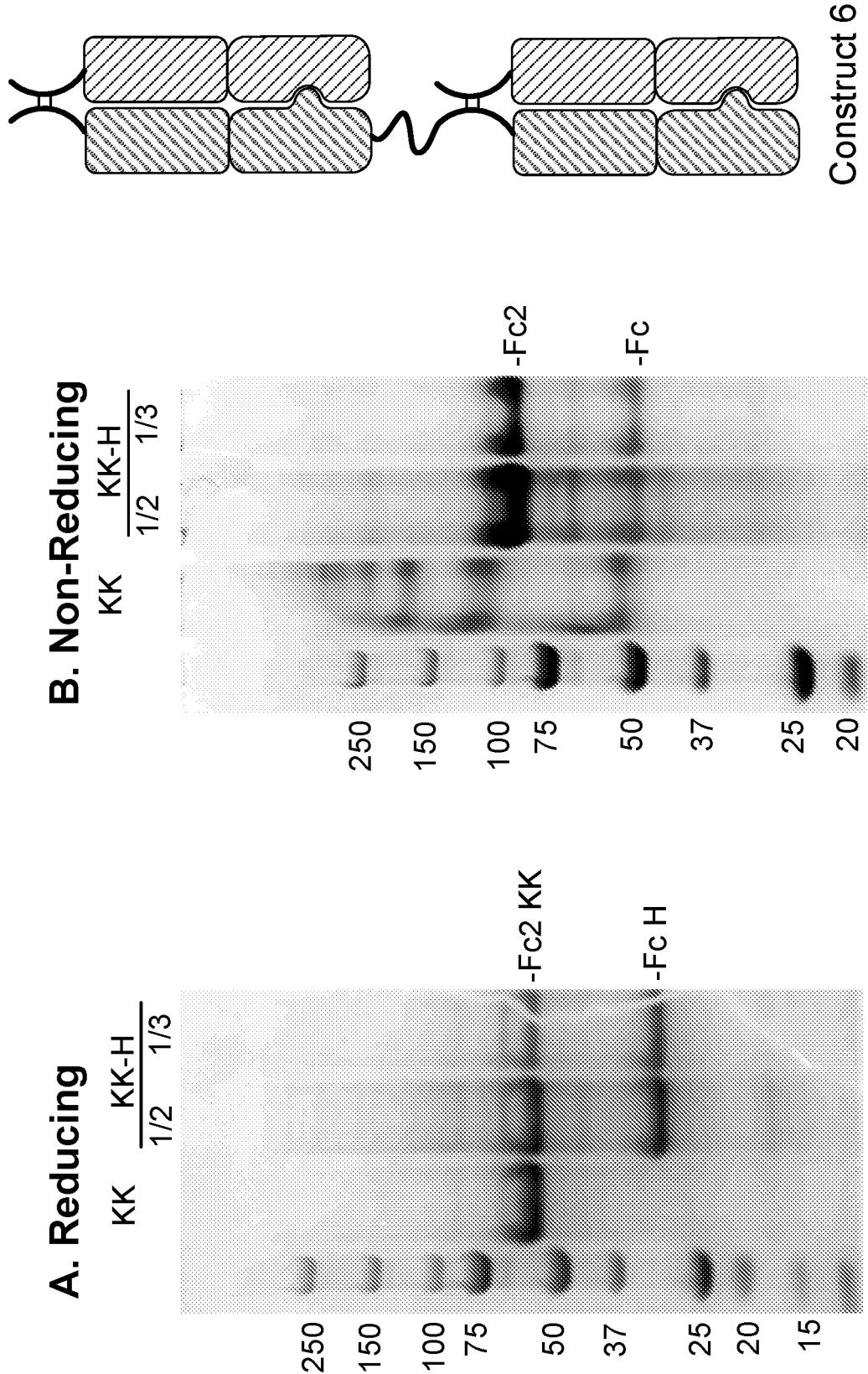
FIGS. 12A-12B show reducing and non-reducing SDS-PAGE of construct 6, respectively.

Two plasmid constructs, protuberance-20-protuberance Fc2 (DNA plasmid construct G in Example 1) and cavity Fc (DNA plasmid construct C in Example 1), were used to express construct 6 (FIG. 6). The two plasmid constructs were transfected into HEK 293 cells for protein expression and purification as described in Example 2. FIGS. 12A-12B show the reducing and non-reducing SDS-PAGE of construct 6. On reducing SDS-PAGE (FIG. 12A), we observed a band at approximately 25 kDa (lanes 2 and 3, FIG. 12A) corresponding to the cavity Fc domain monomer and a band at 50 kDa corresponding to the protuberance-20-protuberance Fc2 tandem dimer (lanes 1-3, FIG. 12A). On non-reducing SDS-PAGE (FIG. 12B), lanes 2 and 3 each contain the final protein product of construct 6 in higher (½) and lower (⅓) protein amounts. We observed one major band at approximately 100 kDa corresponding to the association of the protuberance-20-protuberance Fc2 tandem dimer with two cavity Fc domain monomers and a minor band of weaker signal intensity at approximately 50 kDa corresponding to free protuberance-20-protuberance Fc2 tandem dimer that was not combined with any cavity Fc domain monomer.

Figure 13:
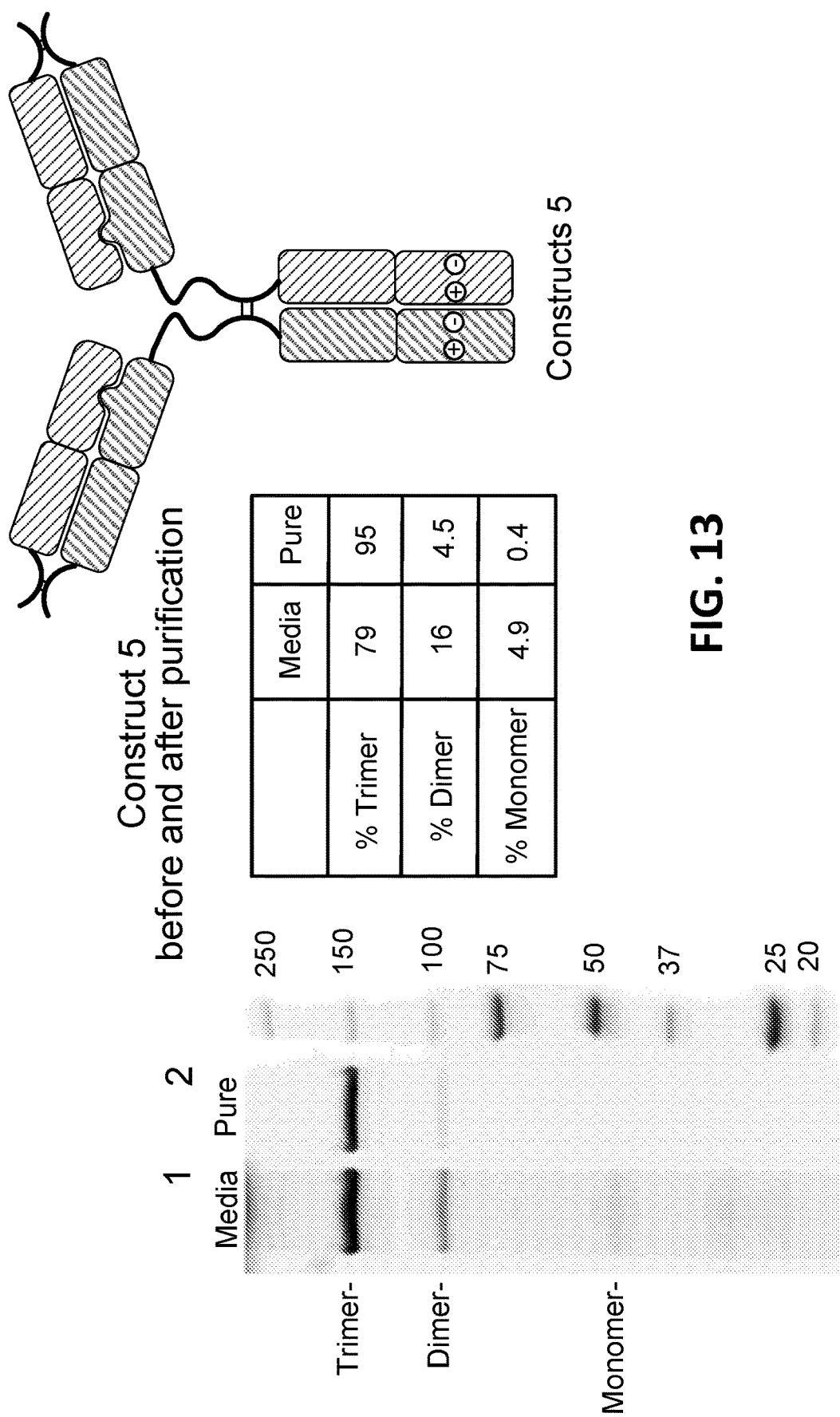
FIG. 13 is an SDS-PAGE of construct 5 and a table showing the percentages of the expressed protein having three Fc domains (trimer), two Fc domains (dimer), or one Fc domain (monomer) before and after construct 5 purification.

A similar experiment was performed with construct 5 (FIG. 13). Two plasmid constructs, protuberance-20-charges Fc2 (DNA plasmid construct F in Example 1) and cavity Fc (DNA plasmid construct C in Example 1), were used to express construct 5 (FIG. 5). The two plasmid constructs were transfected into EXPI293 cells at empirically determined ratios by cationic lipid transfection. The transfected cultures are incubated in cell culture media for 6-8 days. After this time, the cells were removed by centrifugation. The supernatant (media, lane 1 of FIG. 13) contains construct 5 which was secreted by the transfected cells into the media. There are also contaminating host cell proteins in the media. Construct 5 was purified from the media by Protein-A affinity chromatography. At this point, the media contained the desired construct 5 having three Fc domains (trimer) as well as a some proportion of misassembled proteins having two Fc domains (dimer, about 10-15%) and one Fc domain (monomer, 5-10%). There was also a small amount of contaminating host cell proteins still present. The Protein A column eluate was buffer exchanged, concentrated, and fractionated by Strong Cation Exchange (SCX) chromatography. Briefly, construct 5 was bound to the SCX column and then eluted with a salt and pH gradient. This step enabled separation of the desired construct 5 having three Fc domains from most of the misassembled proteins having two or one Fc domain, from construct 5 having unwanted post translational modifications, and from contaminating host cell proteins. After another round of concentration and buffer exchange, a pure, final protein product of construct 5 was obtained (pure, lane 2 of FIG. 13).

FIG. 13 depicts an SDS-PAGE of media obtained from cultured host cells engineered to express construct 5 (lane 1), and of purified construct 5 (lane 2). Also shown is a table showing the percentages of the major bands of the SDS-PAGE for each sample. In the media sample (lane 1), a major band at approximately 150 kDa was observed, corresponding to the final protein product of construct 5 having three Fc domains. The media sample also contained a minor band of weaker signal intensity at 100 kDa corresponding to a protein having two Fc domains, and a second minor band of weakest signal intensity at 50 kDa corresponding a protein having one Fc domain. After purification (lane 2), the major band at approximately 150 kDa, corresponding to the final protein product of construct 5 having three Fc domains is enriched. Quantification of the signal intensities of the protein bands on the SDS-PAGE of construct 5 showed that, in the culture media, before protein purification, about 79% of the total protein was the desired protein product of construct 5. After protein purification, a substantially homogenous population of construct 5 having about 95% purity was obtained.

These findings demonstrate that the selectivity dimerization module containing either an engineered protuberance or an engineered cavity in the $C_H3$ antibody constant domain reduces self-association and prevents uncontrolled Fc-mediated aggregate or multimer formation, indicating that the use of dimerization selectivity modules in the constructs described herein can be used to produce substantially homogenous preparations of the Fc constructs. This observation has significant implications for advantages in manufacturing, yield, and purity of the constructs, e.g., in order to control biological activity and potency.

Example 5—Binding Affinity and Avidity

The binding of constructs to multiple Fcγ receptors was assessed using cell-based FRET competition assays (Cisbio Bioassays). Constructs 5 and 6 showed at least a ten-fold decrease in IC50 (i.e. increased binding) to FcγRIIa, FcγRIIb, and FcγRIIIa relative to the wild type Fc domain (construct 1).

Example 6—Monocyte Activation and Blocking Assays

Figure 14B:
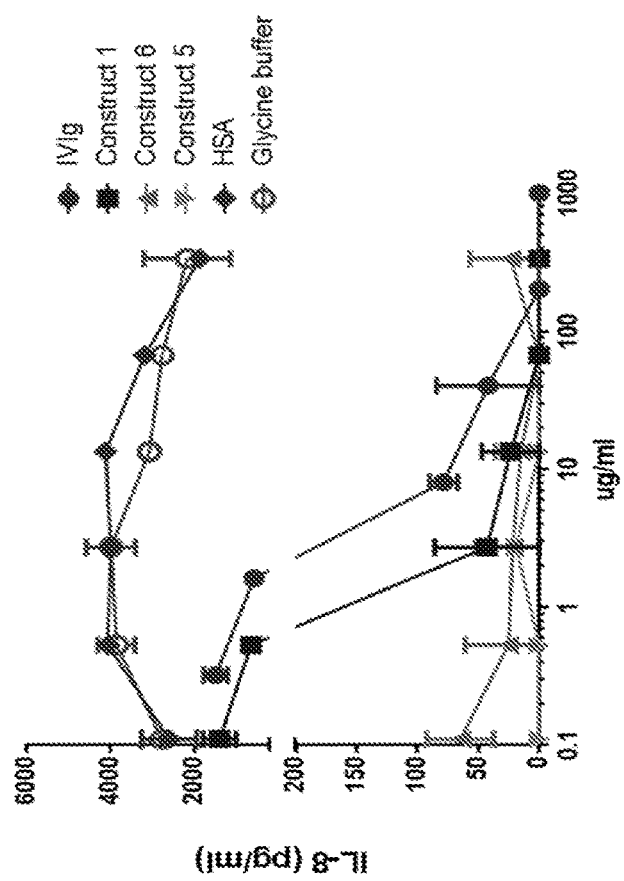
FIGS. 14A and 14B show THP-1 monocyte activation (FIG. 14A) and blocking (FIG. 14B) assays using constructs 1, 5, and 6.
Figure 14A:
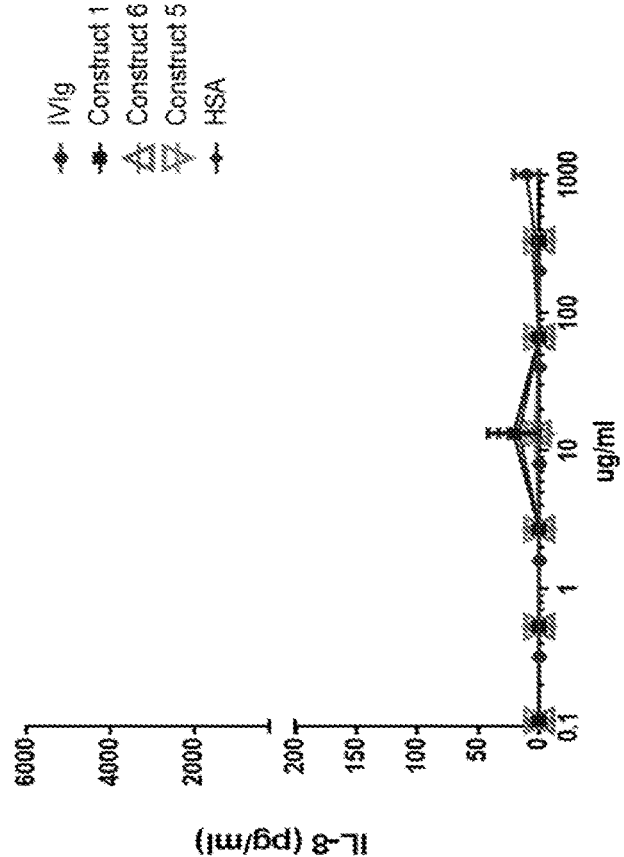

Three Fc constructs, constructs 1, 5, and 6, containing one, three, and two Fc domains, respectively, were tested for their ability to activate THP-1 monocytes on their own. IL-8 release was used as an indicator of monocyte activation. Constructs 1, 5, and 6 were expressed and purified as described in Examples 1 and 2. Each of the purified Fc constructs was added to THP-1 monocytes. No substantial IL-8 release was observed for any of the three constructs. The data are provided in FIG. 14A.

The same three Fc constructs were then tested for their ability to inhibit Fc receptor-mediated monocyte activation. IgG1 (100 μg/mL) was immobilized on a 96 well plate and used to induce IL-8 release by THP-1 monocytes. Serial dilutions of constructs 1, 5 and 6 or control substances (intravenous immunoglobulin (IVIg), human serum albumin (HSA), and glycine buffer) were subsequently performed in the tissue culture plate. THP-1 monocytes ($1.5 \times 10^5$ cells) were immediately added with thorough mixing. The cultures were incubated for 18 h and the supernatants analyzed for IL-8. Constructs 5 and 6 were found to inhibit IL-8 release more effectively than construct 1 at low doses. The data are provided in FIG. 14B.

Example 7—K/BxN Arthritis Model

Figure 15:
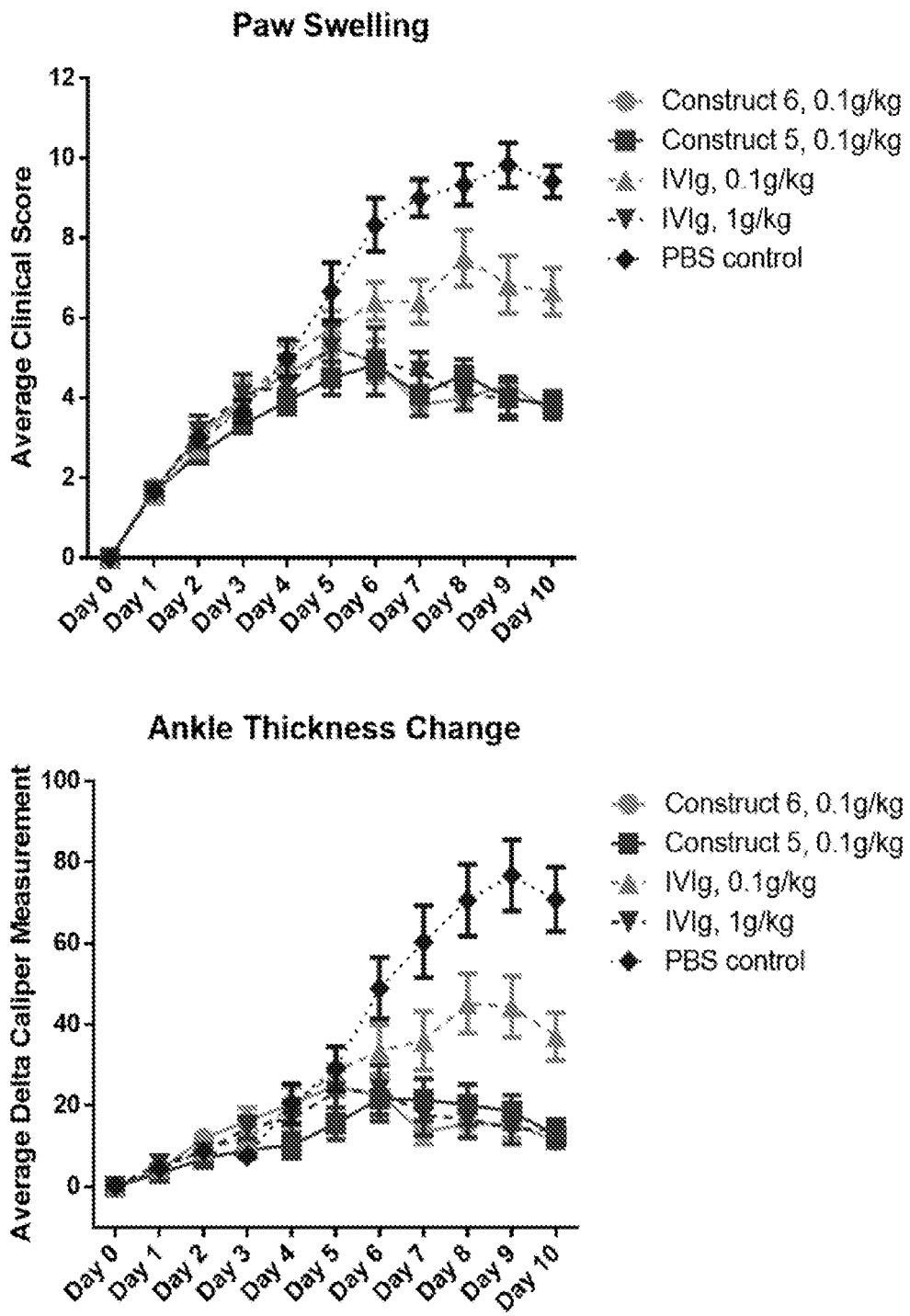
FIG. 15 shows effects of IVIG and constructs 5 and 6 in a K/BxN model of rheumatoid arthritis.

Fc constructs 1, 5, and 6 and IVIg were tested for their ability to protect mice from joint inflammation in the K/BxN serum transfer model using a method described in Anthony, Proc. Natl. Acad. Sci. U.S.A. 105:19571-19578 (2008). Twelve-week old K/BxN mice were generated/purchased from Jackson Laboratories. A total of thirty C57BL mice were separated into five groups of six mice each. Each group was injected intravenously (i.v.) with 200 μl construct 6 at 0.1 g/kg, 200 μl construct 5 at 0.1 g/kg, 200 μl IVIg at 0.1 g/kg, 230 µl IVIg at 1 g/kg, or 200 µl phosphate-buffered saline (PBS) one hour before injection of 200 µl K/B×N serum (an arthritis inducing serum) (Day 0). Inflammation was scored by clinical examination of paw swelling and ankle thickness. For paw swelling, each paw was scored 0-3 (0, no swelling; 3, maximal swelling). Scores of four paws were added for total clinical score per individual mouse. For ankle thickness, caliper measurement was used. Each mouse was scored daily from Day 0 to Day 10. The daily average clinical score for each group of six mice was plotted in FIG. 15. As shown in FIG. 15, IVIg at 1 g/kg, construct 5 at 0.1 g/kg, and construct 6 at 0.1 g/kg provided similar level of inflammation protection. Given that constructs 5 and 6 were administered at ten-fold lower dose compared to the dose of IVIg, constructs 5 and 6 appear to be more potent than IVIg.

Example 8—Chronic ITP Model

Constructs 1 and 5, as well as IVIg, were tested for their ability to treat mice undergoing immune thrombocytopenia (ITP). ITP was induced by an anti-platelet Ab that causes platelet depletion. Forty five C57BL/6 mice (18-22 g, Charles Rivers Labs, MA) were injected i.p. with 1.5 pg/mouse of rat anti-CD41 antibody (Ab) (clone MWReg30 BioLegend cat #133910) once daily for 4 days (on days 1, 2, 3 and 4). Five mice were injected with 1.5 pg/mouse of a rat IgG1, k isotype control Ab (BioLegend cat #400414) to determine normal platelet levels. Abs were injected in 100 µl of PBS. All mice were dosed once intravenously with 200 µl of either saline control, IVIg at 1 g/kg, construct 1 at 0.02, 0.03, 0.1, and 0.3 g/kg, and construct 5 at 0.004, 0.02, and 0.1 g/kg 2 h after the third anti-CD41 Ab injection on day 3. Mice were bled on day 5 (24 h after the forth anti-CD41 Ab injection) to quantitate total platelet levels by the VetScan Instrument. All procedures were performed in compliance with the Animal Welfare Act and with the Guide for the Care and Use of Laboratory Animals.

Figure 16:
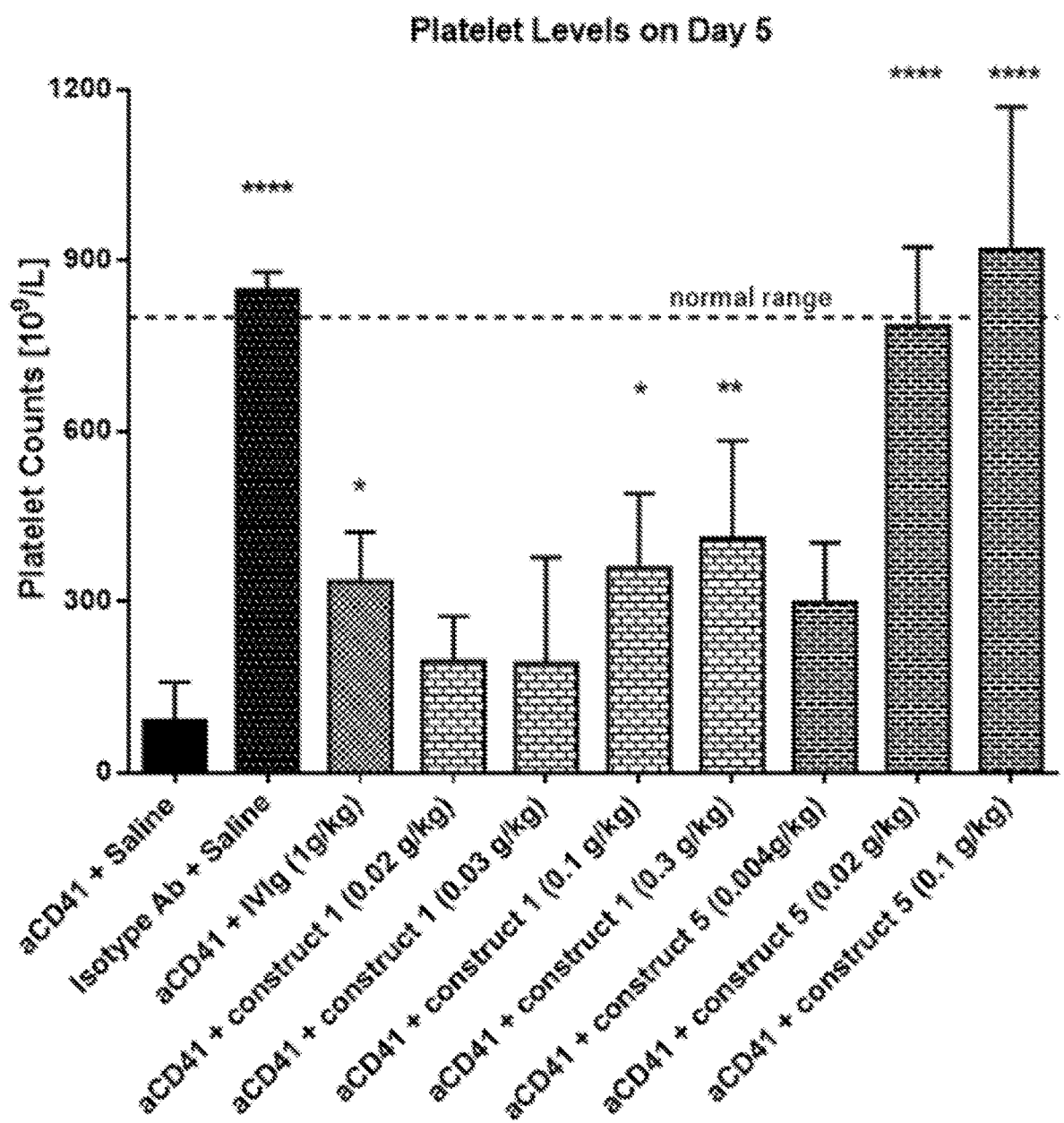
FIG. 16 shows effects of IVIG and constructs 5 and 6 in a chronic ITP model.

As shown in FIG. 16, platelet levels were significantly increased after therapeutic treatment with construct 5 at 0.02 and 0.1 g/kg when compared to saline control (**** $p<0.0001$ by One-way ANOVA with multiple comparisons test). Platelet levels in these groups were similar to the levels in the normal, isotype treated-group. Therapeutic treatment with IVIg at 1 g/kg and construct 1 at 0.1 and 0.3 g/kg, also significantly increased platelet levels when compare to saline control (* $p<0.05$; ** $p<0.01$ respectively by One-way ANOVA with multiple comparisons test) but platelet levels in these groups were lower than in the 0.02 and 0.1 g/kg construct 5 treated-groups. In this model, construct 5 appears to be about 50-fold more potent than IVIg.

Example 9—Construct 5* Shows Augmented Binding and Avidity to FcγR Compared to IVIg Following the same protocol as described in Example 8, two plasmid constructs, encoding protuberance-20-charges Fc2* (construct F* in Example 1) and cavity Fc* (construct C* in Example 1), were used to express and purify construct 5*. The binding profile of this construct to various Fc receptors was compared to that of IVIG in a fluorescence resonance energy transfer (FRET) competitive binding assay.

Construct 5* displayed an overall binding profile to the different Fcγ-receptors similar to that of IVIg (with the lowest binding affinity observed for FcγRIIb) but with greatly enhanced binding to all low affinity FcγRs when compared to IVIg. Augmented binding to FcγR corresponds to higher avidity, which refers to the cumulative effect of the accumulated affinities of each individual binding interaction. IC50 values for construct 5* were consistently lower than those of IVIg, indicating striking increases in binding to low affinity FcγRs compared to individual IgG molecules. For example, compared to IVIg, construct 5* displayed approximately 170 fold increased affinity FcγRIIa (H131 variant), 55 fold increased affinity for FcγRIIb.

Example 10—Inhibition of Phagocytosis in THP-1 Monocytic Cells

Construct 5* and IVIg were Tested in a Model of Phagocytosis.

Phagocytosis is the process by which cells (phagocytes) engulf solid particles such as bacteria, to form an internal vesicle known as a phagosome. In the immune system, phagocytosis is a major mechanism used to remove pathogens and cell debris. Monocytes and macrophages are among the cells specialized in clearing opsonized (antibody coated) particles from the immune system through phagocytosis, a mechanism largely dependent on FcγR mediated engagement. However, in autoimmune diseases, phagocytes can become activated leading to the detrimental release of pro-inflammatory cytokines or the phagocytosis of other critical cells in the body. IVIg, containing pooled, polyvalent, IgG antibodies extracted from the plasma of over one thousand blood donors, is used to treat autoimmune disease.

In this assay system, fluorescently labeled antibody-coated latex beads, a mimic of opsonized bacteria or viruses, were fed to THP-1 cells and allowed to be phagocytosed in the presence and absence of construct 5* and IVIg. At the end of the incubation period, any external fluorescence was quenched with trypan blue, and the amount of intracellular fluorescence quantified by flow cytometry. All groups were normalized to their non-treated control (THP-1 cells and latex beads only). Results are representative of two separate experiments.

Figure 17:
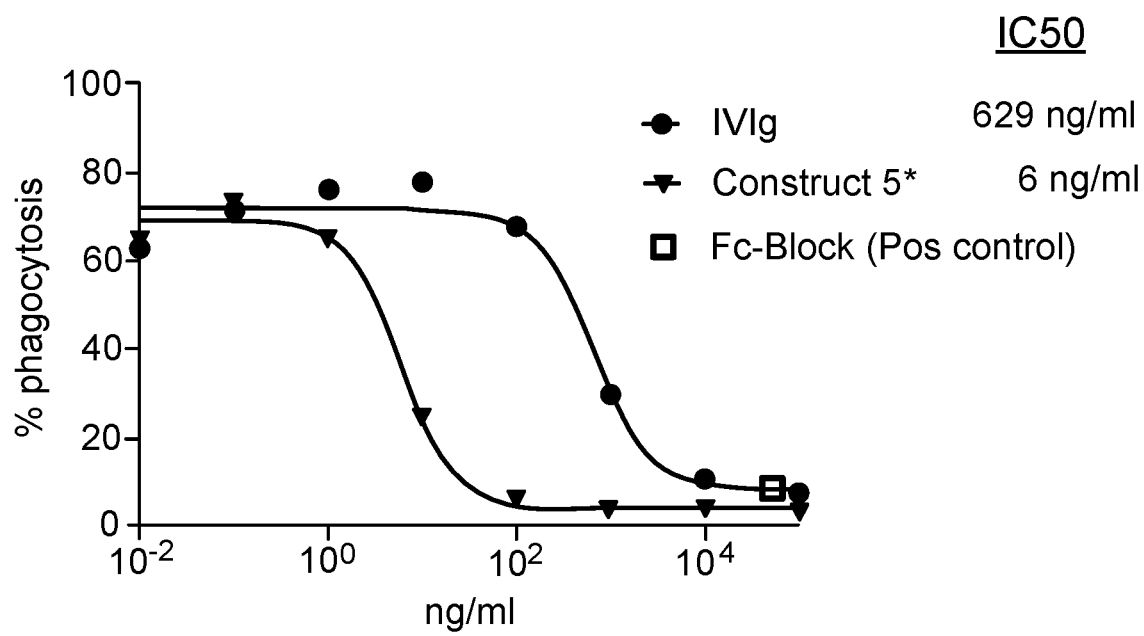
FIG. 17 shows inhibition of phagocytosis by IVIg or Construct 5 in THP-1 monocytic cells.

As shown in FIG. 17, the phagocytosis of opsonized beads by THP-1 monocytic cells is inhibited by treatment with both IVIg and construct 5*, but the IC50 value for construct 5* is approximately 100-fold lower than for IVIg. This suggests that an Fc construct of the disclosure, e.g., construct 5*, can be used to treat autoimmune indications, as well as other indications that are treatable using IVIg.

Example 11—Enhancement of Fc Construct Binding to FcγRIIb

Figure 18:
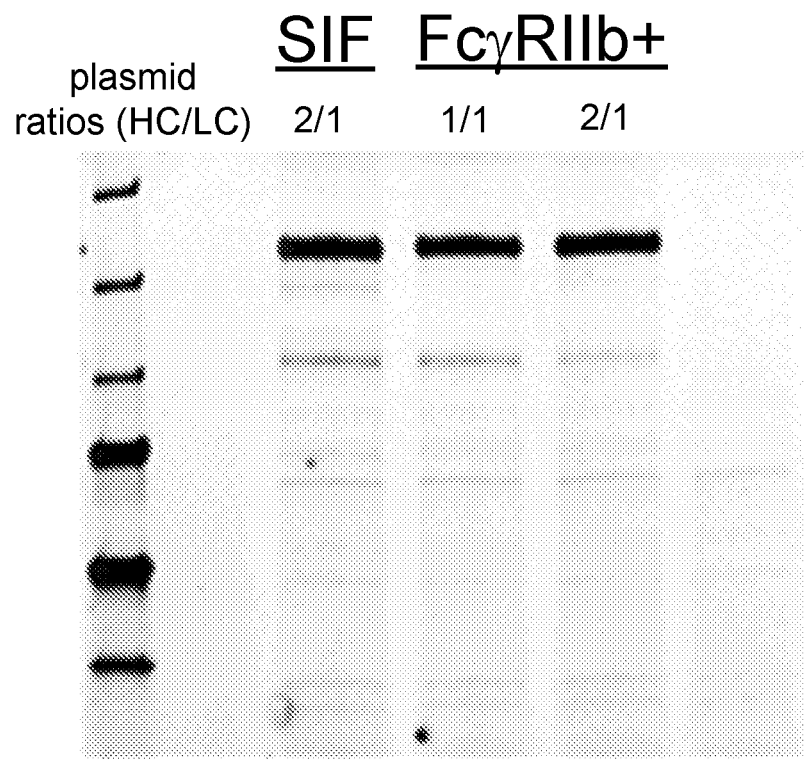
FIG. 18 shows the size distribution by non-reducing SDS-PAGE of clarified media obtained from expression of Construct 5 (SIF) and Construct 5-FcγRIIb+ mutant.

S267E/L328F mutations have been previously shown to significantly and specifically enhance IgG1 binding to the FcγRIIb receptor (Chu et al. Molecular Immunology 45 2008). The S267E/L328F mutations were incorporated into the Construct 5 (SIF) backbone. This Construct 5-FcγRIIb+ mutant expresses and assembles well (see FIG. 18)(SIF: construct 5; FcγRIIb+: Construct 5-FcγRIIb+ mutant). FIG. 18 is an image of the non-reduced sodium dodecyl sulfate polyacrylamide gel electrophoreses results for the clarified media obtained from transient expression of Construct 5 (SIF) and Construct 5-FcγRIIb+ mutant. The plasmids encoding the long and short chains of the Construct 5-FcγRIIb were transfected into HEK293 cells at 1/1 (w/w) or 2/1 ratios.

Binding of the Construct 5-FcγRIIb+ mutant to the inhibitory FcγRIIb receptor was greatly enhanced when compared to the Construct 5 (SIF3) control (over 300 fold increase in binding). Conversely, binding to the activating FcγRIIa is relatively unaffected, whereas binding to FcγRIIIa is reduced (see FIG. 19).

Figure 19:
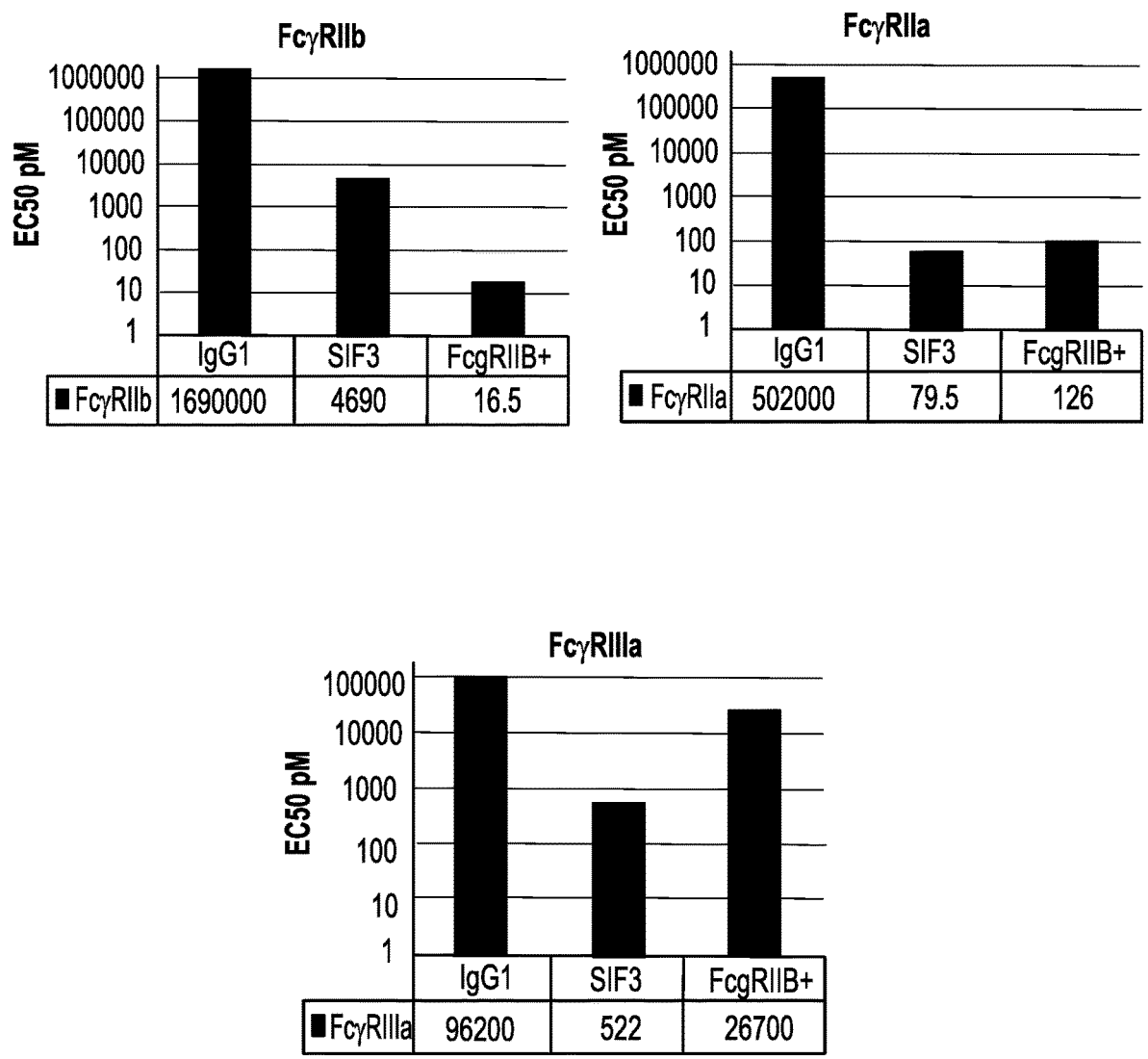
FIG. 19 shows relative binding to Fc gamma receptors of an IgG1 control, Construct 5 (SIF3), and the Construct 5-FcγRIIb+ mutant (FcfRIIB+).

FIG. 19 are graphs that summarize results of experiments which compare binding to Fc gamma receptors of an IgG1 control, Construct 5 and the Construct 5-FcγRIIb+ mutant. Relative binding was measured using cell based, competitive Time Resolved Fluorescence Resonance Energy Transfer assays (CisBio Bioassays, Bedford, Mass.). Results are expressed as EC50 values, indicating the concentration of proband needed to displace a fluorescently labeled antibody bound to the specific cell surface Fc gamma receptor. The higher the number the lower the binding or affinity.

Example 12—Inhibition of Monocyte Derived Dendritic Cells (moDCs) Activation

Figure 20:
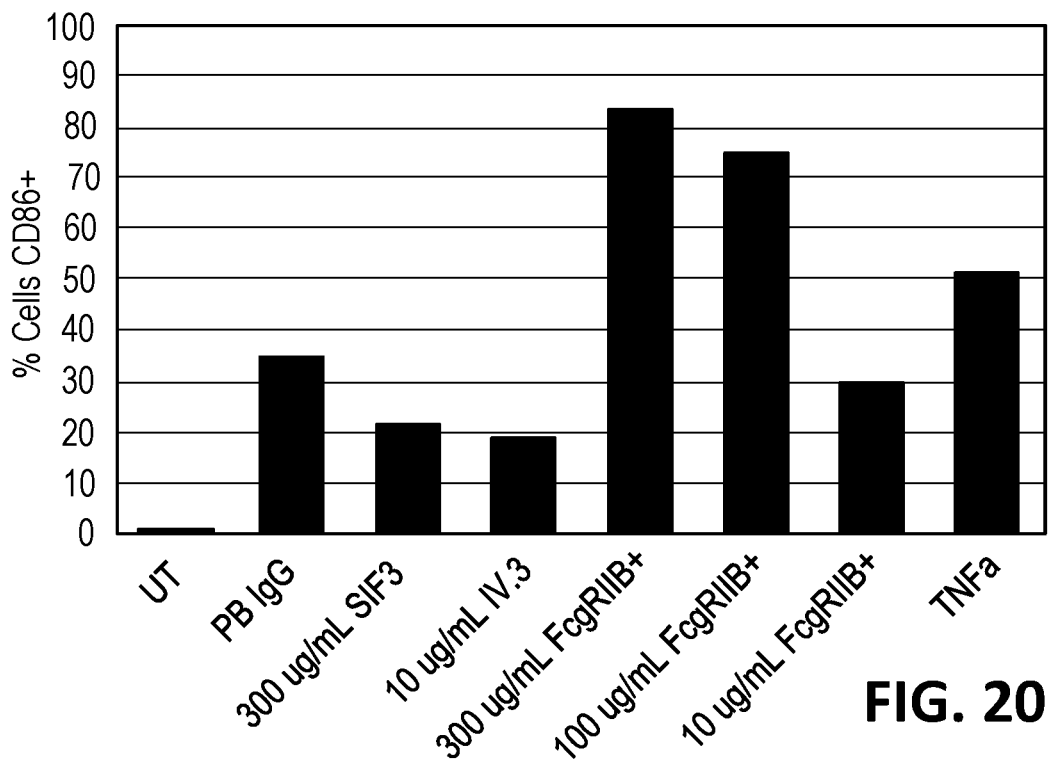
FIG. 20 shows CD86 surface expression on monocyte derived dendritic cells (moDCs).

Construct 5-FcγRIIb+ mutant greatly potentiates activation of monocyte derived dendritic cells (moDCs). Dendritic cells (DCs), which are the most important population of professional antigen presenting cells, process antigen material and present it on the cell surface with the aim of initiating T-cell responses. FcγRs can play a major role in regulating moDC function. Immune complex engagement of activating FcγRs can trigger maturation and activation of immature human moDCs. Conversely, engagement of inhibitory FcγRIIb can suppress maturation and activation (Boruchov A M et al. J Clin Invest. 2005 115(10)). We had previously shown that Fc constructs can inhibit maturation and activation of moDCs (Ortiz et al Sci Transl Med 2016 and see FIG. 3). On the other hand, Fc constructs (e.g., Construct 5/SIF3) with the FcγRIIb+ mutations can significantly potentiate moDC activation in response to exposure to an immune complex surrogate such as plate bound IgG1 (FIG. 20). Incubation with Construct 5-FcγRIIb+ alone does not induce moDC activation (FIG. 21).

Immature human moDCs were generated from negatively selected CD14+ monocytes in the presence of 100 ng/mL GM-CSF and 50 ng/mL IL-4. Harvested DCs were incubated with either PBS, anti-CD32a antibody IV.3, Construct 5 (SIF3), or Construct 5-FcγRIIb+ at 37° C. for 20 min in medium. After blocking, the cell suspension was transferred to the IgG1 coated plates and an additional GM-CSF and IL-4 supplemented medium was added. After a 48 h incubation, lightly adherent cells were harvested by washing plates twice with ice cold PBS. Harvested cells were stained with anti-HLA-DR FITC and anti-CD86-PE Cy7 Abs. Cells were analyzed with a FACSCanto (BD) and FlowJo Software (TreeStar).

FIG. 20: Construct 5 inhibits moDC activation by plate bound IgG whereas Construct 5-FcγRIIb+ enhances activation. Representative histograms show CD86 surface expression on moDCs that were cultured on untreated plates as negative controls (UT) or were pre-treated for 20 min with an antibody blocking activating FcγRIIa (IV.3), with Construct 5 or with increasing concentrations of Construct 5-FcγRIIB+. Treated cells were then transferred to plates containing immobilized IgG1 (PB IgG). Tumor Necrosis Factor alpha (TNFa) treatment was used as a positive control. Surface expression of CD86 was assessed by flow cytometry. Histograms of CD86 expression were gated using unstimulated cells as a control. Percentage of cells positive for CD86 for the treatment conditions are plotted on the y-axis.

Figure 21:
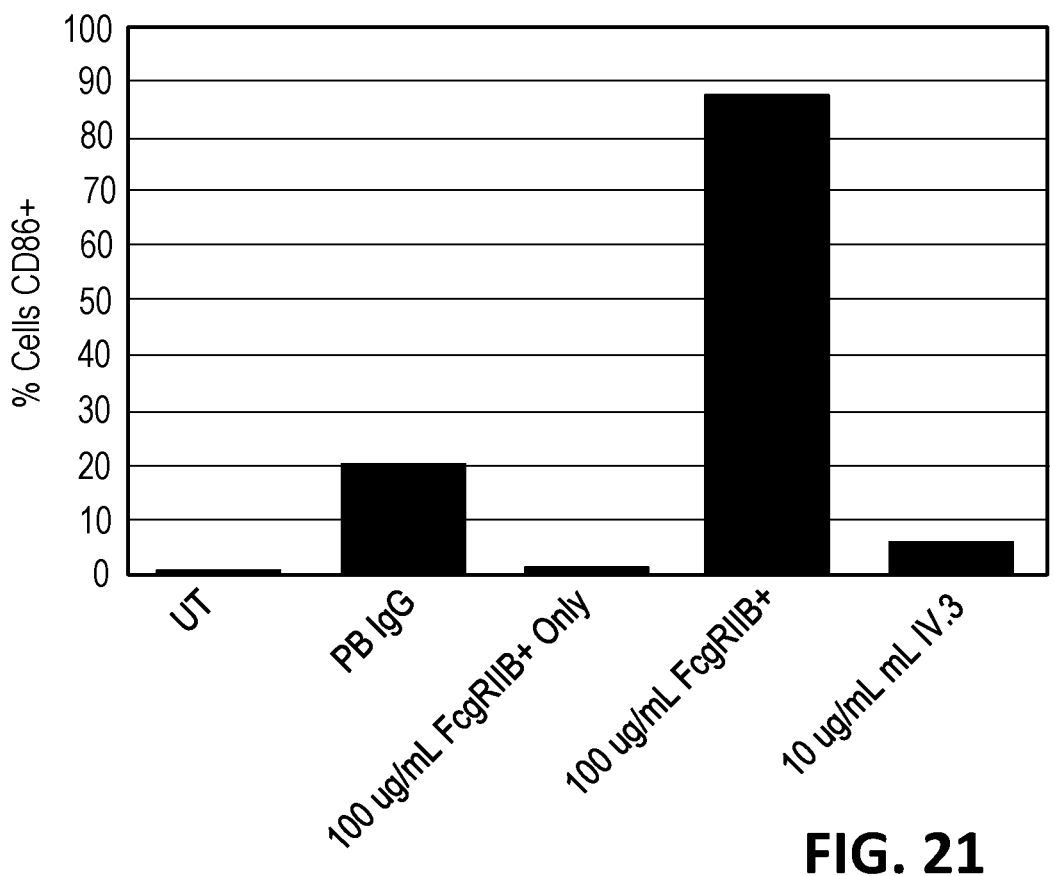
FIG. 21 shows CD86 surface expression on monocyte derived dendritic cells (moDCs).

FIG. 21: Construct 5-FcγRIIb+ does not by itself induce moDC activation but does enhance activation by plate bound IgG. Representative histograms show CD86 surface expression on moDCs that were cultured on untreated plates as negative controls (UT) or pre-treated for 20 min with Construct 5-FcγRIIB+ and then transferred to untreated plates (FcγRIIb+ only). MoDCs pre-treated with PBS (PB IgG), with an antibody that blocks the activating FcγRIIa (IV.3), or with Construct 5-FcγRIIB+ (FcgRIIb+) were transferred to plates containing immobilized IgG1. Surface expression of CD86 was assessed by flow cytometry. Histograms of CD86 expression were gated using unstimulated cells as a control. Percentage of cells positive for CD86 for the treatment conditions are plotted on the y-axis.

The invention claimed is:

1. An Fc construct comprising:
   a) a first polypeptide having the formula A-L-B; wherein
      i) A comprises a first Fc domain monomer;
      ii) L is a linker; and
      iii) B comprises a second Fc domain monomer;
   b) a second polypeptide having the formula A'-L'-B'; wherein
      i) A' comprises a third Fc domain monomer;
      ii) L' is a linker; and
      iii. B' comprises a fourth Fc domain monomer;
   c) a third polypeptide comprises a fifth Fc domain monomer; and
   d) a fourth polypeptide comprises a sixth Fc domain monomer;
   wherein the A of first polypeptide and the A' of second polypeptide combine to form a first Fc domain, the B of first polypeptide and fifth Fc domain monomer combine to form a second Fc domain, and the B' of second polypeptide and sixth Fc domain monomer combine to form a third Fc domain; and
      wherein the first Fc domain monomer and the third Fc domain monomer comprise complementary dimerization selectivity modules that promote dimerization between the first Fc domain monomer and the third Fc domain monomer; second Fc domain monomer and the fifth Fc domain monomer comprise complementary dimerization selectivity modules that promote dimerization between the second Fc domain monomer and the fifth Fc domain monomer; the fourth Fc domain monomer and the sixth Fc domain monomer comprise complementary dimerization selectivity modules that promote dimerization between the fourth Fc domain monomer and the sixth Fc domain monomer;
      wherein each of A, B, A', B', the third polypeptide and the fourth polypeptide comprises an Fc domain monomer; and each Fc domain monomer comprises a hinge domain, a $C_H2$ domain and a $C_H3$ domain; and
      wherein at least one of the Fc domain monomers comprises both a S267E mutation and a L328F mutation that together enhance binding to the FcγRIIb receptor.

2. A method of treating inflammation in a subject, the method comprising administering to the subject a pharmaceutical composition comprising therapeutically effective amount of an Fc construct of claim 1.

3. The Fc construct of claim 1, further comprising an albumin-binding peptide comprising SEQ ID NO: 28.

4. The Fc construct of claim 1, wherein the first polypeptide and the second polypeptide have the same amino acid sequence and wherein the third polypeptide and the fourth polypeptide have the same amino acid sequence.

5. The Fc construct of claim 1, wherein each Fc domain monomers comprises both a S267E mutation and a L328F mutation.

6. The Fc construct of claim 1, wherein each of the first, second, third and fourth polypeptides lack a carboxy-terminal lysine.

7. The Fc construct of claim 1, wherein each dimerization selectivity module independently comprises:
   (a) an engineered cavity in the $C_H3$ domain of one of the Fc domain monomers and an engineered protuberance in the $C_H3$ domain of the other of the Fc domain monomers, wherein the engineered cavity and the engineered protuberance are positioned to form a protuberance-into-cavity pair of Fc domain monomers; or
   (b) a negatively-charged amino acid in the $C_H3$ domain of one of the domain monomers and a positively-charged amino acid in the $C_H3$ domain of the other of the Fc domain monomers, wherein the negatively-charged amino acid and the positively-charged amino acid are positioned to promote formation of an Fc domain.

* * * * *

SEQUENCE LISTING

<160> NUMBER OF SEQ ID NOS: 57

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Ser Gly
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Gly Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ser Gly Ser
1

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ser Gly Ser Gly Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Gly Ser Gly Ser Gly Ser
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ser Gly Ser Gly Ser Gly Ser Gly Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 8

Gly Ser Gly Ser Gly Ser Gly Ser Gly Ser Gly Ser
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Ser Gly Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Ser Gly Gly Ser Gly Gly Ser
1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Ser Gly Gly Ser Gly Gly Ser Gly Gly Ser
1               5                   10

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ser Gly
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Ser Gly
1

<210> SEQ ID NO 14
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Ser Gly Gly Gly Ser Gly
1               5

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Ser Gly Gly Gly Ser Gly Gly Gly Ser Gly
1               5                   10

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Ser
1               5

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Glu Asn Leu Tyr Phe Gln Ser Gly Gly
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ala Cys Tyr Cys Glu Leu Ser
```

```
<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ser Ile Ala Thr
1               5

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Pro Ala Cys Lys Ile Pro Asn Asp Leu Lys Gln Lys Val Met Asn
1               5                   10                  15

His

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
        35

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ala Asn Ser Ser Ile Asp Leu Ile Ser Val Pro Val Asp Ser
1               5                   10                  15

Arg

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24
```

```
Gly Gly Ser Gly Gly Ser Glu Gly Gly Ser Glu Gly Gly Gly
1               5                   10                  15

Ser Glu Gly Gly Gly Ser Glu Gly Gly Ser Glu Gly Gly Ser
                20                  25                  30

Gly Gly Gly Ser
            35
```

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Gly Gly Gly Ser Gly Gly Gly Ser Gly Gly Gly Ser
1               5                   10
```

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Ser Gly Gly Gly Ser Gly Gly Gly Ser Gly Gly Ser Gly Gly Gly
1               5                   10                  15

Ser Gly Gly Gly
            20
```

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gly Gly Ser Gly Gly Gly Ser Gly Gly Gly Ser Gly Gly Gly Ser Gly
1               5                   10                  15

Gly Ser
```

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Asp Ile Cys Leu Pro Arg Trp Gly Cys Leu Trp
1               5                   10
```

<210> SEQ ID NO 29
<211> LENGTH: 681
<212> TYPE: DNA
<213> ORGANISM: Homo sapiens

<400> SEQUENCE: 29

```
gacaagaccc acacctgtcc gccttgccct gccccctgagc tgctgggagg ccccagcgtg      60
```

```
ttcctgttcc ccccaaagcc caaggacacc ctgatgatca gccggacccc cgaagtgacc       120
tgcgtggtgg tggacgtgtc ccacgaggac cctgaagtga agttcaattg gtacgtggac       180
ggcgtggaag tgcacaacgc caagaccaag cccagagagg aacagtacaa cagcacctac       240
cgggtggtgt ccgtgctgac cgtgctgcac caggactggc tgaacggcaa agaatacaag       300
tgcaaagtct ccaacaaggc cctgcctgcc cccatcgaga aaaccatcag caaggccaag       360
ggccagcccc gcgagcccca ggtgtacaca ctgccccca gccgggacga gctgaccaag        420
aaccaggtgt ccctgacctg cctggtgaaa ggcttctacc ccagcgatat cgccgtggaa       480
tgggagagca acggccagcc cgagaacaac tacaagacca ccccccctgt gctggacagc       540
gacggctcat tcttcctgta cagcaagctg accgtggaca gagccggtg gcagcagggc        600 aacgtgttca gctgcagcgt gatgcacgag gccctgcaca accactacac ccagaagtcc       660
ctgagcctga gccccggcaa g                                                 681

<210> SEQ ID NO 30
<211> LENGTH: 227
<212> TYPE: PRT
<213> ORGANISM: Homo sapiens

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 31
<211> LENGTH: 681
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacaagaccc acacctgtcc gccttgccct gcccctgagc tgctgggagg ccccagcgtg    60
ttcctgttcc ccccaaagcc caaggacacc ctgatgatca gccggacccc cgaagtgacc   120
tgcgtggtgg tggacgtgtc ccacgaggac cctgaagtga agttcaattg gtacgtggac   180
ggcgtggaag tgcacaacgc caagaccaag cccagagagg aacagtacaa cagcacctac   240
cgggtggtgt ccgtgctgac cgtgctgcac caggactggc tgaacggcaa agaatacaag   300
tgcaaagtct ccaacaaggc cctgcctgcc cccatcgaga aaaccatcag caaggccaag   360
ggccagcccc gcgagcccca ggtgtacaca ctgcccccct gccgggacga gctgaccaag   420
aaccaggtgt ccctgtggtg cctggtgaaa ggcttctacc ccagcgatat cgccgtggaa   480
tgggagagca acggccagcc cgagaacaac tacaagacca ccccccctgt gctggacagc   540
gacggctcat tcttcctgta cagcaagctg accgtggaca gagccggtg gcagcagggc   600 aacgtgttca gctgcagcgt gatgcacgag gccctgcaca accactacac ccagaagtcc   660
ctgagcctga gccccggcaa g                                             681

<210> SEQ ID NO 32
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Lys
225

<210> SEQ ID NO 33
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gacaagaccc acacctgtcc gccttgccct gcccctgagc tgctgggagg ccccagcgtg        60
ttcctgttcc ccccaaagcc caaggacacc ctgatgatca gccggacccc cgaagtgacc       120
tgcgtggtgg tggacgtgtc ccacgaggac cctgaagtga agttcaattg gtacgtggac       180
ggcgtggaag tgcacaacgc caagaccaag cccagagagg aacagtacaa cagcacctac       240
cgggtggtgt ccgtgctgac cgtgctgcac caggactggc tgaacggcaa agaatacaag       300
tgcaaagtct ccaacaaggc cctgcctgcc cccatcgaga aaaccatcag caaggccaag       360
ggccagcccc gcgagcccca agtgtgtaca ctgcccccca gccgggacga gctgaccaag       420
aaccaggtgt ccctgagctg cgccgtgaaa ggcttctacc ccagcgatat cgccgtggaa       480
tgggagagca acggccagcc cgagaacaac tacaagacca cccccccctgt gctggacagc       540 gacggctcat tcttcctggt tagcaagctg accgtggaca gagccggtg gcagcagggc        600 aacgtgttca gctgcagcgt gatgcacgag gccctgcaca accactacac ccagaagtcc       660
ctgagcctga gccccggcaa g                                                 681

<210> SEQ ID NO 34
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

```
Cys Thr Leu Pro Pro Ser Arg Asp Glu Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 35
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gacaagaccc acacctgtcc gccttgccct gccccctgagc tgctgggagg ccccagcgtg    60
ttcctgttcc ccccaaagcc caaggacacc ctgatgatca gccggacccc cgaagtgacc   120
tgcgtggtgg tggacgtgtc ccacgaggac cctgaagtga agttcaattg gtacgtggac   180
ggcgtggaag tgcacaacgc caagaccaag cccagagagg aacagtacaa cagcacctac   240
cgggtggtgt ccgtgctgac cgtgctgcac caggactggc tgaacggcaa agaatacaag   300
tgcaaagtct ccaacaaggc cctgcctgcc cccatcgaga aaaccatcag caaggccaag   360
ggccagcccc gcgagcccca ggtgtacaca ctgcccccca gccgggacga gctgaccaag   420
aaccaggtgt ccctgacctg cctggtgaaa ggcttctacc ccagcgatat cgccgtggaa   480
tgggagagca acggccagcc cgagaacaac tacaagacca cccccccctgt gctgaaaagc   540 gacggctcat tcttcctgta cagcgacctg accgtggaca agagccggtg gcagcagggc   600
aacgtgttca gctgcagcgt gatgcacgag gccctgcaca accactacac ccagaagtcc   660
ctgagcctga gccccggcaa g                                              681

<210> SEQ ID NO 36
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
```

| | | | | | | | | | | | | | | |
|---|---|---|---|---|---|---|---|---|---|---|---|---|---|---|
|His|Asn|Ala|Lys|Thr|Lys|Pro|Arg|Glu|Glu|Gln|Tyr|Asn|Ser|Thr|Tyr|
|65| | | |70| | | |75| | | |80| | | |

Arg Val Val Ser Val Leu Thr Val Leu His Gln Asp Trp Leu Asn Gly
                        85                              90                              95

Lys Glu Tyr Lys Cys Lys Val Ser Asn Lys Ala Leu Pro Ala Pro Ile
            100                          105                            110

Glu Lys Thr Ile Ser Lys Ala Lys Gly Gln Pro Arg Glu Pro Gln Val
            115                          120                          125

Tyr Thr Leu Pro Pro Ser Arg Asp Glu Leu Thr Lys Asn Gln Val Ser
    130                           135                          140

Leu Thr Cys Leu Val Lys Gly Phe Tyr Pro Ser Asp Ile Ala Val Glu
145                      150                          155                      160

Trp Glu Ser Asn Gly Gln Pro Glu Asn Asn Tyr Lys Thr Thr Pro Pro
                165                        170                        175

Val Leu Lys Ser Asp Gly Ser Phe Phe Leu Tyr Ser Asp Leu Thr Val
            180                          185                        190

Asp Lys Ser Arg Trp Gln Gln Gly Asn Val Phe Ser Cys Ser Val Met
            195                          200                        205

His Glu Ala Leu His Asn His Tyr Thr Gln Lys Ser Leu Ser Leu Ser
    210                           215                          220

Pro Gly Lys
225

<210> SEQ ID NO 37
<211> LENGTH: 1398
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 37

| | | |
|---|---|---|
|gacaagaccc acacctgtcc cccttgccct gcccctgagc tgctgggagg ccccagcgtg|60|
|ttcctgttcc ccccaaagcc caaggacacc ctgatgatca gccggacccc cgaagtgacc|120|
|tgcgtggtgg tggacgtgtc ccacgaggac cctgaagtga agttcaattg gtacgtggac|180|
|ggcgtggaag tgcacaacgc caagaccaag cccagagagg aacagtacaa cagcacctac|240|
|cgggtggtgt ccgtgctgac cgtgctgcac caggactggc tcaacggcaa agagtacaag|300|
|tgcaaggtgt ccaacaaggc cctgcctgcc cccatcgaga aaaccatcag caaggccaag|360|
|ggccagcccc gcgagcccca ggtctacaca ctgcccccca gccgggacga gctgaccaag|420|
|aaccaggtct ccctgacctg cctggtgaaa ggcttctacc ccagcgatat cgccgtggaa|480|
|tgggagagca acggccagcc cgagaacaac tacaagacca cccccctgt gctggacagc|540|
|gacggctcat tcttcctgta cagcaagctg accgtggaca agagccggtg gcagcagggc|600|
|aacgtgttca gctgcagcgt gatgcacgag gccctgcaca accactacac ccagaagtcc|660|
|ctgagcctga gccccggcaa aggcggggga tctggggag aagcggagg cggcagcgat|720|
|aagacccata cctgccctcc ctgtcccgct cccgaactgc tggggggacc ctccgtgttt|780|
|ctgtttccac ctaagcctaa ggatacgctc atgatctcca gaacccctga agtcacatgt|840|
|gtggtggtcg atgtgtctca tgaagatccc gaagtcaagt ttaactggta tgtggatggg|900|
|gtcgaggtcc acaatgccaa acaaagcct cgggaagaac agtataactc cacctacaga|960|
|gtcgtcagcg tgctgacagt ccttcatcag gattggctga atgggaaaga gtacaaatgt|1020|
|aaagtgtcta acaaagctct gccgctcct atcgaaaaga ccatctccaa agccaaaggg|1080|

-continued

```
cagcccagag aacctcaggt gtacaccctg ccaccctcca gagatgagct gacaaaaaat    1140
caggtgtcac tgacatgtct ggtgaaaggg ttttatccct ccgacattgc tgtggaatgg    1200
gaatccaatg ggcagcctga aaacaattat aagacaacac ctcccgtgct ggactccgat    1260
ggctcatttt ttctgtactc taaactgaca gtggataagt ccagatggca gcagggaaat    1320
gtgttttcct gctctgtgat gcatgaagct ctgcataatc actatacaca gaaaagcctg    1380
tccctgtccc ccggcaag                                                  1398
```

<210> SEQ ID NO 38
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Gly Gly Gly Ser Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
```

```
                    290                 295                 300
Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 39
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gacaagaccc acacctgtcc cccttgccca gcccctgagc tgctgggagg ccccagcgtg      60
ttcctgttcc ccccaaagcc caaggacacc ctgatgatca gccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa cagcacctac     240
cgggtggtgt ccgtgctgac cgtgctgcac caggactggc tgaacggcaa agagtacaag     300
tgcaaggtgt ccaacaaggc cctgcctgcc cccatcgaga aaaccatcag caaggccaag     360
ggccagcccc gcgagcccca ggtgtacacc ctgcccccct tgcagagatga gctgaccaag     420 aaccaggtgt ccctgtggtg cctggtcaag ggcttctacc ccagcgatat cgccgtggaa     480
tgggagagca acggccagcc cgagaacaac tacaagacca ccccccctgt gctggacagc     540
gacggctcat tcttcctgta cagcaagctg accgtggaca gagccggtg gcagcagggc     600 aacgtgttca gctgcagcgt gatgcacgag gccctgcaca accactacac ccagaagtcc     660
ctgagcctga gccccggcaa gtctggggga ggatcagggg gtggaagtgg cggtggatct     720
ggtggtggaa gcgaggcggc gataagaca cacacatgcc cccctgtcc agctcccgaa     780 ctgctggggg gaccctccgt gtttctgttt ccacctaagc ctaaggatac gctcatgatc     840
tccagaaccc ctgaagtcac atgtgtggtg gtcgatgtgt ctcatgaaga tcccgaagtc     900
aagtttaatt ggtatgtcga tggggtcgag gtgcacaatg ccaaaacaaa acctcgggaa     960
gaacagtata actccacata cagagtggtg tctgtcctca cagtcctgca tcaggattgg    1020
```

```
ctcaatggga aagagtacaa atgtaaagtc tctaacaagg ctctccccgc tccgatcgaa   1080
aagaccatct ccaaagccaa agggcagccc agagaacctc aggtctacac actgcctccc   1140
agccgggacg agctgacaaa aaatcaagtg tctctgacct gcctcgtgaa gggcttttat   1200
ccctccgaca ttgccgtcga gtgggagtcc aatggacagc cggaaaacaa ttataagacc   1260
acgcctccag tgctgaagtc cgacggcagc ttctttctgt actccgacct gacagtggat   1320
aagtccagat ggcagcaagg gaatgtgttc tcctgttccg tgatgcatga agccctccat   1380
aatcactata cccagaaaag cctgtccctg tccctggca ag                      1422

<210> SEQ ID NO 40
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ser Gly Gly Gly Ser Gly Gly Gly Ser Gly Gly Gly Ser
225                 230                 235                 240

Gly Gly Gly Ser Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 41
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gacaagaccc acacctgtcc cccttgccct gcccctgagc tgctgggagg ccccagcgtg      60
ttcctgttcc ccccaaagcc caaggacacc ctgatgatca gccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa cagcacctac     240
cgggtggtgt ccgtgctgac cgtgctgcac caggactggc tgaacggcaa agagtacaag     300
tgcaaggtgt ccaacaaggc cctgcctgcc cccatcgaga aaaccatcag caaggccaag     360
ggccagcccc gcgagcccca ggtgtacacc ctgccccctt gcagagatga actgaccaag     420
aaccaggtgt ccctgtggtg cctggtcaag ggcttctacc ccagcgatat cgccgtggaa     480
tgggagagca acggccagcc cgagaacaac tacaagacca ccccccctgt gctggacagc     540
gacggctcat tcttcctgta cagcaagctg accgtggaca gagccggtg gcagcagggc      600 aacgtgttca gctgcagcgt gatgcacgag gccctgcaca accactacac ccagaagtcc     660
ctgagcctga gccccggcaa gtctggggga ggatcagggg gtggaagtgg cggtggatct     720
ggtggtggaa gcggaggcgg cgataagaca cacacatgcc cccctgtcc agctcccgaa      780 ctgctggggg gacctccgt gtttctgttt ccacctaagc ctaaggatac gctcatgatc      840
tccagaaccc ctgaagtcac atgtgtggtg gtcgatgtgt ctcatgaaga tcccgaagtc     900
aagtttaact ggtatgtgga tggggtcgag gtccacaatg ccaaaacaaa gcctcgggaa     960

```
gaacagtata actccaccta cagagtcgtc agcgtgctga cagtcctgca tcaagattgg    1020
ctcaatggga aagagtataa gtgtaaagtc tcgaacaaag ccctccccgc tcctatcgaa    1080
aagaccatct ccaaagccaa agggcagccc agagaacctc aggtctacac actgcctcca    1140
tgtcgggacg agctgacaaa aaatcaggtg tcactgtggt gtctggtgaa ggggttttac    1200
ccttccgaca ttgctgtgga atgggaatcc aatgggcagc ctgaaaacaa ttataagaca    1260
acacctcccg tgctggactc cgatggctca ttttttctgt actctaaact gacagtggat    1320
aagtccagat ggcagcaggg aaatgtgttt tcctgctctg tgatgcatga agctctgcat    1380
aatcactata cacagaaaag cctgtccctg tcccctggca ag                      1422
```

<210> SEQ ID NO 42
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ser Gly Gly Gly Ser Gly Gly Gly Ser Gly Gly Gly Ser
225                 230                 235                 240

Gly Gly Gly Ser Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270
```

```
Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Cys Arg Asp Glu
370                 375                 380

Leu Thr Lys Asn Gln Val Ser Leu Trp Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 43
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
aggacagtgg ccgctcccag cgtgttcatc ttcccaccca gcgacgagca gctgaagtcc    60
ggcacagcca gcgtggtctg cctgctgaac aacttctacc cccgcgaggc caaggtgcag   120
tggaaggtgg acaacgccct gcagagcggc aacagccagg aaagcgtcac cgagcaggac   180
agcaaggact ccacctacag cctgtctagc accctgaccc tgagcaaggc cgactacgag   240
aagcacaagg tgtacgcctg cgaagtgacc caccagggcc tgtccagccc cgtgaccaag   300
agcttcaaca gaggcgagtg cggcggctct ggcggaggat ccgggggagg atcaggcggc   360
ggaagcggag gcagcgctag cacaaagggc ccctccgtgt tcccctggc ccccagcagc   420 aagagcacat ctggcggaac agccgccctg ggctgcctgg tgaaagacta cttccccgag   480
cccgtgaccg tgtcctggaa ctctggcgcc ctgaccagcg gcgtgcacac ctttccagcc   540
gtgctgcaga gcagcggcct gtactccctg agcagcgtgg tgacagtgcc tagcagcagc   600
ctgggcaccc agacctacat ctgcaacgtg aaccacaagc ccagcaacac caaagtggac   660
aagcgggtgg aacccaagag ctgcgacaag acccacacgt gtcccccctg cccagcccct   720
gaactgctgg gcggacctag cgtgttcctg ttccccccaa agcccaagga caccctgatg   780
atcagccgga ccccccgaagt gacctgcgtg gtggtggacg tgtcccacga ggaccctgaa   840
gtgaagttca attggtacgt ggacggcgtg gaagtgcaca atgccaagac caagcccaga   900
```

-continued

```
gaggaacagt acaacagcac ctaccgggtg gtgtccgtgc tgaccgtgct gcaccaggac    960
tggctgaacg gcaaagagta caagtgcaag gtctccaaca aggccctgcc tgcccccatc   1020
gagaaaacca tcagcaaggc caagggccag ccccgcgagc ccaggtgta cacactgccc    1080 cccagccggg acgagctgac caagaaccag gtgtccctga cctgtctggt gaaaggcttc   1140 taccccctccg atatcgccgt ggaatgggag agcaacggcc agcccgagaa caactacaag   1200
accacccccc ctgtgctgga ctccgacggc tcattcttcc tgtacagcaa gctgaccgtg   1260
gacaagagcc ggtggcagca gggcaacgtg ttcagctgct ccgtgatgca cgaggccctg   1320
cacaaccact acacccagaa gtccctgagc ctgagccccg gcaaa                    1365
```

<210> SEQ ID NO 44
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Gly Gly Ser Gly Gly
            100                 105                 110

Gly Ser Gly Gly Gly Ser Gly Gly Gly Ser Gly Gly Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

```
Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 45
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Glu Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 46
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Ser Gly Gly Gly Ser Gly Gly Gly Ser Gly Gly Gly Ser
225                 230                 235                 240

Gly Gly Gly Ser Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
```

```
            290                 295                 300
Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
        370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
                420                 425                 430

Leu Tyr Ser Asp Leu Thr Val Asp Lys Ser Arg Trp Gln Gln Gly Asn
            435                 440                 445

Val Phe Ser Cys Ser Val Met His Glu Ala Leu His Asn His Tyr Thr
        450                 455                 460

Gln Lys Ser Leu Ser Leu Ser Pro Gly Lys
465                 470
```

<210> SEQ ID NO 47
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
gacaagaccc acacctgtcc gccttgccct gcccctgagc tgctgggagg ccccagcgtg    60
ttcctgttcc ccccaaagcc caaggacacc ctgatgatca gccggacccc cgaagtgacc   120
tgcgtggtgg tggacgtgtc ccacgaggac cctgaagtga agttcaattg gtacgtggac   180
ggcgtggaag tgcacaacgc caagaccaag cccagagagg aacagtacaa cagcacctac   240
cgggtggtgt ccgtgctgac cgtgctgcac caggactggc tgaacggcaa agaatacaag   300
tgcaaagtct ccaacaaggc cctgcctgcc cccatcgaga aaaccatcag caaggccaag   360
ggccagcccc gcgagcccca agtgtgtaca ctgcccccca gccgggacga gctgaccaag   420
aaccaggtgt ccctgagctg cgccgtggac ggcttctacc ccagcgatat cgccgtggaa   480
tgggagagca acggccagcc cgagaacaac tacaagacca cccccccgtgt gctggacagc   540
gacggctcat tcttcctggt tagcaagctg accgtggaca gagccggtg gcagcagggc   600
aacgtgttca gctgcagcgt gatgcacgag gccctgcaca accactacac ccagaagtcc   660
ctgagcctga gccccggcta g                                             681
```

<210> SEQ ID NO 48
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 49
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gacaagaccc acacctgtcc cccttgccca gcccctgagc tgctgggagg ccccagcgtg      60
ttcctgttcc ccccaaagcc caaggacacc ctgatgatca gccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa cagcacctac     240
cgggtggtgt ccgtgctgac cgtgctgcac caggactggc tgaacggcaa agagtacaag     300
tgcaaggtgt ccaacaaggc cctgcctgcc cccatcgaga aaaccatcag caaggccaag     360
ggccagcccc gcgagcccca ggtgtacacc ctgccccctt gcagagataa gctgaccaag     420
aaccaggtgt ccctgtggtg cctggtcaag ggcttctacc ccagcgatat cgccgtggaa     480
tgggagagca acggccagcc cgagaacaac tacaagacca ccccccctgt gctggacagc     540
gacggctcat tcttcctgta cagcaagctg accgtggaca gagccggtg gcagcagggc      600 aacgtgttca gctgcagcgt gatgcacgag gccctgcaca accactacac ccagaagtcc     660

```
ctgagcctga gccccggcaa gggaggggga ggaggagggg gtggaggtgg cggtggaggc    720
ggtggtggag gcggaggcgg cgataagaca cacacatgcc ccccctgtcc agctcccgaa    780
ctgctggggg gaccctccgt gtttctgttt ccacctaagc ctaaggatac gctcatgatc    840
tccagaaccc ctgaagtcac atgtgtggtg gtcgatgtgt ctcatgaaga tcccgaagtc    900
aagtttaatt ggtatgtcga tggggtcgag gtgcacaatg ccaaaacaaa acctcgggaa    960
gaacagtata actccacata cagagtggtg tctgtcctca cagtcctgca tcaggattgg   1020
ctcaatggga aagagtacaa atgtaaagtc tctaacaagg ctctccccgc tccgatcgaa   1080
aagaccatct ccaaagccaa agggcagccc agagaacctc aggtctacac actgcctccc   1140
agccgggacg agctgacaaa aaatcaagtg tctctgacct gcctcgtgaa gggcttttat   1200
ccctccgaca ttgccgtcga gtgggagtcc aatggacagc cggaaaacaa ttataagacc   1260
acgcctccag tgctgaagtc cgacggcagc ttctttctgt actccgacct gacagtggat   1320
aagtccagat ggcagcaagg gaatgtgttc tcctgttccg tgatgcatga agccctccat   1380
aatcactata cccagaaaag cctgtccctg tcccctggct ag                      1422
```

<210> SEQ ID NO 50
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys Gly Gly Gly Gly Gly Gly Gly Gly Gly
225                 230                 235                 240

Gly Gly Gly Gly Gly Gly Asp Lys Thr His Thr Cys Pro Pro Cys
            245                 250                 255

Pro Ala Pro Glu Leu Leu Gly Gly Pro Ser Val Phe Leu Phe Pro Pro
        260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
            435                 440                 445

Val Phe Ser Cys Ser Val Met His Glu Ala Leu His Asn His Tyr Thr
        450                 455                 460

Gln Lys Ser Leu Ser Leu Ser Pro Gly
465                 470

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Gly Gly
1

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Gly Gly Gly Gly
1               5

<210> SEQ ID NO 53

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Gly Gly Gly Gly Gly Gly Gly Gly Gly
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Gly Gly Gly Gly Gly Gly Gly Gly Gly Gly Gly Gly Gly
1               5                   10                  15

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Gly Gly Gly Gly Gly Gly Gly Gly Gly Gly Gly Gly Gly Gly
1               5                   10                  15

Gly Gly Gly Gly
            20

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 56

His His His His His His
1               5

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Ser
1
```